(12) United States Patent
Masuda et al.

(10) Patent No.: US 8,227,455 B2
(45) Date of Patent: Jul. 24, 2012

(54) METHODS OF TREATING CELL PROLIFERATIVE DISORDERS

(75) Inventors: Esteban Masuda, Menlo Park, CA (US); Donald G. Payan, Hillsborough, CA (US); Elliot B. Grossbard, San Francisco, CA (US); Somasekhar Bhamidipati, Foster City, CA (US); Rajinder Singh, Belmont, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 969 days.

(21) Appl. No.: 11/407,233

(22) Filed: Apr. 18, 2006

(65) Prior Publication Data

US 2006/0276459 A1    Dec. 7, 2006

Related U.S. Application Data

(60) Provisional application No. 60/672,648, filed on Apr. 18, 2005, provisional application No. 60/706,710, filed on Aug. 8, 2005.

(51) Int. Cl.
*A61K 31/33* (2006.01)
(52) U.S. Cl. ...................................................... 514/183
(58) Field of Classification Search ................... 514/183
See application file for complete search history.

(56) References Cited

U.S. PATENT DOCUMENTS

| | | | |
|---|---|---|---|
| 5,958,935 A | 9/1999 | Davis et al. | |
| 5,985,856 A * | 11/1999 | Stella et al. | 514/80 |
| 6,593,326 B1 | 7/2003 | Bradbury et al. | |
| 7,449,458 B2 * | 11/2008 | Bhamidipati et al. | 514/230.5 |
| 2003/0195169 A1* | 10/2003 | Gillman et al. | 514/80 |
| 2005/0113398 A1 | 5/2005 | Argade et al. | |
| 2005/0171171 A1* | 8/2005 | Mehta et al. | 514/378 |
| 2005/0209224 A1 | 9/2005 | Singh et al. | |
| 2005/0234049 A1 | 10/2005 | Singh et al. | |
| 2006/0211657 A1 | 9/2006 | Singh et al. | |
| 2006/0234983 A1* | 10/2006 | Singh et al. | 514/81 |
| 2006/0276459 A1 | 12/2006 | Masuda et al. | |
| 2007/0060603 A1 | 3/2007 | Singh et al. | |

FOREIGN PATENT DOCUMENTS

| | | |
|---|---|---|
| WO | 00/39101 | 7/2000 |
| WO | 02/059110 | 8/2002 |
| WO | 03/026664 | 4/2003 |
| WO | 03/030909 | 4/2003 |
| WO | 2003040141 A1 | 5/2003 |
| WO | 2003055489 A1 | 7/2003 |
| WO | 2004014832 A1 | 2/2004 |
| WO | 2004087698 A2 | 10/2004 |
| WO | WO 2005/016893 A2 * | 2/2005 |
| WO | WO2005013996 * | 2/2005 |
| WO | 2005027848 A2 | 3/2005 |
| WO | 2006068770 A1 | 6/2006 |

OTHER PUBLICATIONS

Hoelzer et al 'Recent approaches in acute lymphoblastic leukemia in adults' Critical Reviews in Oncology/Hematology, vol. 36, p. 49-58, 2000.*
Pine et al 'An Orally Bioavailable Inhibitor of FLT3 and Syk Kinases Prevents Tumor Growth in Subcutaneously Implanted Human Tumor Xenografts and Promotes Cell Death in FLT3 Mutant AML cells' Blood (ASH Annual Meeting Abstracts), vol. 106, Abstract 243, 2005.*
U.S. Appl. No. 10/913,270: Office Action mailed Sep. 18, 2008, Summary of interview conducted Dec. 15, 2008, Response filed Dec. 18, 2008, Advisory Action mailed Jan. 12, 2009, RCE filed Jan. 15, 2009, Applicants' Summary of interview conducted Dec. 15, 2008.
U.S. Appl. No. 112/567,284: Office Action mailed Sep. 9, 2008, Response filed Feb. 5, 2009.
U.S. Appl. No. 11/567,817: Office Action mailed Sep. 9, 2008, Response filed Jan. 8, 2009.
Pine et al., "An Orally Bioavailable Inhibitor of FLT3 and Syk Kinases Prevents Tumor Growth in Subcutaneously Implanted Human Tumor Xenografts and Promotes Cell Death in FLT3 Mutant AML Cells", Blood (ASH Annual Meeting Abstracts), vol. 106, Abstract 243, 2005 (complete copy).
Pine et al., "An Orally Bioavailable Inhibitor of FLT3 and Syk Kinases Prevents Tumor Growth in Subcutaneously Implanted Human Tumor Xenografts and Promotes Cell Death in FLT3 Mutant AML Cells", Presentation at ASH Annual Meeting, Dec. 12, 2005.
U.S. Appl. No. 10/913,270, including Office Action mailed Jun. 10, 2009.
U.S. Appl. No. 11/567,817, including Office Action mailed Jun. 16, 2009.
U.S. Appl. No. 11/567,820, including Office Action mailed Jun. 16, 2009.
U.S. Appl. No. 11/567,824, including Office Action mailed Jun. 16, 2009.
U.S. Appl. No. 11/940,930, filed Nov. 15, 2007, Hitoshi, et al.
U.S. Appl. No. 11/567,817, filed Dec. 7, 2006, Argade, et al.
U.S. Appl. No. 11/567,820, filed Dec. 7, 2006, Argade, et al.
U.S. Appl. No. 11/567,824, filed Dec. 7, 2006, Argade, et al.
U.S. Appl. No. 11/567,780, filed Dec. 7, 2006, Argade, et al.
Talmadge, James E., et al., "Murine Models to Evaluate Novel and Conventional Therapeutic Strategies for Cancer," The American Journal of Pathology, Mar. 2007, vol. 170, No. 3, pp. 793-804.
Suggitt, Marie, et al., "50 Years of Preclinical Anticancer Drug Screening: Empirical to Target-Driven Approaches," Clinical Cancer Research, Feb. 1, 2005, vol. 11, pp. 971-981.

* cited by examiner

*Primary Examiner* — Brandon Fetterolf
*Assistant Examiner* — Christopher R Stone
(74) *Attorney, Agent, or Firm* — Travis Young; McDonnell Boehnen Hulbert & Berghoff LLP

(57) ABSTRACT

The present disclosure provides methods for the treatment of cell proliferative disorders by administration of a Syk kinase or Syk/Flt-3 kinase inhibitor. Cell proliferative disorders treatable by the methods include, hematopoietic neoplasms and virally associated tumors. The compounds are also directed to therapeutic or prophylactic inhibition of tumor metastasis.

40 Claims, 25 Drawing Sheets

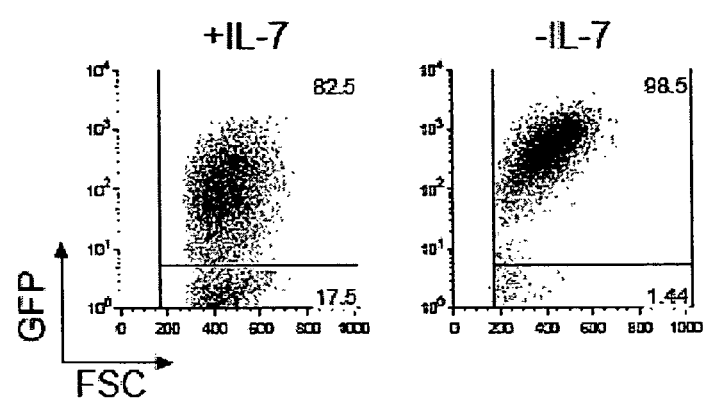
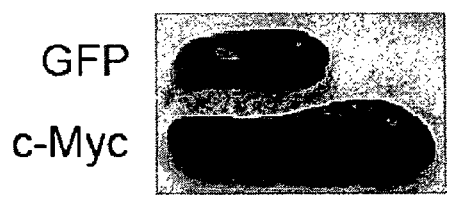
FIG. 2A
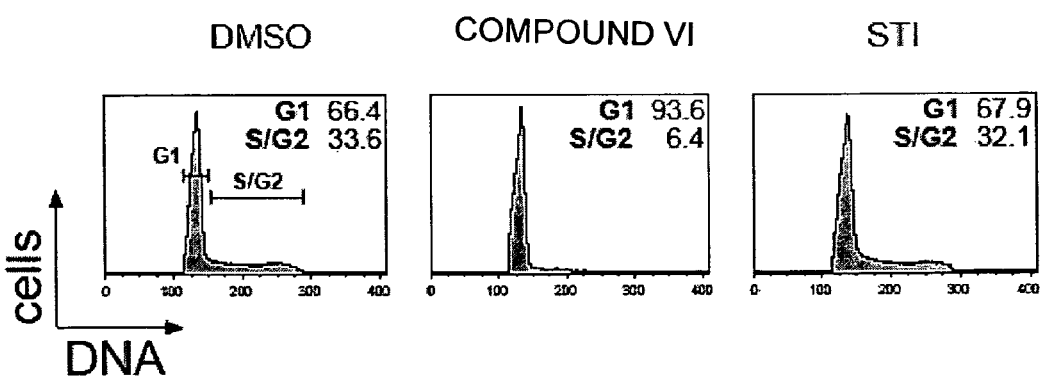
FIG. 2B

A

B

FIG. 16
Rat PK Profiles for Prodrug Compound 4
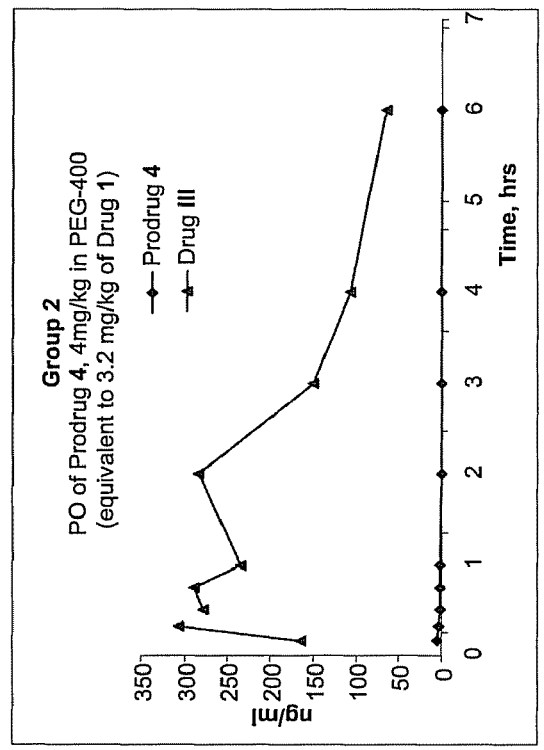
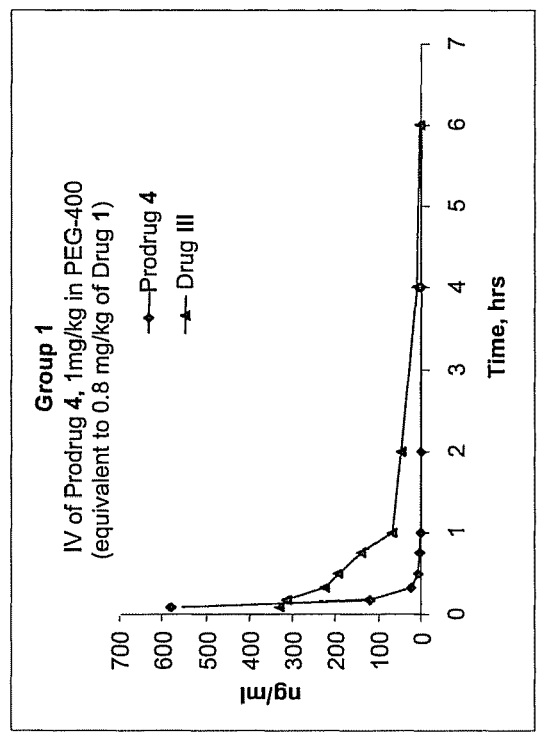

FIG. 17

PK Summary

| Mode of Delivery | Analyte | Parameter | Value | Comments |
|---|---|---|---|---|
| IV | Prodrug 4 | Clearance, ml/min/kg | 93.1 | AUC of 4 = 182<br>AUC of 1 = 327 |
| | | T1/2, hr | 0.2 | |
| PO | Drug III | %F | 29.9 | Total absorbed and converted to Drug III |
| | | Cmax, ng/ml | 331 | |
| | Prodrug 4 | %F | 0.3 | |
| | | Cmax, ng/ml | 5.23 | | cLogD vs pH (Pallas) and Measured Solubility

- Solubility (Prodrug 4) in Phosphate buffer (pH = 7.5, 100 mM)
- Conditions:
  - 0.4mg in 80 ul buffer (5 mg/ml). Insoluble material removed by centrifugation at 2 and 24hrs.
  - LC/MS/MS analysis.

| Time, hrs | Solubility, mg/ml | |
|---|---|---|
| | replicate 1 | replicate 2 |
| 2 | 5.04 | 4.94 |
| 24 | 5.09 | 5.03 |

Chemical Stability of Prodrug 4

Metabolic Stability: Microsomes

- p-nitrophenyl phosphate (PNP) is stable in microsomes and S9 fractions.
- PNP is a known substrate for both acid and alkaline phosphatase Plasma Stability (Rat) of Prodrug 4 and PNP Rat PK Study of Prodrug 4

METHODS OF TREATING CELL PROLIFERATIVE DISORDERS

1. CROSS-REFERENCE TO RELATED APPLICATIONS

This application claims benefit under 35 U.S.C. §119(e) to application Ser. No. 60/672,648, filed Apr. 18, 2005, and application Ser. No. 60/706,710, filed Aug. 8, 2005, the contents of which are incorporated herein by reference.

2. TECHNICAL FIELD

The present disclosure relates to methods and compositions for treating cell proliferative disorders, where the compositions comprise inhibitors that target kinase activities affecting the proliferative potential of cells.

3. BACKGROUND

Unregulated cell growth is the hallmark of tumors and cancers and other cell proliferative disorders. The cellular processes controlling cell division and cell proliferation are complex, involving an intricate interplay between gene products that promote cell division and growth and those that hold such processes in check. Positive regulators of growth and proliferation are generally described as proto-oncogenes, which are the normal counterparts of altered genes and their gene products known to promote tumor and cancer formation. Proto-oncogenes promote cell division and negatively control cell apoptosis. Uncoupling the activity of these gene products from their normal regulated state converts the proto-oncogenes to oncogenes. Normal function of proto-oncogenes includes growth factors, growth factor receptors, cellular signal transduction molecules, and nuclear factors. Activation of the proto-oncogenes into oncogenic forms can occur in a variety of ways, including gene mutation, amplification, gene translocation, and viral activation.

Tumor suppressors, as opposed to the proto-oncogenes, generally exert a negative effect on cell growth, promote apoptosis of cells, inhibit cell cycle progression, and affect invasive and metastatic potential. In some instances, tumor suppressors can counter the activity of oncogenes even in their altered forms. Upon loss or inhibition of tumor suppressor function, the unregulated activity of proto-oncogenes or their corresponding oncogenic forms leads to cell transformation and carcinogenesis. Gene mutation or deletion, suppressed transcription, increased degradation, or abnormalities of associated proteins that work in concert with the tumor suppressors may compromise tumor suppressor activity. Tumor suppressor genes act as recessive alleles such that a cell with a normal allele along with a mutant allele still behaves normally. Thus, loss of the normal allele, also called loss of heterozygozity (LOH), characterizes some types of abnormal cell growth and proliferation. Genomic instability arising as a consequence of oncogene activity and disruption of normal cell division controls can increase the probability of LOH and thus the occurrence of the transformed phenotype by oncogenes.

Treatment of cell proliferative disorders can target the oncogenes and/or the tumor suppressors affected in the transformed cells. However, a disorder arising from a loss-of-function, such as a tumor suppressor, is typically more problematic when attempting to treat the underlying molecular defect than treating the underlying molecular defect in a disorder arising from a gain-of-function change, such as activation of an oncogene. Altering cellular processes to provide the lost cellular function is not practicable in many cases. Thus, even for cell proliferative disorders arising from loss of tumor suppressor activity, therapy is typically directed at the dysregulated molecules (e.g., proto-oncogenes) that act as a consequence of the lost tumor suppressor function. Although many molecular targets have been identified, such as non-receptor and receptor based protein kinases, the complex nature of the cellular regulatory mechanisms at play in cell proliferation and growth would indicate that other molecules that could be targets of therapy remain to be identified. Some of these will be unknown while others may be known but not linked to cell proliferative disorders.

Thus it is desirable to identify other cellular molecules that act in an oncogenic manner in cell proliferative disorders, either as a consequence of alteration of its own activity or as a result of loss of a cellular function that act to regulate its activity. Upon identification of such molecules, compounds specifically directed to that cellular molecule can be identified and used, either independently or in combination with other known therapies, to treat the cell proliferative disorder.

4. SUMMARY

The present disclosure provides method of treating cell proliferative disorders by administration to subjects an amount of a Syk kinase inhibitory compound effective to treat the cell proliferative disorder. In some embodiments, the Syk kinase inhibitor is selective for Syk kinase, thereby specifically targeting the aberrant Syk kinase activity present in the proliferative disorder. Any cell proliferative disorder in which Syk plays a role in some aspect of abnormal cell division or cell growth can be treated with the inhibitor compounds. In some embodiments, the cell proliferative disorders treatable with the inhibitor compounds are hematopoietic neoplasms, which are abnormal growth involving cells of the hematopoietic lineage. Hematopoietic neoplasms treatable with the Syk inhibitory compounds include, among others, various myeloid and lymphoid neoplasms, such as chronic myelogenous leukemia, Burkitt's lymphoma, and acute myelogenous leukemia.

In some embodiments, the Syk kinase inhibitory compound comprises a Syk/Flt-3 kinase inhibitory compound, capable of inhibiting the activity of both Syk kinase and Flt-3 kinase. These compounds can be used to treat cell proliferative disorders that are associated with aberrant Flt-3 kinase activity. Various hematopoietic neoplasms in which Flt-3 activity is abnormal include, among others, acute myelogenous leukemia, B-precursor cell acute lymphoblastic leukemia, T-cell acute lymphoblastic leukemia, myelodysplastic syndrome, and chronic myelogenous leukemia. These and other such disorders involving Flt-3 can be treated with the Syk/Flt-3 inhibitory compounds, such as members of the 2,4-pyrimidinediamine compounds described herein.

In other aspects, the inhibitor compounds can be used to treat tumors mediated by viral genes that transform a normal cell into a tumor cell. In these embodiments, tumors in which the activity of a viral oncogene disrupts Syk kinase function as part of its transformation mechanism can be targeted for treatment. Thus, in some embodiments, virally mediated tumors are associated with infection by viruses carrying genes encoding proteins with immunoreceptor tyrosine-based activation motifs (ITAM). Normally, these conserved sequences modulate Syk kinase activity during development and function of immune system cells (e.g., B cells, T cells, neutrophils, etc.). However, persistent expression of viral proteins with ITAM sequences can lead to aberrant Syk kinase activity and consequent tumor formation and/or maintenance. In various embodiments, the virally mediated tumors can be associated with Karposi's sarcoma-associated herpes virus, Epstein Barr virus, human T-cell lymphotrophic virus (HTLV-1), or mammary tumor virus (MTV). Presence of these viruses are correlated with a number of cell proliferative disorders, including, Karposi's sarcoma, Burkitt's lymphoma, Hodgkin's lymphoma, adult T cell leukemia, and certain forms of breast cancer.

In some aspects, the disclosure provides a method of inhibiting tumor metastasis by administration to a subject an amount of a Syk inhibitory compound effective to inhibit tumor metastasis. Any tumor with metastatic potential can be treated with the inhibitor compounds. In some embodiments, the tumor metastasis is associated with the activity of integrins, which can act through Syk kinase in modulating cell adhesive properties, such as that observed in metastasis of tumor cells. Syk kinase inhibitors can be used to inhibit tumor metastasis by affecting cell signaling events mediated by integrins, such as $\beta1$, $\beta2$, and/or $\beta3$ integrins.

In some aspects, the inhibitor compounds can be used in combination with other cancer treatments. In some embodiments, Syk inhibitory compounds are used in combination with other chemotherapeutic agents, including, among others, antimetabolites, alkylating agents, coordination compounds, transcription inhibitors, topoisomerase inhibitors, DNA minor-groove binding compounds, vinca alkyloids, antitumor antibiotics, hormones, and antitumor enzymes.

5. BRIEF DESCRIPTION OF THE FIGURES

FIG. 1A, FIG. 1B, and FIG. 1C show the ability of Syk inhibitor compound VI to block proliferation and induce differentiation of TEL-Syk-transformed cells. DNA content of TEL-Syk- or BCRAbl-transformed cells treated for 36 hours with either DMSO, the Syk inhibitor compound VI (2 μM) or Abl kinase inhibitor STI-571 (2 μM) are shown in FIG. 1A. The ability of TEL-Syk to blocks pre-B cell differentiation is shown in FIG. 1B. Cells were cultured for 3 days in the absence of IL-7 and analyzed for the expression of kappa LC by FACS. Inhibition of TEL-Syk activity with compound VI is shown in FIG. 1C.

FIG. 2A and FIG. 2B show the ability of Syk inhibitor VI to block the proliferation of Myc-transformed pre-B cells. FIG. 2A is a FACS profile of pre-B cells that were transduced with Myc expression vectors and cultured in the absence of IL-7 for 1 week. Lower panel of FIG. 2B shows spleens of RAG/γC-± mice 5 weeks after injection with the indicated cells, illustrating the ability of the Myc transformed cells to cause splenomegaly and leukemia. FIG. 2B shows the DNA content of Myc-transformed cells that were treated for 36 hours with either DMSO, VI (2 μM) or STI-571 (2 μM).

FIG. 3A and FIG. 3B show the ability of Syk inhibitor VI to block the proliferation of tumorigenic SLP-65$^{-/-}$ pre-B cell lines. FIG. 3A shows that SLP-65$^{-/-}$ pre-B cell lines can cause splenomegaly and leukemia, as evidenced by the state of spleens of RAG/γC$^{-/-}$ mice 5 weeks after injection with the indicated cells. FIG. 3B shows the DNA content of tumorigenic SLP-65$^{-/-}$ pre-B cell lines that were treated for 36 hours with either DMSO, VI (2 μM) or STI-571 (2 μM).

FIG. 4 shows survival curves for NOD-SCID mice inoculated intravenously (i.v.) with MV4-11 human acute myeloid leukemia cells and treated with compound VII at 40 mg/kg twice daily, PO, from day 17 post tumor cell inoculation for the duration of the study. Calculations for % ILS for 40 mg/kg VII group ($10^6$ cells) assumes median day of death of 83 days, due to greater than 50% survival in this group at study termination (Day 83).

FIG. 5 shows days to death for individual animals. The survival data is for NOD-SCID mice injected intravenously with MV4-11 tumor cells. Mice were treated with vehicle or varying doses of VII twice daily, PO, from day 17 post-tumor cell injection until the end of the study (Day 83). Days to death for sacrificed animals are shown in the graph with median day of death denoted by blue line. The survivors in each group at study termination are shown at the top of the graph denoted as # survivors/total # mice.

FIG. 6A and FIG. 6B show frequency of tumors in MV4-11 tumor bearing NOD-SCID mice at necropsy. The severity of disease was evaluated by quantitating the frequency of mice having palpable tumors upon necropsy at termination, irrespective of reason for sacrifice (FIG. 6A). The total number of tumors per group is shown in FIG. 6B. Mice were inoculated i.v. with 5 or 10 million MV4-11 human AML cells (denoted as 5E6 or 10E6, respectively). At Day 17 post cell injection, mice were treated with vehicle or 40 mg/kg VII (PO, bid) until sacrifice or for the duration of the study, up to Day 83 for surviving animals. Mice were sacrificed and a comprehensive necropsy performed. The total number of necropsies performed per group ranged from 8-13 animals.

FIG. 7 shows the tumor distribution profile of experimental animals. Percent of total tumors found in various anatomical locations were noted upon necropsy at sacrifice. Mice were injected i.v. with 5 or 10 million MV4-11 cells and dosed orally with either vehicle or 40 mg/kg of VII twice daily for the duration of the study. Animals showing enlarged salivary glands are included in the graph, although no palpable tumor was detected. The total number of necropsies performed per group ranged from 8-13 animals.

FIG. 8 shows the engraftment profile of MV4-11 tumor cells in bone marrow (BM) and peripheral blood (PB) of NOD-SCID mice. The data is from engraftment of MV4-11 human tumor cells in NOD-SCID mice treated with vehicle or 40 mg/kg VII twice daily, PO, from day 17 post i.v. tumor cell injection until the end of the study. Bone marrow (BM) and peripheral blood (PB) tumor cell engraftment were detected by flow cytometric analysis using CD33 and HLA cell surface staining for detection of MV4-11 tumor cells. Data were normalized, and percent human tumor cells out of total cells were calculated. Total cells were defined as the number of human CD33+HLA+ positive events and murine CD45 positive staining events. Graph includes all samples.

FIG. 9 shows detection of Flt-3 in Mv4-11 xenografts by immunoprecipitation and Western Blot analysis. Panel A is detection of phosphorylated Flt-3 in MV4-11 tumor lysates from mice approximately two hours after the final dose of VII or vehicle using anti-phosphotyrosine antibody on the left and anti-phospho-Flt-3 specific antibody on the right side of the blot. Additionally, a reprobe of the blot for the total Flt-3 levels are shown in Panel B.

FIG. 10 shows phosphorylated histone H3 analysis of MV4-11 tumor xenografts. Proliferation was assessed ex vivo in formalin fixed tumor sections from three randomly selected mice from this study using immunohistochemical staining of human-specific phosphorylated histone H3 (phH3) as a marker for tumor cell proliferation. Human phH3 expression was reduced in tumor sections in a dose-dependent manner following treatment with VII. When compared to Mv4-11 tumor xenografts from vehicle treated mice, treatment with 20 and 40 mg/kg VII resulted in a 53% and 71% inhibiton of phH3 staining, respectively. These data indicate that VII mediated inhibition reduced the proliferative capacity of MV4-11 tumors in vivo, correlating with the reduced tumor volumes observed during the in-life portion of the study. The reduced proliferation is likely to be due to reduced constitutive Flt-3 phosphorylation, as this activity has been shown to be required for survival of MV4-11 cells in vitro.

Figure 13A:
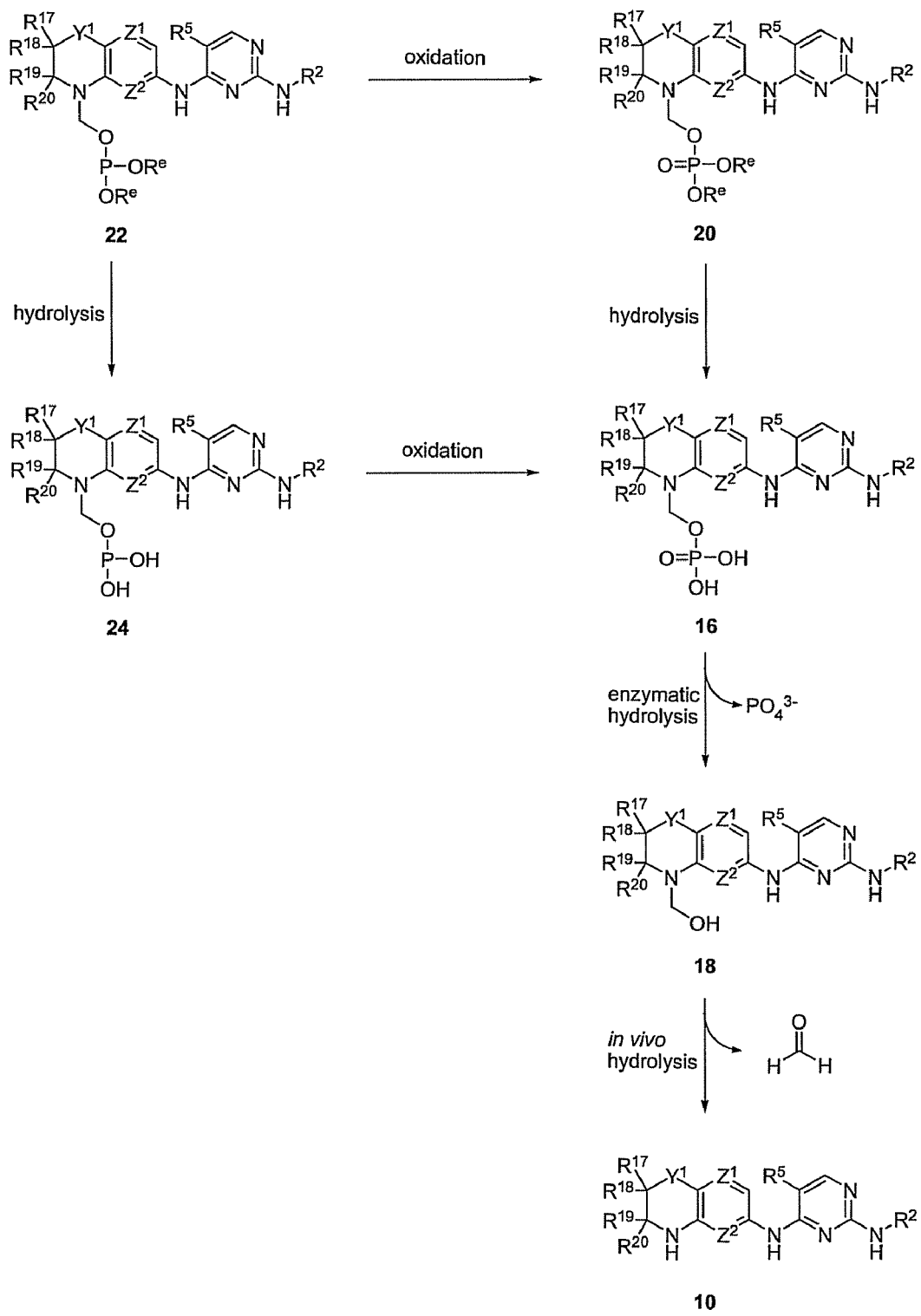
Figure 13B:
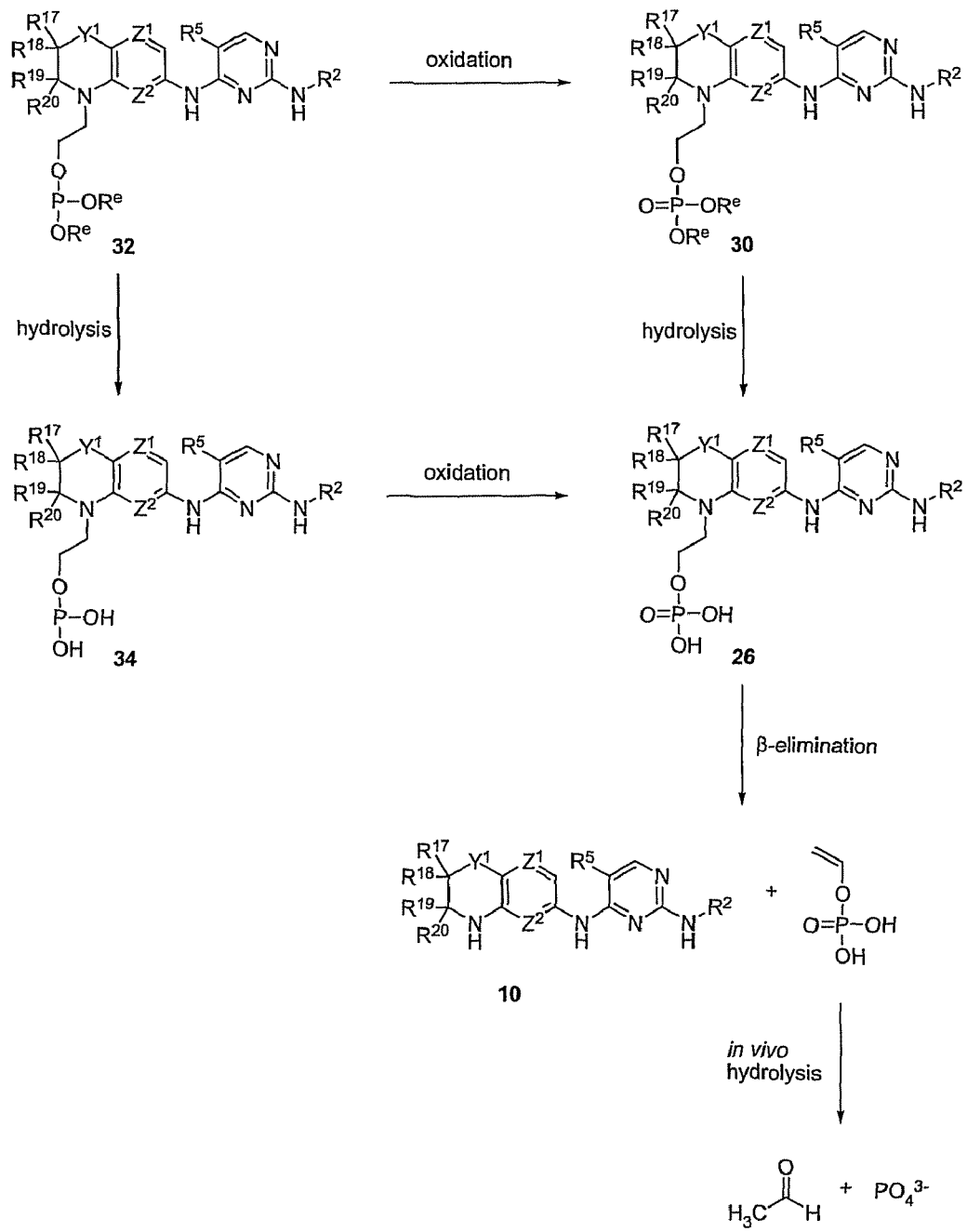
Figure 14:
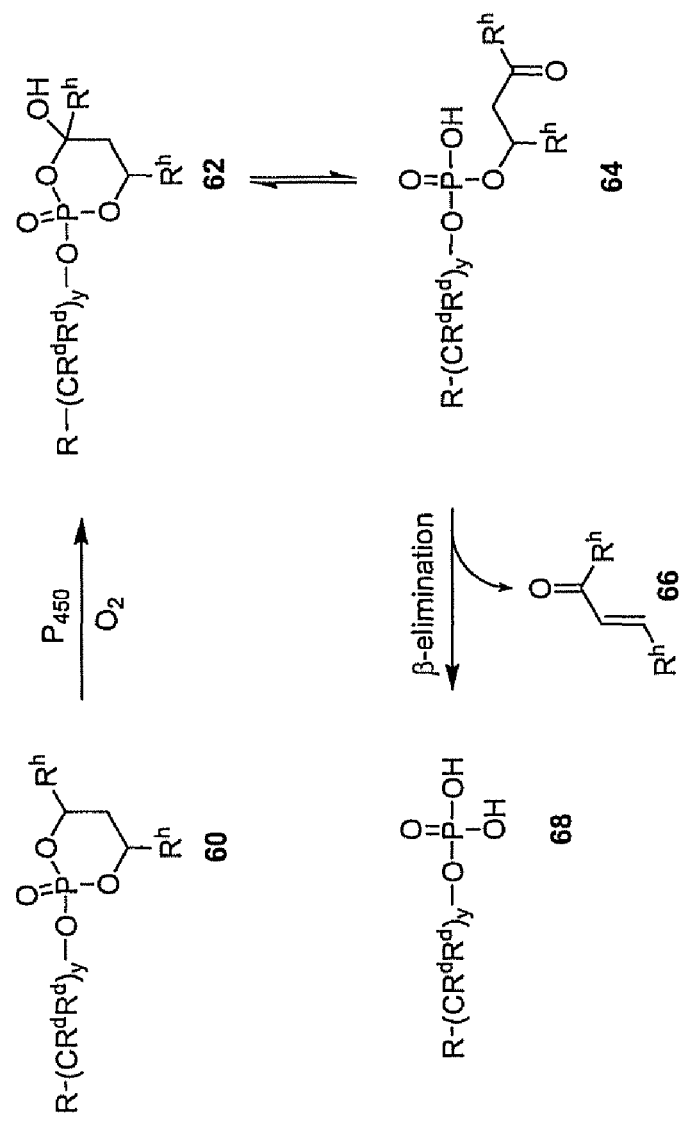
Figure 15:
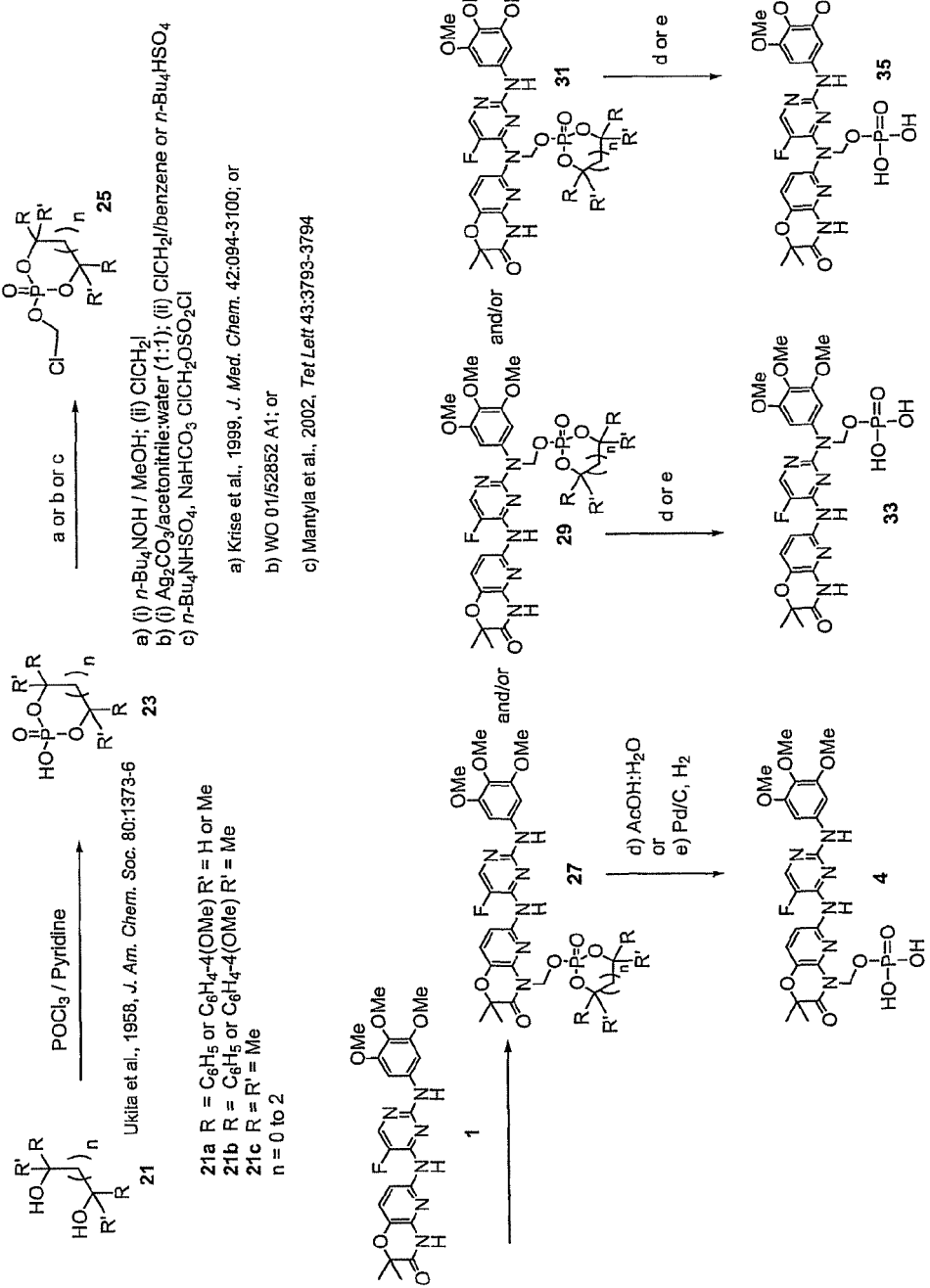

FIGS. 13A and 13B provide schemes illustrating metabolic pathways of exemplary phosphorous-containing prodrugs;

FIG. 14 provides a scheme illustrating a metabolic pathway of an exemplary cyclic phosphate ester prodrug;

FIG. 15 illustrates an exemplary synthesis of exemplary cyclic phosphate prodrug; and FIGS. 16-23 provide graphs illustrating various pharmacokinetic data for drug Compound III and/or prodrug Compound 4.

6. DETAILED DESCRIPTION OF EMBODIMENTS

6.1 Methods of Treatment

The present disclosure provides method of treating cell proliferative disorders by administration of Syk kinase or Syk/Flt-3 kinase inhibitory compounds. Syk kinase is one of the two known members of the Syk family (Syk and ZAP-70) non-receptor tyrosine kinases. Syk is activated upon the binding of its src homology 2 (SH2) domains to immunoreceptor tyrosine-based activation motifs (ITAM). Syk kinase plays an essential role in lymphocyte development and activation of immune cells and is best characterized for its role in B cell receptor signaling and Fc receptor mediated release of mast cell granules. Although expressed ubiquitously in hematopoietic cells, Syk is also expressed in other tissues, such as breast epithelial cells and hepatocytes. It is believed by some in the field that Syk is a tumor suppressor and acts as a negative regulator of metastatic potential. Loss of Syk activity is suggested as being associated with formation of invasive breast cancer, and chromosomal loss of the Syk gene is indicated in certain types of lymph node metastasis of primary breast cancer. Thus, use of Syk inhibitors to treat cell proliferative disorders or as treatment to reduce the metastatic potential of tumor cells would be contraindicated if Syk functions as a tumor suppressor.

Flt-3 is also a tyrosine kinase, but unlike Syk, it belongs to the family of tyrosine kinase receptor proteins. Flt-3 is a member of the class III receptor tyrosine kinases, which are related by amino acid sequence and structural characteristics. Flt-3 is activated by binding to its cognate ligand, Flt-3 L. Flt-3 kinase is expressed in early hematopoietic stem cells of normal bone marrow, and appears to function in the development of multipotent stem cells and B cells by controlling the activity of various downstream cellular targets that include, among others, phospholipase C-(PLC), the p85 subunit of phosphatidylinositol 3'-kinase (P13K), Shc, Shp-2, Ship, Grb2, Vav, Fyn kinase, Src kinase, Stat5 signal transducing protein, and Erk. Although Flt-3 kinase is normally expressed in progenitor cells in the bone marrow, high levels of expression are also observed in a spectrum of hematologic cell proliferative disorders, such as acute myelogenous leukemia (AML), B-precursor cell acute lymphoblastic leukemia, T-cell acute lymphoblastic leukemia, and chronic myelogenous leukemia (CML) in lymphoid blast crisis (see. e.g., Rosnet et al., 1996, *Leukemia* 10:238-248; Carow et al., 1996, *Blood* 87:1089-1096). Presence of Flt-3 mutations in hematological cell proliferative disorders correlates with decreased remission rates, increases in relapse rates, and generally lower overall survival rates (Rombouts et al., 2000, *Leukemia* 14:675-683; Thiede et al., 2002, *Blood* 99:4326-4335; Frohling et al., 2002, *Blood* 100:4372-4380).

Although the art suggests that Syk may act as a tumor suppressor, the present disclosure is based on indications that Syk functions contrary to that posited role. For instance, forced expression of Syk kinase in tumor cells does not appear to reverse the transformed phenotype of tumor cells. To the contrary, it is suggested herein that Syk acts in an oncogenic capacity to promote and/or maintain cell proliferation. With this perspective on the role of Syk, the disclosure provides methods of treating cell proliferative disorders by administering to a subject an amount of a Syk kinase inhibitory compound effective to treat a cell proliferative disorder.

Moreover, it is shown herein that some Syk inhibitory compounds, such as members of the 2,4-pyrimidinediamine compounds described in further detail below, can also act as inhibitors of the Flt-3 kinase. Consequently, in some embodiments, Syk inhibitory compounds with this dual- or multi-acting inhibitory profile of inhibiting Flt-3 kinase as well as Syk kinase (i.e., Syk/Flt-3 kinase inhibitory activities) find applications for treatment of cell proliferative disorders associated with aberrant Flt-3 receptor kinase activity. The association of both Syk kinase and Flt-3 kinase with the development of hematopoietic cells supports the use of such Syk/Flt-3 kinase inhibitory compounds for treatment of hematopoietic neoplasms.

In the descriptions of the methods herein, the terms used will have their ordinary and common meaning, unless specifically defined otherwise herein.

"Syk" or "Syk kinase" refers to the 72kDa non-receptor (cytoplasmic) spleen protein tyrosine kinase expressed in B-cells and other hematopoetic cells. Syk kinase is characterized by two consensus Src-homology 2 (SH2) domains in tandem that bind to phosphorylated immunoreceptor tyrosine-based activation motifs ("ITAMs"), a "linker" domain and a catalytic domain (for a review, see Sada et al., 2001, *J. Biochem. (Tokyo)* 130:177-186 and also Turner et al., 2000, *Immunology Today* 21:148-154 and Wong et al., 2004, *Expert Opin Investig Drugs* 13(7):743-62.). Syk kinase is also critical for tyrosine phosphorylation of multiple proteins which regulate important pathways leading from immunoreceptors, such as $Ca^{2+}$ mobilization and mitogen-activated protein kinase (MAPK) cascades and degranulation. Syk kinase also plays a critical role in integrin signaling in neutrophils (see, e.g., Mocsai et al. 2002, *Immunity* 16:547-558). Syk kinase includes kinases from any species of animal, including but not limited to, homo sapiens, simian, bovine, porcine, rodent, etc., recognized as belonging to the Syk family. Specifically included are isoforms, splice variants, allelic variants, mutants, both naturally occurring and man-made. The amino acid sequences of such Syk kinases are available from GENBANK. Specific examples of mRNAs encoding different isoforms of human Syk kinase are available at GENBANK accession no. gi|21361552|ref|NM_003177.2, gi|496899|emb|Z29630.1|HSSYKPTK[496899] and gi|15030258|gb|BC011399.1|BC011399[15030258], which are incorporated herein by reference.

"Flt-3" or "Flt-3 receptor tyrosine kinase" refers to a receptor tyrosine kinase that binds the flt-3 ligand (Flt-3 L or FL). Flt-3 is also knowns as Fms-like tyrosine kinase 3, FLK-2 (fetal liver kinase-2) and STK-1 (human stem cell kinase-11) (see, e.g., Mathews et al., 1991, *Cell.* 65:1143-1152; Rosnet et al., 1991, *Oncogene.* 6:1641-1650). Flt-3 has sequence similarity to members of the class III receptor tyrosine kinase (RTKIII) family, a subset of which includes, among others, FMS, platelet-derived growth factor receptor (PDGFR), and Kit (Rosnet et al., 1993, *Crit Rev Oncog.* 4:595-613. The Flt-3 polypeptide in mouse and human is a 1000- and 993-amino acid protein, respectively, and is known to be expressed in immature hematopoietic cells, placenta, gonads, and brain. As noted above, Flt-3 has a postulated role in the development of multipotent stem cells and B cells. Similar to other members of the class III receptor tyrosine kinases, Flt-3 is characterized by 5 immunoglobulin-like repeats in the extracellular domain, a transmembrane (TM) domain, a juxtamembrane (JM) domain, two intracellular tyrosine kinase (TK1 and TK2) domains separated by a kinase insert (KI) domain, and a C-terminus domain (Agnes et al., 1994, *Gene* 145: 283-288; 2004, Griffith et al., *Molecular Cell* 13:169-178). Flt-3 kinase includes kinases from any species of animal, including but not limited to, homo sapiens, simian, bovine, porcine, rodent, etc., recognized as belonging to the Flt-3 receptor family. Specifically included are isoforms, splice variants, allelic variants, mutants, both naturally occurring and man-made. The amino acid sequences of such Syk kinases are available from GENBANK. Specific examples of nucleic acid sequences and corresponding amino acid sequences of different Flt-3 kinases include, among others, human (Accession Nos. NM_004119.1), chimpanzee (Accession Nos. 452508; XM_509601.1; XP_509601.1), dog (NM_001020811.1; NP_001018647.1), and mouse (Accession Nos. 142551; NM_010229.11; NP_034359.11; AK0458654; AK1492924; AK1636404; BC1090034; BC1090044; L361634; M646894; X593984), which are incorporated herein by reference.

Some embodiments of Flt-3 variants are associated with certain hematopoietic cell proliferative disorders. "Flt-3 ITD" refers to a variant of Flt-3 having internal tandem duplications (ITDs) in the juxtamembrane (JM) domain (Nakao et al., 1996, *Leukemia* 10:1911-1918; Griffith et al., supra). The number of JM domains duplicated in Flt-3 ITD varies from subject to subject but are in-frame and generally results in protein with an aberrant (i.e., increased) tyrosine kinase activity. Variants of the Flt-3 ITD type are often associated with acute myelogenous leukemia and myelodysplastic syndrome. Another type of variant is "Flt-3 activation loop mutations," which refer to variants having an amino sequence change (as compared to wild-type) in the activation loop of the second tyrosine kinase (TK2) domain. Without being bound by theory, the activation loop appears to function in blocking access of adenosine triphosphate (ATP) and substrate to the kinase domain, and thereby exerts an inhibitory effect on the kinase. As a consequences, activation loop mutations can give rise to Flt-3 kinase forms with constitutive activity. An exemplary activation loop variant is D835A, which is observed in acute myelogenous leukemia, myelodysplatic syndrome, and acute lymphoblastic leukemia (Yamamoto et al., 2001, *Blood* 97:2434-2439; Griffin, J. D., 2001, *Blood* 97:2193a). Other exemplary activation loop variations associated with cell proliferative disorders in humans included, among others, D835Y, D835A, D835E, D835H, D835N, D835V, D835del, and 1836del "Cell proliferative disorder" refers to a disorder characterized by abnormal proliferation of cells. A proliferative disorder does not imply any limitation with respect to the rate of cell growth, but merely indicates loss of normal controls that affect growth and cell division. Thus, in some embodiments, cells of a proliferative disorder can have the same cell division rates as normal cells but do not respond to signals that limit such growth. Within the ambit of "cell proliferative disorder" is neoplasm or tumor, which is an abnormal growth of tissue. Cancer refers to any of various malignant neoplasms characterized by the proliferation of cells that have the capability to invade surrounding tissue and/or metastasize to new colonization sites.

"Hematopoietic neoplasm" refers to a cell proliferative disorder arising from cells of the hematopoietic lineage. Generally, hematopoiesis is the physiological process whereby undifferentiated cells or stem cells develop into various cells found in the peripheral blood. In the initial phase of development, hematopoietic stem cells, typically found in the bone marrow, undergo a series of cell divisions to form multipotent progenitor cells that commit to two main developmental pathways: the lymphoid lineage and the myeloid lineage. The committed progenitor cells of the myeloid lineage differentiate into three major sub-branches comprised of the erythroid, megakaryocyte, and granulocyte/monocyte developmental pathways. An additional pathway leads to formation of dendritic cells, which are involved in antigen presentation. The erythroid lineage gives rise to red blood cells while the megakaryocytic lineage gives rise to blood platelets. Committed cells of the granulocyte/monocyte lineage split into granulocyte or monocyte developmental pathways, the former pathway leading to formation of neutrophils, eosinophils, and basophils and the latter pathway giving rise to blood monocytes and macrophages.

Committed progenitor cells of the lymphoid lineage develop into the B cell pathway, T cell pathway, or the non-T/B cell pathway. Similar to the myeloid lineage, an additional lymphoid pathway appears to give rise to dendritic cells involved in antigen presentation. The B cell progenitor cell develops into a precursor B cell (pre-B), which differentiates into B cells responsible for producing immunoglobulins. Progenitor cells of the T cell lineage differentiate into precursor T cells (pre-T) that, based on the influence of certain cytokines, develop into cytotoxic or helper/suppressor T cells involved in cell mediated immunity. Non-T/B cell pathway leads to generation of natural killer (NK) cells. Neoplasms of hematopoietic cells can involve cells of any phase of hematopoiesis, including hematopoietic stem cells, multipotent progenitor cells, oligopotent committed progenitor cells, precursor cells, and mature differentiated cells. The categories of hematopoietic neoplasms can generally follow the descriptions and diagnostic criteria employed by those of skill in the art (see, e.g., International Classification of Disease and Related Health Problems (ICD 10), World Health Organization (2003)). Hematopoietic neoplasms can also be characterized based on the molecular features, such as cell surface markers and gene expression profiles, cell phenotype exhibited by the aberrant cells, and/or chromosomal aberrations (e.g., deletions, translocations, insertions, etc.) characteristic of certain hematopoietic neoplasms, such as the Philadelphia chromosome found in chronic myelogenous leukemia. Other classifications include National Cancer Institute Working Formulation (Cancer, 1982, 49:2112-2135) and Revised European-American Lymphoma Classification (REAL).

"Lymphoid neoplasm" refers a proliferative disorder involving cells of the lymphoid lineage of hematopoiesis. Lymphoid neoplasms can arise from hematopoietic stem cells as well as lymphoid committed progenitor cells, precursor cells, and terminally differentiated cells. These neoplasms can be subdivided based on the phenotypic attributes of the aberrant cells or the differentiated state from which the abnormal cells arise. Subdivisions include, among others, B cell neoplasms, T cell neoplasms, NK cell neoplasms, and Hodgkin's lymphoma.

"Myeloid neoplasm" refers to proliferative disorder of cells of the myeloid lineage of hematopoiesis. Neoplasms can arise from hematopoietic stem cells, myeloid committed progenitor cells, precursor cells, and terminally differentiated cells. Myeloid neoplasms can be subdivided based on the phenotypic attributes of the aberrant cells or the differentiated state from which the abnormal cells arise. Subdivisions include, among others, myeloproliferative diseases, myelodysplastic/myeloproliferative diseases, myelodysplastic syndromes, acute myeloid leukemia, and acute biphenotypic leukemia.

"Virally mediated tumor" refers to a neoplasm or tumor associated with viral infection or an activity of a virally encoded product. The neoplasm can arise from presence of a latent virus integrated into the cellular genome or arise from activity of a virally associated gene product. Infection with the virus need not be tightly correlated in time with tumor formation in that incubation periods can extend from months to years before development of a tumor phenotype. Because the treatments herein are directed to use of Syk inhibitors, the applicable virally associated tumors are those in which viral modulation of Syk activity is correlated with aberrant cell proliferation. Any virus, including RNA and DNA viruses and viruses that reside episomally or integrate into the cellular genome, in which activation of Syk is a consequence of virus infection can be targeted using the methods herein.

"Tumor metastasis" refers to the capability of tumor cells to migrate from the original tumor site and colonize in other tissues. Tumors formed from cells that have spread are referred to as "secondary tumors" and contain cells that are similar to those in the original "primary" tumor. Metastatic tumors typically form by migration of tumor cells from the original tumor site through the blood and lymph system to other tissues.

"Syk mediated integrin signaling" refers to signal transduction of cell surface integrins that occur via interaction with Syk kinase. Integrins comprise an extended family of cell surface adhesion receptors that bind extracellular matrix and cell surface ligands. Structurally, integrins are heterodimeric proteins composed of an α and β chain, where each subunit has an extracellular domain, a single transmembrane domain, and a cytoplasmic domain. The α subunit generally composed of about seven tandem repeats, where a subset of the repeats contain putative metal binding sequences of the general structure DxDxDGxxD, where x is any amino acid. Two groups of integrins can be characterize by the α subunits: those that contain an "A" domain and those having a proteolytic cleavage site. The β subunit comprises a conserved region of about 200 amino acids in the extracellular domain, which is characterized by a region having structural similarity to the "A" domain of the a subunit and another region with epidermal growth factor (EGF) like repeats, similar to those found in laminin (see, e.g., Xiong et al., 2003, *Blood,* 102(4): 1155-1159). Integrin activity may modulate intracellular Syk, or conversely, the integrin function can be modulated via the activity of Syk. It is generally understood that in some instances, integrins require activation within the cell to bind its cognate ligands (inside-out activation). Integrins that either modulate or is modulated by Syk include, among others, β1-integrins (Lin et al., *J Biol. Chem.* 1995, 270(27): 16189-97) such as $\alpha_2 b_1$ (Keely et al., 1996, *J Biol Chem.* 271(43):26668-76), β2 integrins, and β3 integrins (Woodside et al., 2001, *Curr Biol.* 11(22):1799-804) such as $\alpha_{IIb}\beta_3$ (Clark et al., *J. Biol. Chem.* 1994, 269(46):28859-64). For instance, it is believed that Syk binds directly to the integrin $\beta_3$ cytoplasmic tail through the SH2 domains. However, unlike Syk binding to ITAMs, the interaction with β3 integrin appears independent of the phosphotyrosine binding function of the tandem SH2 domains.

"Alkyl" by itself or as part of another substituent refers to a saturated or unsaturated branched, straight-chain or cyclic monovalent hydrocarbon radical having the stated number of carbon atoms (i.e., C1-C6 means one to six carbon atoms) that is derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl," "alkenyl" and/or "alkynyl" is used, as defined below. As used herein, "lower alkyl" means (C1-C8) alkyl.

"Alkanyl" by itself or as part of another substituent refers to a saturated branched, straight-chain or cyclic alkyl derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like. As used herein, "lower alkanyl" means (C1-C8) alkanyl.

"Alkenyl" by itself or as part of another substituent refers to an unsaturated branched, straight-chain or cyclic alkyl having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like. As used herein, "lower alkenyl" means (C2-C8) alkenyl.

"Alkynyl" by itself or as part of another substituent refers to an unsaturated branched, straight-chain or cyclic alkyl having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like. As used herein, "lower alkynyl" means (C2-C8) alkynyl.

"Alkyldiyl" by itself or as part of another substituent refers to a saturated or unsaturated, branched, straight-chain or cyclic divalent hydrocarbon group having the stated number of carbon atoms (i.e., C1-C6 means from one to six carbon atoms) derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to, methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene -propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. Where it is specifically intended that the two valencies are on the same carbon atom, the nomenclature "alkylidene" is used. In some embodiments, the alkyldiyl group is (C1-C8) alkyldiyl. Specific embodiments include saturated acyclic alkanyldiyl groups in which the radical centers are at the terminal carbons, e.g., methandiyl (methano); ethan-1,2-diyl (ethano); propan-1,3-diyl (propano); butan -1,4-diyl (butano); and the like (also referred to as alkylenos, defined infra)

"Alkyleno" by itself or as part of another substituent refers to a straight-chain saturated or unsaturated alkyldiyl group having two terminal monovalent radical centers derived by the removal of one hydrogen atom from each of the two terminal carbon atoms of straight-chain parent alkane, alkene or alkyne. The locant of a double bond or triple bond, if present, in a particular alkyleno is indicated in square brackets. Typical alkyleno groups include, but are not limited to, methano; ethylenos such as ethano, etheno, ethyno; propylenos such as propano, prop[1]eno, propa[1,2]dieno, prop[1]yno, etc.; butylenos such as butano, but[1]eno, but[2]eno, buta[1,3]dieno, but[1]yno, but[2]yno, buta[1,3]diyno, etc.; and the like. Where specific levels of saturation are intended, the nomenclature alkano, alkeno and/or alkyno is used. In some embodiments, the alkyleno group is (C1-C8) or (C1-C3) alkyleno. Specific embodiments include straight-chain saturated alkano groups, e.g., methano, ethano, propano, butano, and the like.

"Heteroalkyl," Heteroalkanyl, "Heteroalkenyl," Heteroalkynyl, "Heteroalkyldiyl" and "Heteroalkyleno" by themselves or as part of another substituent refer to alkyl, alkanyl, alkenyl, alkynyl, alkyldiyl and alkyleno groups, respectively, in which one or more of the carbon atoms are each independently replaced with the same or different heteroatoms or heteroatomic groups. Typical heteroatoms and/or heteroatomic groups which can replace the carbon atoms include, but are not limited to, —O—, —S—, —S—O—, —NR'—, —PH—, —S(O)—, —S(O)$_2$—, —S(O)NR'—, —S(O)$_2$NR'—, and the like, including combinations thereof, where each R' is independently hydrogen or (C1-C8) alkyl.

"Cycloalkyl" and "Heterocycloalkyl" by themselves or as part of another substituent refer to cyclic versions of "alkyl" and "heteroalkyl" groups, respectively. For heteroalkyl groups, a heteroatom can occupy the position that is attached to the remainder of the molecule. Typical cycloalkyl groups include, but are not limited to, cyclopropyl; cyclobutyls such as cyclobutanyl and cyclobutenyl; cyclopentyls such as cyclopentanyl and cyclopentenyl; cyclohexyls such as cyclohexanyl and cyclohexenyl; and the like. Typical heterocycloalkyl groups include, but are not limited to, tetrahydrofuranyl (e.g., tetrahydrofuran-2-yl, tetrahydrofuran-3-yl, etc.), piperidinyl (e.g., piperidin-1-yl, piperidin-2-yl, etc.), morpholinyl (e.g., morpholin-3-yl, morpholin-4-yl, etc.), piperazinyl (e.g., piperazin-1-yl, piperazin-2-yl, etc.), and the like.

"Acyclic Heteroatomic Bridge" refers to a divalent bridge in which the backbone atoms are exclusively heteroatoms and/or heteroatomic groups. Typical acyclic heteroatomic bridges include, but are not limited to, —O—, —S—, —S—O—, —NR'—, —PH—, —S(O)—, —S(O)$_2$—, —S(O)NR'—, —S(O)$_2$NR'—, and the like, including combinations thereof, where each R' is independently hydrogen or (C1-C8) alkyl.

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, tetrahydronaphthalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, tetrahydronaphthalene, triphenylene, trinaphthalene, and the like.

"Aryl" by itself or as part of another substituent refers to a monovalent aromatic hydrocarbon group having the stated number of carbon atoms (i.e., C6-C15 means from 6 to 15 carbon atoms) derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, pentacene, pentalene, pentaphene, perylene, phenalene, phenanthrene, picene, pleiadene, pyrene, pyranthrene, rubicene, triphenylene, trinaphthalene, and the like, as well as the various hydro isomers thereof. In preferred embodiments, the aryl group is (C6-C15) aryl, with (C6-C10) being more typical. Specific exemplary aryls include phenyl and naphthyl.

"Arylaryl" by itself or as part of another substituent refers to a monovalent hydrocarbon group derived by the removal of one hydrogen atom from a single carbon atom of a ring system in which two or more identical or non-identical parent aromatic ring systems are joined directly together by a single bond, where the number of such direct ring junctions is one less than the number of parent aromatic ring systems involved. Typical arylaryl groups include, but are not limited to, biphenyl, triphenyl, phenyl-naphthyl, binaphthyl, biphenyl-naphthyl, and the like. Where the number of carbon atoms in an arylaryl group are specified, the numbers refer to the carbon atoms comprising each parent aromatic ring. For example, (C6-C15) arylaryl is an arylaryl group in which each aromatic ring comprises from 6 to 15 carbons, e.g., biphenyl, triphenyl, binaphthyl, phenylnaphthyl, etc. In some embodiments, each parent aromatic ring system of an arylaryl group is independently a (C6-C15) aromatic, more preferably a (C6-C10) aromatic. Specific exemplary arylaryl groups include those in which all of the parent aromatic ring systems are identical, e.g., biphenyl, triphenyl, binaphthyl, trinaphthyl, etc.

"Biaryl" by itself or as part of another substituent refers to an arylaryl group having two identical parent aromatic systems joined directly together by a single bond. Typical biaryl groups include, but are not limited to, biphenyl, binaphthyl, bianthracyl, and the like. In some embodiments, the aromatic ring systems are (C6-C15) aromatic rings, more typically (C6-C10) aromatic rings. A particular exemplary biaryl group is biphenyl.

"Arylalkyl" by itself or as part of another substituent refers to an acyclic alkyl group in which one of the hydrogen atoms bonded to a carbon atom, typically a terminal or sp.sup.3 carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylakenyl and/or arylalkynyl is used. In some embodiments, the arylalkyl group is (C7-C21) arylalkyl, e.g., the alkanyl, alkenyl or alkynyl moiety of the arylalkyl group is (C1-C6) and the aryl moiety is (C6-C15). In some specific embodiments the arylalkyl group is (C7-C13), e.g., the alkanyl, alkenyl or alkynyl moiety of the arylalkyl group is (C1-C3) and the aryl moiety is (C6-C10).

"Parent Heteroaromatic Ring System" refers to a parent aromatic ring system in which one or more carbon atoms are each independently replaced with the same or different heteroatoms or heteroatomic groups. Typical heteroatoms or heteroatomic groups to replace the carbon atoms include, but are not limited to, N, NH, P, O, S, S(O), S(O)$_2$, Si, etc. Specifically included within the definition of "parent heteroaromatic ring systems" are fused ring systems in which one or more of the rings are aromatic and one or more of the rings are saturated or unsaturated, such as, for example, benzodioxan, benzofuran, chromane, chromene, indole, indoline, xanthene, etc. Also included in the definition of "parent heteroaromatic ring system" are those recognized rings that include common substituents, such as, for example, benzopyrone and 1-methyl-1,2,3,4-tetrazole. Specifically excluded from the definition of "parent heteroaromatic ring system" are benzene rings fused to cyclic polyalkylene glycols such as cyclic polyethylene glycols. Typical parent heteroaromatic ring systems include, but are not limited to, acridine, benzimidazole, benzisoxazole, benzodioxan, benzodioxole, benzofuran, benzopyrone, benzothiadiazole, benzothiazole, benzotriazole, benzoxaxine, benzoxazole, benzoxazoline, carbazole, .beta.-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Heteroaryl" by itself or as part of another substituent refers to a monovalent heteroaromatic group having the stated number of ring atoms (e.g., "5-14 membered" means from 5 to 14 ring atoms) derived by the removal of one hydrogen atom from a single atom of a parent heteroaromatic ring system. Typical heteroaryl groups include, but are not limited to, groups derived from acridine, benzimidazole, benzisoxazole, benzodioxan, benzodiaxole, benzofuiran, benzopyrone, benzothiadiazole, benzothiazole, benzotriazole, benzoxaxine, benzoxazole, benzoxazoline, carbazole, .beta.-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like, as well as the various hydro isomers thereof. In preferred embodiments, the heteroaryl group is a 5-14 membered heteroaryl, with 5-10 membered heteroaryl being particularly preferred.

"Heteroaryl-Heteroaryl" by itself or as part of another substituent refers to a monovalent heteroaromatic group derived by the removal of one hydrogen atom from a single atom of a ring system in which two or more identical or non-identical parent heteroaromatic ring systems are joined directly together by a single bond, where the number of such direct ring junctions is one less than the number of parent heteroaromatic ring systems involved. Typical heteroaryl-heteroaryl groups include, but are not limited to, bipyridyl, tripyridyl, pyridylpurinyl, bipurinyl, etc. Where the number of atoms are specified, the numbers refer to the number of atoms comprising each parent heteroaromatic ring systems. For example, 5-15 membered heteroaryl-heteroaryl is a heteroaryl-heteroaryl group in which each parent heteroaromatic ring system comprises from 5 to 15 atoms, e.g., bipyridyl, tripuridyl, etc. In some embodiments, each parent heteroaromatic ring system is independently a 5-15 membered heteroaromatic, more typically a 5-10 membered heteroaromatic. Specific exemplary heteroaryl-heteroaryl groups include those in which all of the parent heteroaromatic ring systems are identical.

"Biheteroaryl" by itself or as part of another substituent refers to a heteroaryl-heteroaryl group having two identical parent heteroaromatic ring systems joined directly together by a single bond. Typical biheteroaryl groups include, but are not limited to, bipyridyl, bipurinyl, biquinolinyl, and the like. In some embodiments, the heteroaromatic ring systems are 5-15 membered heteroaromatic rings, more typically 5-10 membered heteroaromatic rings.

"Heteroarylalkyl" by itself or as part of another substituent refers to an acyclic alkyl group in which one of the hydrogen atoms bonded to a carbon atom, typically a terminal or sp.sup.3 carbon atom, is replaced with a heteroaryl group. Where specific alkyl moieties are intended, the nomenclature heteroarylalkanyl, heteroarylakenyl and/or heteroarylalkynyl is used. In some embodiments, the heteroarylalkyl group is a 6-21 membered heteroarylalkyl, e.g., the alkanyl, alkenyl or alkynyl moiety of the heteroarylalkyl is (C1-C6) alkyl and the heteroaryl moiety is a 5-15-membered heteroaryl. In some specific exemplary embodiments, the heteroarylalkyl is a 6-13 membered heteroarylalkyl, e.g., the alkanyl, alkenyl or alkynyl moiety is (C1-C3) alkyl and the heteroaryl moiety is a 5-10 membered heteroaryl.

"Halogen" or "Halo" by themselves or as part of another substituent, unless otherwise stated, refer to fluoro, chloro, bromo and iodo.

"Haloalkyl" by itself or as part of another substituent refers to an alkyl group in which one or more of the hydrogen atoms is replaced with a halogen. Thus, the term "haloalkyl" is meant to include monohaloalkyls, dihaloalkyls, trihaloalkyls, etc. up to perhaloalkyls. For example, the expression "(C1-C2) haloalkyl" includes fluoromethyl, difluoromethyl, trifluoromethyl, 1-fluoroethyl, 1,1-difluoroethyl, 1,2-difluoroethyl, 1,1,1-trifluoroethyl, perfluoroethyl, etc.

The above-defined groups may include prefixes and/or suffixes that are commonly used in the art to create additional well-recognized substituent groups. As examples, "alkyloxy" or "alkoxy" refers to a group of the formula —OR", "alkylamine" refers to a group of the formula —NHR" and "dialkylamine" refers to a group of the formula —NR"R", where each R" is independently an alkyl. As another example, "haloalkoxy" or "haloalkyloxy" refers to a group of the formula —OR''', where R''' is a haloalkyl.

"Substituted," when used to modify a specified group or radical, means that one or more hydrogen atoms of the specified group or radical are each, independently of one another, replaced with the same or different substituent(s). Substituent groups useful for substituting for hydrogens on saturated carbon atoms in the specified group or radical include, but are not limited to —$R^{60}$, halo, —$O^-M^+$, =O, —$OR^{70}$, —$SR^{70}$, —$S^{-M30}$, =S, —$NR^{80}R^{80}$, =$NR^{70}$, =N—$OR^{70}$, trihalomethyl, —$CF_3$, —CN, —OCN, —SCN, —NO, —$NO_2$, =$N_2$, —$N_3$, —$S(O)_2R^{70}$, —$S(O)_2O^-M^+$, —$S(O)_2OR^{70}$, —$OS(O)_2R.sup.7$, —$OS(O)_2O^-M^+$, —$OS(O)_2OR^{70}$, —$P(O)(O^-)_2(M^+)_2$, —$P(O)(OR^{70}O^-M^+$, —$P(O)(OR^{70})(OR^{70})$, —$C(O)R^{70}$, —$C(S)R^{70}$, —$C(NR^{70})R^{70}$, —$C(O)O^-M^+$, —$C(O)OR^{70}$, —$C(S)OR^{70}$, —$C(O)NR^{80}R^{80}$, —$C(NR^{70})NR^{80}R^{80}$, —$OC(O)R^{70}$, —OC $(O)O^-M^+$, —$OC(O)OR^{70}$, —$OC(S)OR^{70}$, —$NR^{70}C(O)R^{70}$, —$NR^{70}C(S)R^{70}$, —$NR^{70}C(O)O^-M^+$, —$NR^{70}C(O)OR^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$ is selected from the group consisting of alkyl, cycloalkyl, heteroalkyl, cycloheteroalkyl, aryl, arylalkyl, heteroaryl and heteroarylalkyl; each $R^{70}$ is independently hydrogen or $R^{60}$; each $R^{80}$ is independently $R^{70}$ or alternatively, the two $R^{80}$s, taken together with the nitrogen atom to which they are bonded, form a 5-, 6- or 7-membered cycloheteroalkyl which may optionally include from 1 to 4 of the same or different additional heteroatoms selected from the group consisting of O, N and S; and each $M^+$ is a counter ion with a positive charge, for example, a positive charge independently selected from $K^+$, $Na^+$, $^+N(R^{60})_4$, and $Li^+$, or two of $M^+$, combine to form a divalent counterion, for example a divalent counterion selected from $Ca^{2+}$, $Mg^{2+}$, and $Ba^{2+}$. As specific examples, —$NR^{80}R^{80}$ is meant to include —$NH_2$, —NH-alkyl, N-pyrrolidinyl and N-morpholinyl.

Similarly, substituent groups useful for substituting for hydrogens on unsaturated carbon atoms in the specified group or radical include, but are not limited to, —$R^{60}$, halo, —$O^-M^+$, —$OR^{70}$, —$SR^{70}$, —$S^-M^+$, —$NR^{80}R^{80}$, trihalomethyl, —$CF_3$, —CN, —OCN, —SCN, —NO, —$NO_2$, —$N_3$, —$S(O)_2R^{70}$, —$S(O)_2O^-M^+$, —$S(O)_2OR^{70}$, —$OS(O)_2R^{70}$, —$OS(O)_2O^-M^+$, —$OS(O)_2OR^{70}$, —$P(O)(O^-)_2(M^+)_2$, —$P(O)(OR^{70})O^-M^+$, —$P(O)(OR^{70})(OR^{70})$, —$C(O)R^{70}$, —$C(S)R^{70}$, —$C(NR^{70})R^{70}$, —$C(O)O-M^+$, —$C(O)OR^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OC(O)O^-M^+$, —$OC(O)OR^{70}$, —$OC(S)OR^{70}$, —$NR^{70}C(O)R^{70}$, —$NR^{70}C(S)R^{70}$, —$NR^{70}C(O)O^-M^+$, —$NR^{70}C(O)OR^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$, $R^{70}$, $R^{80}$ and $M^+$ are as previously defined.

Substituent groups useful for substituting for hydrogens on nitrogen atoms in heteroalkyl and cycloheteroalkyl groups include, but are not limited to, —$R^{60}$, —$O^-M^+$, —$OR^{70}$, —$SR^{70}$, —$S^-M^+$, —$NR^{80}R^{80}$, trihalomethyl, —$CF_3$, —CN, —NO, —$NO_2$, —$S(O)_2R^{70}$, —$S(O)_2O^-M^+$, —$S(O)_2OR^{70}$, —$OS(O)_2R^{70}$, —$OS(O)_2O^-M^+$, —$OS(O)_2OR^{70}$, —$P(O)(O^-)_2(M^+)_2$, —$P(O)(OR^{70})O^-M^+$, —$P(O)(OR^{70})(OR^{70})$, —$C(O)R^{70}$, —$C(S)R^{70}$, —$C(NR^{70})R^{70}$, —$C(O)OR^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OC(O)OR^{70}$, —$OC(S)OR^{70}$, —$NR^{70}C(O)R^{70}$, —$NR^{70}C(S)R^{70}$, —$NR^{70}C(O)OR^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$, $R^{70}$, $R^{80}$ and $M^+$ are as previously defined.

Substituent groups from the above lists useful for substituting other groups or atoms specified as "substituted" will be apparent to those of skill in the art.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, Protective Groups in Organic Chemistry, 3rd Ed., 1999, John Wiley & Sons, NY and Harrison et al., Compendium of Synthetic Organic Methods, Vols. 1-8, 1971-1996, John Wiley & Sons, NY. Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated or alkylated such as benzyl and trityl ethers, as well as alkyl ethers, tetrahydropyranyl ethers, trialkylsilyl ethers (e.g., TMS or TIPPS groups) and allyl ethers.

Generally, cell proliferative disorders treatable with the compounds disclosed herein relate to any disorder characterized by aberrant cell proliferation. These include various tumors and cancers, benign or malignant, metastatic or non-metastatic. Specific properties of cancers, such as tissue invasiveness or metastasis, can be targeted using the methods described herein. Cell proliferative disorders include a variety of cancers, including, among others, breast cancer, ovarian cancer, renal cancer, gastrointestinal cancer, kidney cancer, bladder cancer, pancreatic cancer, lung squamous carcinoma, and adenocarcinoma.

In some embodiments, the cell proliferative disorder treated is a hematopoietic neoplasm, which is aberrant growth of cells of the hematopoietic system. Hematopoietic malignancies can have its origins in pluripotent stem cells, multipotent progenitor cells, oligopotent committed progenitor cells, precursor cells, and terminally differentiated cells involved in hematopoiesis. Some hematological malignancies are believed to arise from hematopoietic stem cells, which have the ability for self renewal. For instance, cells capable of developing specific subtypes of acute myeloid leukemia (AML) upon transplantation display the cell surface markers of hematopoietic stem cells, implicating hematopoietic stem cells as the source of leukemic cells. Blast cells that do not have a cell marker characteristic of hematopoietic stem cells appear to be incapable of establishing tumors upon transplantation (Blaire et al., 1997, *Blood* 89:3104-3112). The stem cell origin of certain hematological malignancies also finds support in the observation that specific chromosomal abnormalities associated with particular types of leukemia can be found in normal cells of hematopoietic lineage as well as leukemic blast cells. For instance, the reciprocal translocation t(9q34;22q11) associated with approximately 95% of chronic myelogenous leukemia appears to be present in cells of the myeloid, erythroid, and lymphoid lineage, suggesting that the chromosomal aberration originates in hematopoietic stem cells. A subgroup of cells in certain types of CML displays the cell marker phenotype of hematopoietic stem cells.

Although hematopoietic neoplasms often originate from stem cells, committed progenitor cells or more terminally differentiated cells of a developmental lineage can also be the source of some leukemias. For example, forced expression of the fusion protein Bcr/Abl (associated with chronic myelogenous leukemia) in common myeloid progenitor or granulocyte/macrophage progenitor cells produces a leukemic-like condition. Moreover, some chromosomal aberrations associated with subtypes of leukemia are not found in the cell population with a marker phenotype of hematopoietic stem cells, but are found in a cell population displaying markers of a more differentiated state of the hematopoietic pathway (Turhan et al., 1995, *Blood* 85:2154-2161). Thus, while committed progenitor cells and other differentiated cells may have only a limited potential for cell division, leukemic cells may have acquired the ability to grow unregulated, in some instances mimicking the self-renewal characteristics of hematopoietic stem cells (Passegue et al., *Proc. Natl. Acad. Sci. USA,* 2003, 100:11842-9).

In some embodiments, the hematopoietic neoplasm treated is a lymphoid neoplasm, where the abnormal cells are derived from and/or display the characteristic phenotype of cells of the lymphoid lineage. Lymphoid neoplasms can be subdivided into B-cell neoplasms, T and NK-cell neoplasms, and Hodgkin's lymphoma. B-cell neoplasms can be further subdivided into precursor B-cell neoplasm and mature/peripheral B-cell neoplasm. Exemplary B-cell neoplasms are precursor B-lymphoblastic leukemia/lymphoma (precursor B-cell acute lymphoblastic leukemia) while exemplary mature/peripheral B-cell neoplasms are B-cell chronic lymphocytic leukemia/small lymphocytic lymphoma, B-cell prolymphocytic leukemia, lymphoplasmacytic lymphoma, splenic marginal zone B-cell lymphoma, hairy cell leukemia, plasma cell myeloma/plasmacytoma, extranodal marginal zone B-cell lymphoma of MALT type, nodal marginal zone B-cell lymphoma, follicular lymphoma, mantle-cell lymphoma, diffuse large B-cell lymphoma, mediastinal large B-cell lymphoma, primary effusion lymphoma, and Burkitt's lymphoma/Burkitt cell leukemia. T-cell and Nk-cell neoplasms are further subdivided into precursor T-cell neoplasm and mature (peripheral) T-cell neoplasms. Exemplary precursor T-cell neoplasm is precursor T-lymphoblastic lymphoma/leukemia (precursor T-cell acute lymphoblastic leukemia) while exemplary mature (peripheral) T-cell neoplasms are T-cell prolymphocytic leukemia T-cell granular lymphocytic leukemia, aggressive NK-cell leukemia, adult T-cell lymphoma/leukemia (HTLV-1), extranodal NK/T-cell lymphoma, nasal type, enteropathy-type T-cell lymphoma, hepatosplenic gamma-delta T-cell lymphoma, subcutaneous panniculitis-like T-cell lymphoma, Mycosis fungoides/Sezary syndrome, Anaplastic large-cell lymphoma, T/null cell, primary cutaneous type, Peripheral T-cell lymphoma, not otherwise characterized, Angioimmunoblastic T-cell lymphoma, Anaplastic large-cell lymphoma, T/null cell, primary systemic type. The third member of lymphoid neoplasms is Hodgkin's lymphoma, also referred to as Hodgkin's disease. Exemplary diagnosis of this class that can be treated with the compounds include, among others, nodular lymphocyte-predominant Hodgkin's lymphoma, and various classical forms of Hodgkin's disease, exemplary members of which are Nodular sclerosis Hodgkin's lymphoma (grades 1 and 2), Lymphocyte-rich classical Hodgkin's lymphoma, Mixed cellularity Hodgkin's lymphoma, and Lymphocyte depletion Hodgkin's lymphoma. In various embodiments, any of the lymphoid neoplasms that are associated with aberrant Syk activity can be treated with the Syk inhibitory compounds.

In some embodiments, the hematopoietic neoplasm treated is a myeloid neoplasm. This group comprises a large class of cell proliferative disorders involving or displaying the characteristic phenotype of the cells of the myeloid lineage. Myeloid neoplasms can be subdivided into myeloproliferative diseases, myelodysplastic/myeloproliferative diseases, myelodysplastic syndromes, and acute myeloid leukemias. Exemplary myeloproliferative diseases are chronic myelogenous leukemia (e.g., Philadelphia chromosome positive (t(9; 22)(qq34;q11)), chronic neutrophilic leukemia, chronic eosinophilic leukemialhypereosinophilic syndrome, chronic idiopathic myelofibrosis, polycythemia vera, and essential thrombocythemia. Exemplary myelodysplastic/myeloproliferative diseases are chronic myelomonocytic leukemia, atypical chronic myelogenous leukemia, and juvenile myelomonocytic leukemia. Exemplary myelodysplastic syndromes are refractory anemia, with ringed sideroblasts and without ringed sideroblasts, refractory cytopenia (myelodysplastic syndrome) with multilineage dysplasia, refractory anemia (myelodysplastic syndrome) with excess blasts, 5q-syndrome, and myelodysplastic syndrome with t(9;12) (q22;p12) (TEL-Syk fusion; see, e.g., Kuno et al., 2001, *Blood* 97:1050). In various embodiments, any of the myeloid neoplasms that are associated with aberrant Syk activity can be treated with the Syk inhibitory compounds.

In some embodiments, the Syk inhibitory compounds can be used to treat Acute myeloid leukemias (AML), which represent a large class of myeloid neoplasms having its own subdivision of disorders. These subdivisions include, among others, AMLs with recurrent cytogenetic translocations, AML with multilineage dysplasia, and other AML not otherwise categorized. Exemplary AMLs with recurrent cytogenetic translocations include, among others, AML with t(8;21) (q22;q22), AML1(CBF-alpha)/ETO, Acute promyelocytic leukemia (AML with t(15;17)(q22;q11-12) and variants, PML/RAR-alpha), AML with abnormal bone marrow eosinophils (inv(16)(p13q22) or t(16;16)(p13;q11), CBFb/MYH11X), and AML with 11q23 (MLL) abnormalities. Exemplary AML with multilineage dysplasia are those that are associated with or without prior myelodysplastic syndrome. Other acute myeloid leukemias not classified within any definable group include, AML minimally differentiated, AML without maturation, AML with maturation, Acute myelomonocytic leukemia, Acute monocytic leukemia, Acute erythroid leukemia, Acute megakaryocytic leukemia, Acute basophilic leukemia, and Acute panmyelosis with myelofibrosis.

In other aspects, cell proliferative disorders that can be targeted with the Syk kinase inhibitors comprise virally mediated tumors. These can arise from infection of cells by an oncogenic virus that has the capability of transforming a normal cell into a tumor cell. Because rates of viral infection far exceed the number of actual incidence of cell transformation, viral mediated transformation generally act together with other cellular factors to generate a transformed tumor cell. Thus, a virally mediated tumor does not require the virus to be the sole causative agent of the cell proliferative disorder, but rather that the viral infection or persistent presence of virus is associated with the generation of the tumor. Generally, tumors where the causative agent is a virus typically has continual expression of a limited number of viral genes and that viral these oncogenes, expressed as part of the viral infection or through persistence of the virus, disrupts the normal cellular gene expression and signal transduction pathways. Without being bound by theory, viral oncogenes involved in cell transformation appear to disrupt four main cellular processes: cell surface receptors that interact with growth factors and extracellular matrix, transmembrane signaling networks, cytosolic elements such as soluble proteins and second messengers, and nuclear proteins including DNA binding proteins and factors which function directly and indirectly in gene regulation and replication. Because certain virally encoded proteins target specific cellular components as part of the transformation process, application of Syk inhibitors can be appropriate where the viral component targets the activity of Syk kinase.

In some embodiments, the virally mediated tumor treatable with the compounds disclosed herein is associated with any virus that encodes an immunoreceptor tyrosine-based activation motif (ITAM) capable of modulating Syk activity. This motif, as noted above, refers to a conserved amino acid sequence motif that functions by interacting with and activating nonreceptor tyrosine kinases. ITAM motifs are found in, among others, the p and y chains of FcεRI, the ε subunit of the T cell receptor, and immunoglobulin β (Igβ) and Igα of the B cell receptor. The canonical sequence motif is typically Yxx(L/I)$x_{6-8}$Yxx(L/I), where x represents any amino acid. Generally, the tyrosine residues in the motif are involved in ITAM signaling and are substrates for phosphorylation by Src family of kinases. The phosphorylated form of ITAMs function as interaction sites for SH2 (src homology domain) containing signaling proteins, such as Syk/ZAP-70 kinases. In addition to its presence in a variety of cellular cell surface molecules, the ITAM sequences have been identified in virally encoded proteins. In view of the descriptions herein indicating function of Syk kinase as an oncogene, tumors associated with viruses carrying genes encoding proteins with ITAM sequences can be treated with Syk inhibitor compounds.

Accordingly, in some embodiments, the virally mediated tumor treatable with the inhibitor compounds is associated with Karposi's sarcoma (KS) associated herpes virus, a lymphotropic virus implicated in Karposi's sarcoma, a rare malignancy found at higher incidence among HIV infected population. The KS associated herpes virus encodes a transmembrane protein termed KI having an immunoreceptor tyrosine-based activation motif (ITAM)-like sequence. The KI gene product is thought to act in a constitutive manner through its cysteine-rich ectodomain to activate Syk and its related kinase Zap-70 (Lagunoff, M. et al., 1999, *Proc. Natl. Acad. Sci. USA* 96(10):5704-5709). In further support of the methods herein, transgenic mice bearing the KI gene appears to increase the incidence of certain sarcomas and lymphomas in an infected animal, indicating a role for KI activity in oncogenesis (Prakash et al., 2002, *J. Natl. Cancer Inst.* 94:926-35).

In some embodiments, the virally mediated tumor is associated with Epstein Barr Virus (EBV). Epstein Barr Virus is a member of the Herpesviridae family that, following primary infection, replicates in the epithelial cells of the oropharynx and infect recirculating B lymphocytes. Infection can lead to acute infectious mononucleosis, also known as glandular fever. Infectious mononucleosis is a benign lymphoproliferative disease characterized by transient immunosuppression and an expansion of atypical lymphocytes, the majority of which are CD8$^+$T cells. In these T cells, EBV establishes a latent but persistent infection during which a select set of viral genes are expressed. The entire genome can persist in the proliferating lymphocytes as episomal DNA. EBV infection is associated with Burkitt's lymphoma, Hodgkin's lymphoma, and adult T cell leukemia.

The LMP2A protein encoded by the EBV genome is a transmembrane protein thought to play a role in maintaining the latency of the EBV virus following infection. It consists of an extended amino terminal tail, 12 membrane spanning domains, and a cytoplasmic domain. The amino terminal region contains the ITAM motif, which allows interaction of LMP2A with Syk kinase (Fruehling et al., 1997, *Virology*, 235:241-251). LMP2A appears to regulate Syk kinase in lymphoid cells to promote B-cell survival and maintain latency. Because Syk plays a critical role in the signal transduction pathways that regulate other signaling pathways, such as PI-3K, BLNK, and phospholipase y2 and is involved in enhancing lymphoid cell survival, improper Syk activation through LMP2A protein or other virally mediated effectors may play a role in inducing aberrant lymphoproliferation (Caldwell et al., 2000, *J Virol* 74(19):9115; Caldwell et al., 1998, *Immunity* 9:405)). Thus, inhibition of Syk activity can provide a therapeutic benefit for cell proliferative disorders associated with EBV viral infection.

In some embodiments, the virally mediated tumor to be treated with the Syk inhibitor is associated with Human T-cell Lymphotropic Virus (HTLV-1 virus), a retrovirus in the same class of virus as the AIDS virus, HIV-1. The virus is tropic for CD4$^+$T-cells although CD8$^+$T-cells can also serve as a viral reservoir. HTLV-1 infection is associated with, among others, adult T-cell Leukemia/lymphoma (ATLL) and a number of other lymphocyte disorders. During HTLV-1 infection, Syk is expressed in infected cells while expression of the Syk related kinase, ZAP-70, is absent (Weil et al., 1999, *J. Virol.* 73(5): 3709-17). Dysregulation of a number of kinases, including Syk, is implicated in HTLV-1 mediated induction of adult T-cell leukemia.

In some embodiments, the virally mediated tumor is associated with mammary tumor virus (MTV). ITAM sequences are found within the Env gene of murine mammary tumor virus (MMTV), a B type retrovirus identified as an etiological agent for breast cancer in mice. Mouse mammary epithelial cells transfected with MMTV Env gene display characteristics of a transformed phenotype, such as colony formation in soft agar and invasiveness in basement membrane preparations (Katz et al., 2005, *J Exp Med.* 201(3):431-9). Murine mammary tumor virus-like sequences are also present in human cancers, such as breast cancer and T cell lymphomas (Wang et al., 2000, *Clinical Cancer Res.* 6:1273-1278), and correlated with tumorigenesis as these sequences are not observed in the majority of normal breast tissue. Thus, tumors associated with MTV can be treated with the Syk kinase inhibitors.

It is to be understood that use of Syk inhibitor compounds for treating virally mediated tumors is not limited to tumors associated with the viruses specified above. As noted, any tumors associated with an oncogenic virus in which Syk is activated as part of its oncogenic mechanism, whether or not it involves ITAM sequences, can be targeted using the Syk inhibitor compounds.

In some embodiments, the cell proliferative disorder that can be targeted with the inhibitors comprise cell proliferative disorders associated with aberrant Flt-3 kinase activity. The term "aberrant Flt-3 kinase activity" refers to activity that is abnormal from what the normal level of Flt-3 kinase activity would be for a wild type Flt-3 kinase or in a normal Flt-3 expressing cell, tissue, organ, or organism. Aberrant Flt-3 kinase activity can arise from mislocalization of the protein (spatial expression), increases or decrease in activity of the enzyme (directly or indirectly), or changes in temporal expression (i.e., developmental expression).

In some embodiments, the aberrant kinase activity is associated with variants of Flt-3. In some embodiments, these variants are characterized by increased Flt-3 receptor kinase activity. As used herein, "increased kinase activity" refers to kinase activity that it higher than observed for a wild type Flt-3 kinase or in a normal Flt-3 expressing cell, tissue, organ, or organism. Exemplary increased kinase activity are found in cells with certain Flt-3 variants, such as for example, Flt-3 ITD and Flt-3 activation loop mutations.

Because aberrant Flt-3 kinase activity is observed in many different types of hematological neoplasms, in some embodiments, the Syk/Flt-3 inhibitory compounds can be used to treat hematopoietic neoplasms characterized by the presence of an aberrant Flt-3 kinase. Thus, in some embodiments, the hematological neoplasms treatable with the Syk/Flt-3 inhibitory compound can include, among others, acute myelogenous leukemia, B-precursor cell acute lymphoblastic leukemia, T-cell acute lymphoblastic leukemia, and chronic myelogenous leukemia (CML) in which the presence of an aberrant Flt-3 has been diagnosed or is suspected in the subject. However, it is to be understood that the skilled artisan can apply the treatments without such information and that the inhibitory compounds can be given prophylactically to increase the probability of survival. Moreover, the skilled artisan can apply the Syk/Flt-3 inhibitory compounds herein to other cell proliferative disorders in which an aberrant Flt-3 kinase activity has been detected or is suspected.

In other aspects, the present disclosure is directed to the treatment of tumor metastasis by use of the Syk kinase inhibitors. Metastasis is a characteristic of malignant tumor cells whereby tumor cells detach from its site of origin and then spread to colonize at other sites. These secondary tumors can form in tissues unrelated to the cells from which the tumor cells originate. It is the formation of these secondary tumors by metastasis that appears to be the primary cause of mortality from malignant forms of cancer. Metastasis begins when malignant cells break off from the primary tumor and enter the blood or lymphatic system, and then migrate to other colonization sites. Generally, normal cells do not detach and invade other tissues because of various signals that inhibit dissimilar cells from adhering to each other, as well as signals between cells that inhibit cell growth. Cell transformation, however, alters these normal regulatory programs such that tumor cells interact with local tissue cells to modify the local extracellular matrix, stimulate migration, and promote proliferation and survival. Alterations of cell adhesion molecule (CAMs), such as those members of the immunoglobulin and calcium-dependent cadherin families and integrins, appear to play critical role in invasion and metastasis. For instance, alteration of N-CAM from a highly adhesive isoform to a poorly adhesive form, which along with its down regulation, may lead to invasive pancreatic cancer.

Another class of adhesion proteins implicated in tissue invasiveness and metastasis are integrins. As noted above, integrins form a diverse class of cell surface molecules. Permutations in the spectrum of the more than 22 integrin subtypes are able to create a flexible system for changing interaction of cells in response to different cell signaling states or changing external environments. Integrins interact dynamically with extracellular ligands depending on activation state of the integrin, which is controlled by intracellular signals (i.e., inside out signaling) that modifies integrin affinity and avidity. Conversely, interaction of integrin with extracellular ligands can trigger signal transduction cascades that affect cell adhesive properties and cellular responses to changing extracellular environments (i.e., outside-in signaling). Changes in expression of integrin subunits induce or inhibit invasive and metastatic growth, implicating these proteins as critical determinants of these processes (Guo et al., 2004, *Nat. Rev. Mol. Cell Biol.* 5(10):816-26; Jin et al., 2004, *Br. J. Cancer,* 90:561-565). For instance, integrin $\alpha v\beta 3$ is required for angiogenesis, and its upregulation is correlated with tumor invasiveness and metastatic potential (Liapis et al., 1996, *Diag. Mol. Pathol.* 23:127-135). Cultured metastatic breast cancer cells show constitutive expression of $\alpha v\beta 3$ (Pecheur et al., 2002, *FASEB J.* 16:1266-1268) while inhibiting $\alpha_v$ subunit containing integrin activity, such as by use of RGD peptidomimetic agents that compete for binding of the integrin with its natural substrate, can reduce the metastatic potential of tumors without affecting cell proliferation properties (Kristen et al., 2004, *Clin. Exp. Metastasis* 21(2):129-38; Harms et al., 2004, *Clin. Exp. Metastasis* 21(2):119-28). Similarly, overexpression of $\beta 1$ integrins can disrupt adherens junctions that function to keep cells attached to the basement membrane.

Syk kinase activity is associated with various integrins expressed on cells of the hematopoietic lineage, but also in non-hematopoietic cells. Syk kinase is implicated in $\beta 1$ integrin signaling of lung epithelial cells (Ulanova et al., 2004, *Am. J. Physiol. Lung Cell Mol. Physiol.* 288:L497-L507) and monocytes (Lin et al., 1995, *J. Biol. Chem.* 270(27):16189-97), $\beta 2$ integrin signaling in granulocytes/neutrophils (Miura et al., 2000, *Blood* 96(5):1733-9; Kusumoto et al., 2001, *Microbiol. Immunol.* 45(3):241-8), and $\beta 3$ integrin signaling in platelet activation and cell adhesion (Gao et al., 1997, *EMBO J.* 16(21):6414-25). Given the connection provided herein between Syk kinase activity and tumorigenesis, the use of Syk kinase inhibitors in attenuating the invasiveness and metastatic properties of tumors is indicated through the link between Syk kinase activity and certain integrins (Mocsai et al., 2002, *Immunity* 16(4):547-58). Thus, in some embodiments, inhibitors of Syk kinase can be used to modulate metastatic properties of tumors mediated via integrin activity. In some embodiments, the Syk kinase inhibitors can be used to attenuate tumor cell tissue invasiveness and metastatic potential affected by $\beta 1$ integrins (Lin et al., 1995, *J. Biol. Chem.* 270:16189-16197; Kusumoto et al., *Microbiol Immunol.,* 2001, 45(3):241-8; Ortiz-Stem et al., 2005, *J Leukoc Biol. (Epub)).* An exemplary integrin of this type is integrin $\alpha_2 b_1$.

In some embodiments, the Syk kinase inhibitors can be used to attenuate tumor cell tissue invasiveness and metastatic potential affected by the activity of $\beta 2$ integrins (CD18) (Willeke et al., 2003, *J Leukoc. Biol.* 74(2):260-9). These include, among others, CD11a/CD18, CD11b/CD18, CD11c/CD18, and CD11d/CD18. In further embodiments, the Syk kinase inhibitors can be used to attenuate tumor cell tissue invasiveness and metastatic potential affected by the activity of $\beta 3$ integrins. Exemplary integrins of this type are $\alpha_{IIb}\beta_3$ and $\alpha v\beta 3$.

Various tumor types capable of metastasis can be treated with the Syk inhibitor compounds. Such tumors include, by way of example and not limitation, breast cancer, ovarian cancer, renal cancer, gastrointestinal cancer, kidney cancer, bladder cancer, pancreatic cancer, lung squamous carcinoma, and adenocarcinoma (see, e.g., Felding-Habermann et al., 2001, *Proc Natl Acad Sci USA* 98(4): 1853-8). Therapeutic treatment to attenuate the metastasis of established tumors can follow a diagnosis of metastasis. If no diagnosis of metastasis has been made, the inhibitor compound can be administered prophylactically to reduce the probability of metastasis.

It is to be understood that the Syk inhibitor compounds can be used independently of any other treatment, or used in combination with other cancer treatment regimens, including surgery, radiology, or other chemotherapies. Accordingly, in some embodiments, the Syk kinase inhibitors can be used in combination with other chemotherapeutic agents. Combination treatments with Syk inhibitors can target different cellular components by appropriate choice of the second chemotherapeutic agent. For instance, Syk inhibitors can be used in some embodiments to limit the metastatic potential of tumor cells while another chemotherapeutic agent can be used to eliminate or kill aberrant cells.

Various chemotherapeutic agents can be used in combination with Syk kinase inhibitors to treat cell proliferative disorders. These chemotherapeutic agents can be general cytotoxic agents or target a specific cellular molecule. Various classes of cancer chemotherapeutic agents include, among others, antimetabolites, agents that react with DNA (e.g., alkylating agents, coordination compounds, etc.), inhibitors of transcription enzymes, topoisomerase inhibitors, DNA minor-groove binding compounds, antimitotic agents (e.g., vinca alkyloids), antitumor antibiotics, hormones, and enzymes. Exemplary alkylating agents include, by way of example and not limitation, mechlorothamine, cyclophosphamide, ifosfamide, melphalan, chlorambucil, ethyleneimines, methylmelamines, alkyl sulfonates (e.g., busulfan), and carmustine. Exemplary antimetabolites include, by way of example and not limitation, folic acid analog methotrexate; pyrimidine analogs fluorouracil, cytosine arabinoside; and purine analogs mecaptopurine, thioguanine, and azathioprine. Exemplary vinca alkyloids include, by way of example and not limitation, vinblastine, vincristine, paclitaxel, and colchicine. Exemplary antitumor antibiotics include, by way of example and not limitation, actinomycin D, daunorubicin, and bleomycin. An exemplary enzyme effective as anti-neoplastic agent is L-asparaginase. Exemplary coordination compounds include, by way of example and not limitation, cisplatin and carboplatin. Exemplary hormones and hormone related compounds include, by way of example and not limitation, adrenocorticosteroids prednisone, and dexamethasone; aromatase inhibitors amino glutethimide, formestane, and anastrozole; progestin compounds hydroxyprogesteron caproate, medroxyprogesterone; and anti-estrogen compound tamoxifen. Exemplary topoisomerase inhibitors include, by way of example and not limitation, amsacrine (m-AMSA); mitoxantrone, topotecan, irinotecan, and camptothecin.

These and other useful anti-cancer compounds are described in *Merck Index,* 13th Ed. (O'Neil, M. J. et al., ed) Merck Publishing Group (2001) and *Goodman and Gilmans The Pharmacological Basis of Therapeutics,* 10th Edition, Hardman, J. G. and Limbird, L. E. eds., pg. 1381-1287, McGraw Hill, (1996), both of which are incorporated herein by reference.

Other anti-proliferative compounds useful in combination with the Syk inhibitor compounds include, by way of example and not limitation, antibodies directed against growth factor receptors (e.g., anti-Her2); cytokines such as interferon-α and interferon-γ, interleukin-2, and GM-CSF; and antibodies for cell surface markers (e.g., anti-CTLA-4, anti-CD20 (rituximab); anti-CD33). When antibodies against cell surface markers are used, a chemotherapeutic agent can be conjugated to it for specific targeting to the tumor cell. Suitable conjugates include radioactive compounds (e.g., radioactive metal bound to an antibody conjugated chelator), cytotoxic compounds, and drug activating enzymes (e.g., allinase, peptidases, esterases, catalytic antibodies, etc.) (see, e.g., Arditti et al., 2005, *Mol. Cancer Therap.* 4(2):325-331; U.S. Pat. No. 6,258,360; incorporated herein by reference)

In some embodiments, the Syk inhibitors can be used with a second kinase inhibitor that targets an oncogenic kinase different from Syk or Syk and Flt-3. Given that Syk inhibitors are disclosed herein for the treatment of hematopoietic neoplasms, other compatible kinase inhibitors used for treating hematopoietic neoplasms can also be used. In some embodiments, the second kinase inhibitor is an inhibitor of Abl kinase. Chronic myelogenous leukemia is a myeloid neoplasm characterized by malignant proliferation of leukemic stem cells in the bone marrow. The majority of chronic myelogenous leukemia are associated with a cytogenetic abnormality defined by a reciprocal translocation t(9;22)(q34;q11). This chromosomal aberration results in generation of a BCR/ABL fusion protein with activated kinase activity. Inhibitors of the fusion protein kinase activity can be effective in treating chronic myelogenous leukemia although resistant forms can develop upon continued treatment. Use of Syk kinase inhibitor in combination of Abl kinase inhibitors can lessen the chances of resistant cells by targeting a different cellular process than targeted by the second kinase inhibitor. An exemplary Abl kinase inhibitor is 2-phenylaminopyrimidine, also known as imatinib mesylate and Gleevec®. Thus, in some embodiments, the Syk kinase inhibitors can be used in combination with Abl kinase inhibitor 2-phenylaminopyrimidine and its derivatives. In other embodiments, the second kinase inhibitor can be pyridol[2-3-d]pyrimidine and its derivatives, which was originally identified as inhibitors of Src kinase. In still other embodiments, the second kinase inhibitor can be tyrphostins and its derivatives (e.g., adaphostin), which can affect the association of the kinase with its substrates. Other kinase inhibitor compounds will be apparent to the skilled artisan.

As further described herein, the administration of other chemotherapeutic agents can be done in the form of a composition, or administered adjunctively in combination with the Syk inhibitor. When provided adjunctively, the chemotherapeutic agents can be administered simultaneously with or sequentially with administration of the Syk inhibitor.

6.2 Syk Kinase and Syk/Flt-3 Kinase Inhibitors

In reference to various inhibitors, the terms used to describe the compounds will have their ordinary and common meaning as used by those in the art unless a different definition is provided herein or is provided in the references describing the specific inhibitor compounds.

"Alkyl" by itself or as part of another substituent refers to a saturated or unsaturated, branched, straight-chain or cyclic monovalent hydrocarbon group having the stated number of carbon atoms (i.e., $C_1$-$C_6$ means from one to six carbon atoms) derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl cyclobuta-1,3-dien-1-yl, but-1-yn-1-yl, but-1-yn-3-yl, but-3-yn-1-yl, etc.; and the like. The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. The expression "lower alkyl" refers to alkyl groups composed of from 1 to 6 carbon atoms.

"Alkanyl" by itself or as part of another substituent refers to a saturated branched, straight-chain or cyclic alkyl group. Typical alkanyl groups include, but are not limited to, methanyl; ethanyl; propanyls such as propan-1-yl, propan-2-yl (isopropyl), cyclopropan-1-yl, etc.; butyanyls such as butan-1-yl, butan-2-yl (sec-butyl), 2-methyl-propan-1-yl (isobutyl), 2-methyl-propan-2-yl (t-butyl), cyclobutan-1-yl, etc.

"Alkenyl" by itself or as part of another substituent refers to an unsaturated branched, straight-chain or cyclic alkyl group having at least one carbon-carbon double bond derived by the removal of one hydrogen atom from a single carbon atom of a parent alkene. The group can be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2yl, buta-1,3-dien-1-yl, buta-1,3-dien-2-yl, cyclobut-1-en-1-yl, cyclobut-1-en-3-yl, cyclobuta-1,3-dien-1-yl, etc.

"Alkynyl" by itself or as part of another substituent refers to an unsaturated branched, straight-chain or cyclic alkyl group having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.

"Parent Aromatic Ring System" refers to an unsaturated cyclic or polycyclic ring system having a conjugated .pi.electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like.

"Aryl" by itself or as part of another substituent refers to a monovalent aromatic hydrocarbon group having the stated number of carbon ring atoms (i.e., $C_5$-$C_{14}$ means from 5 to 14 carbon ring atoms) derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In preferred embodiments, the aryl group is ($C_5$-$C_{14}$) aryl, with ($C_5$-$C_{10}$) being even more preferred. Particularly preferred aryls are cyclopentadienyl, phenyl and naphthyl.

"Arylalkyl" by itself or as part of another substituent refers to an acyclic alkyl group in which one of the hydrogen atoms bonded to a carbon atom, typically a terminal or Sp3 carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In preferred embodiments, the arylalkyl group is ($C_6$-$C_{16}$) arylalkyl, e.g., the alkanyl, alkenyl or alkynyl moiety of the arylalkyl group is ($C_1$-$C_6$) and the aryl moiety is ($C_5$-$C_{10}$). In particularly preferred embodiments the arylalkyl group is ($C_6$-$C_{13}$), e.g., the alkanyl, alkenyl or alkynyl moiety of the arylalkyl group is ($C_1$-$C_3$) and the aryl moiety is ($C_5$-$C_{10}$).

"Parent Heteroaromatic Ring System" refers to a parent aromatic ring system in which one or more carbon atoms are each independently replaced with the same or different heteroatoms or heteroatomic groups. Typical heteroatoms or heteroatomic groups to replace the carbon atoms include, but are not limited to, N, NH, P, O, S, Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Also included in the definition of "parent heteroaromatic ring system" are those recognized rings that include substituents, such as benzopyrone. Typical parent heteroaromatic ring systems include, but are not limited to, arsindole, benzodioxan, benzofuran, benzopyrone, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Heteroaryl" by itself or as part of another substituent refers to a monovalent heteroaromatic group having the stated number of ring atoms (i.e., "5-14 membered" means from 5 to 14 ring atoms) derived by the removal of one hydrogen atom from a single atom of a parent heteroaromatic ring system. Typical heteroaryl groups include, but are not limited to, groups derived from acridine, arsindole, carbazole, .beta.-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryl group is a 5-14 membered heteroaryl or a 5-10 membered heteroaryl.

"Heteroarylalkyl" by itself or as part of another substituent refers to an acyclic alkyl group in which one of the hydrogen atoms bonded to a carbon atom, typically a terminal or Sp3 carbon atom, is replaced with a heteroaryl group. Where specific alkyl moieties are intended, the nomenclature heteroarylalkanyl, heteroarylalkenyl and/or heterorylalkynyl is used. In some embodiments, the heteroarylalkyl group is a 6-20 membered heteroarylalkyl, e.g., the alkanyl, alkenyl or alkynyl moiety of the heteroarylalkyl is 1-6 membered and the heteroaryl moiety is a 5-14-membered heteroaryl. In particularly preferred embodiments, the heteroarylalkyl is a 6-13 membered heteroarylalkyl, e.g., the alkanyl, alkenyl or alkynyl moiety is 1-3 membered and the heteroaryl moiety is a 5-10 membered heteroaryl.

"Substituted Alkyl, Aryl, Arylalkyl, Heteroaryl or Heteroarylakyl" refers to an alkyl, aryl, arylalkyl, heteroaryl or heteroarylakyl group in which one or more hydrogen atoms is replaced with another substituent group. Exemplary substituent groups include, but are not limited to, —OR', —SR', —NR'R', —NO$_2$, —NO, —CN, —CF$_3$, halogen (e.g., —F, —Cl, —Br and —I), —C(O)R', —C(O)OR', —C(O)NR', —S(O)$_2$R', —S(O)$_2$NR'R', where each R' is independently selected from the group consisting of hydrogen and ($C_1$-$C_6$) alkyl.

"Prodrug" refers to a derivative of an active compound (drug) that requires a transformation under the conditions of use, such as within the body, to release the active drug. Prodrugs are frequently, but not necessarily, pharmacologically inactive until converted into the active drug. Prodrugs are typically obtained by masking a functional group in the drug believed to be in part required for activity with a progroup (defined below) to form a promoiety which undergoes a transformation, such as cleavage, under the specified conditions of use to release the functional group, and hence the active drug. The cleavage of the promoiety can proceed spontaneously, such as by way of a hydrolysis reaction, or it can be catalyzed or induced by another agent, such as by an enzyme, by light, by acid, or by a change of or exposure to a physical or environmental parameter, such as a change of temperature. The agent can be endogenous to the conditions of use, such as an enzyme present in the cells to which the prodrug is administered or the acidic conditions of the stomach, or it can be supplied exogenously.

A wide variety of progroups, as well as the resultant promoieties, suitable for masking functional groups in the active drugs to yield prodrugs are well-known in the art. For example, a hydroxyl functional group can be masked as a sulfonate, ester or carbonate promoiety, which can be hydrolyzed in vivo to provide the hydroxyl group. An amino functional group can be masked as an amide, carbamate, imine, urea, phosphenyl, phosphoryl or sulfenyl promoiety, which can be hydrolyzed in vivo to provide the amino group. A carboxyl group can be masked as an ester (including silyl esters and thioesters), amide or hydrazide promoiety, which can be hydrolyzed in vivo to provide the carboxyl group. Other specific examples of suitable progroups and their respective promoieties will be apparent to those of skill in the art.

Various compounds that inhibit Syk kinase or Syk/Flt-3 kinase activity can be used in the methods described herein. These include, among others, small organic molecules, peptides or proteins, or nucleic acids. As used herein, a "Syk inhibitor" or "Syk kinase inhibitory compound" refers to any compound that directly inhibits the activity of Syk kinase itself or inhibits Syk interaction with other cellular targets needed for proper Syk function in the $IC_{50}$ range described herein. Inhibitors as used herein include the classical description of enzyme inhibitors, such as competitive, noncompetitive and uncompetitive inhibitors. Compounds that are Syk inhibitors are generally those that display an $IC_{50}$ with respect to a Syk kinase activity, such as the ability of Syk kinase to phosphorylate a synthetic or endogenous substrate, in an in vitro or cellular assay, in the range of about 5 uM or lower, about 1 uM or lower, about 500 nm or lower, about 100 nM or lower, about 50 nM or lower, about 10 mM or lower, or about 1 nM or lower. For instance, exemplary Syk inhibitor compounds are disclosed in U.S. application Ser. No. 10/631,029 and PCT publication WO 2004/014382. Skilled artisans will appreciate that compounds exhibiting lower $IC_{50}$s, such as in the range of about 100 nM, 10 nM, 1 nM, or even lower, are useful for the methods herein.

In some embodiments, the inhibitor compound can be selective for Syk kinase. A "Syk kinase selective inhibitory compound" refers to a compound displaying selectivity for Syk, which is defined as the ratio of an $IC_{50}$ for a reference kinase over an $IC_{50}$ for Syk kinase in a defined set of assays. Generally the Syk kinase selective inhibitory compound can have a selectivity for Syk kinase that is greater than about 10, greater than about 50, greater than about 100, greater than about 1000, or higher. The reference kinase can be any kinase activity associated with cell proliferative disorders, including kinases such as, by way of example and not limitation, Aurora-A, AKT, CDK1/cyclinB, CDK2/cyclinA, CDK3/cyclinE, CDK5/p35, CDK6/cyclinD3, CDK7/cyclinH/MAT1, CHK1, CHK2, EGFR, c-RAF, RAS, cSRC, Yes, Fyn, Lck, Fes, Lyn, Bmx, FGFR3, GSK3α., GSK3β, P13, IGF-1R, MAPK2, MAPKAP-K2, JNK, MEK1, p70S6K, PAK2, PDGFRα, PDGFRβ, PDK1, PKA, PKCε, PKC, PKD2, VEGF, PRAK, PRK2, ROCK-II, Rsk1, Rsk2, Rsk3, SGK. Various assays for each of the kinases will be apparent to the skilled artisan. For example, Aurora kinase activities can use natural or synthetic substrates (e.g., fluorescent peptides, Histone H3) in in vitro assays, or measurement of phosphorylated products in cells (Walter et al., 2000, Oncogene 19(42): 4906-16). Kinase activities can be detected using various approaches, including, by way of example and not limitation, immunoprecipitation (e.g., Cyclex Aurora A kinase Assay; MBL Corp, Woburn, Mass., USA) mobility shift (e.g., Caliper Technologies, Mountain View, Calif., USA), autofluorescent fusion protein substrates (e.g., U.S. Pat. No. 6,248,550), and FRET based assays (Z-LYTE®; Invitrogen, Calif., USA). As will be appreciated by the skilled artisan, other active kinases involved in aberrant cell proliferation can be used to determine the selectivity of a kinase inhibitor for Syk.

In some embodiments, the inhibitor compound used for treating the cell proliferative disorder comprises a Syk/Flt-3 kinase inhibitory compound. A "Syk/Flt-3 kinase inhibitory compound" or "Syk/Flt-3 kinase inhibitor" refers to a Syk inhibitory compound that can also inhibit Flt-3 kinase, such as by directly inhibiting the activity of Flt-3 kinase itself or by inhibiting the interaction with other cellular targets needed for proper Flt-3 function in the $IC_{50}$ range described herein. Compounds that are Syk/Flt-3 inhibitors are generally those that display an $IC_{50}$ with respect to a Flt-3 kinase activity, such as the ability of Flt-3 kinase to phosphorylate a synthetic or endogenous substrate, in an in vitro or cellular assay, in the range of about 5 uM or lower, about 1 uM or lower, about 500 nm or lower, about 100 nM or lower, about 50 nM or lower, about 10 nM or lower, or about 1 nM or lower. For instance, exemplary Syk/Flt-3 inhibitor compounds can be found in the genus of compounds disclosed in U.S. application Ser. No. 10/631,029 and PCT publication WO 2004/014382. Skilled artisans will appreciate that compounds exhibiting lower $IC_{50}$s, such as in the range of about 100 nM, 10 nM, 1 nM, or even lower, are useful for the methods herein.

Various kinase inhibitors can be used in the methods herein, and is meant to include, where applicable, the salts, hydrates, solvates, and N-oxides of the corresponding inhibitor compounds. In some embodiments, the Syk kinase or Syk/Flt-3 kinase inhibitor comprises 2,4-pyrimidinediamine compounds and its various derivatives, as described in U.S. application Ser. No. 10/631,029 and published PCT application No. WO 2004/014382, incorporated herein by reference in their entirety. These compounds generally comprise a 2,4-pyrimidinediamine "core" having the following structure and numbering convention:

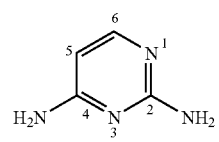

I

The compounds are substituted at the C2 nitrogen (N2) to form a secondary amine and are optionally further substituted at one or more of the following positions: the C4 nitrogen (N4), the C5 position and/or the C6 position. When substituted at N4, the substituent forms a secondary amine. The substituent at N2, as well as the optional substituents at the other positions, can range broadly in character and physicochemical properties. For example, the substituent(s) can be a branched, straight-chained or cyclic alkyl, a branched, straight-chained or cyclic heteroalkyl, a mono- or polycyclic aryl a mono- or polycyclic heteroaryl or combinations of these groups. These substituent groups can be further substituted, as is described in U.S. application Ser. No. 10/631,029 and PCT publication WO 2004/014382.

The N2 and/or N4 substituents can be attached directly to their respective nitrogen atoms, or they can be spaced away from their respective nitrogen atoms via linkers, which can be the same or different. The nature of the linkers can vary widely, and can include virtually any combination of atoms or groups useful for spacing one molecular moiety from another. For example, the linker can be an acyclic hydrocarbon bridge (e.g, a saturated or unsaturated alkyleno such as methano, ethano, etheno, propano, prop[1]eno, butano, but[1]eno, but[2]eno, buta[1,3]dieno, and the like), a monocyclic or polycyclic hydrocarbon bridge (e.g., [1,2]benzeno, [2,3]naphthaleno, and the like), a simple acyclic heteroatomic or heteroalkyldiyl bridge (e.g., —O—, —S—, —S—O—, —NH—, —PH—, —C(O)—, —C(O)NH—, —S(O)—, —S(O)$_2$—, —S(O)NH—, —S(O)$_2$NH—, —O—CH$_2$—, —CH$_2$—O—CH$_2$—, —O—CH═CH—CH$_2$—, and the like), a monocyclic or polycyclic heteroaryl bridge (e.g., [3,4]furano, pyridino, thiopheno, piperidino, piperazino, pyrazidino, pyrrolidino, and the like) or combinations of such bridges.

The substituents at the N2, N4, C5 and/or C6 positions, as well as the optional linkers, can be further substituted with one or more of the same or different substituent groups. The nature of these substituent groups can vary broadly. Non-limiting examples of suitable substituent groups include branched, straight-chain or cyclic alkyls, mono- or polycyclic aryls, branched, straight-chain or cyclic heteroalkyls, mono- or polycyclic heteroaryls, halos, branched, straight-chain or cyclic haloalkyls, hydroxyls, oxos, thioxos, branched, straight-chain or cyclic alkoxys, branched, straight-chain or cyclic haloalkoxys, trifluoromethoxys, mono- or polycyclic aryloxys, mono- or polycyclic heteroaryloxys, ethers, alcohols, sulfides, thioethers, sulfanyls (thiols), imines, azos, azides, amines (primary, secondary and tertiary), nitriles (any isomer), cyanates (any isomer), thiocyanates (any isomer), nitrosos, nitros, diazos, sulfoxides, sulfonyls, sulfonic acids, sulfamides, sulfonamides, sulfamic esters, aldehydes, ketones, carboxylic acids, esters, amides, amidines, formadines, amino acids, acetylenes, carbamates, lactones, lactams, glucosides, gluconurides, sulfones, ketals, acetals, thioketals, oximes, oxamic acids, oxamic esters, etc., and combinations of these groups. Substituent groups bearing reactive functionalities can be protected or unprotected, as is well-known in the art.

Specific embodiments of Syk kinase inhibitory compounds are also described in U.S. application Ser. No. 10/631,029, filed Jul. 29, 2003; U.S. application Ser. No. 10/903,263, filed Jul. 30, 2004 (U.S. application Publication No. 2005/0234049); U.S. application Ser. No. 10/903,870, filed Jul. 30, 2004 (U.S. application Publication No. 2005/0209224); U.S. Application Ser. No. 60/630,808; and PCT publication WO 2004/014382. Prodrugs forms of the 2,4-pyrimidinediamine compounds are described in U.S. application Ser. No. 11/337,049, filed Jan. 19, 2006. All publications and patent applications are incorporated herein by reference in their entirety. These compounds are also disclosed in Appendixes A, B, C and D of U.S. Provisional Application Ser. No. 60/672,648, filed Apr. 18, 2005, the entire contents of which is incorporated herein by reference.

In one embodiment of the invention, the method for treating the cell proliferative disorder comprises administering to a subject in need thereof an amount of a prodrug, or a salt thereof, of a Syk kinase or Syk/Flt-3 kinase inhibitory compound effective to treat the cell proliferative disorder, the prodrug having the structure

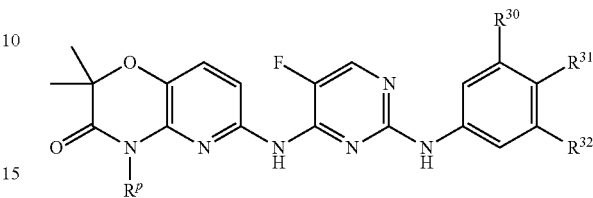

wherein each $R^{30}$, $R^{31}$ and $R^{32}$ is independently selected from hydrogen, lower alkyl, lower alkenyl, lower alkynyl, (C6-C14) aryl, phenyl, 5-14 membered heteroaryl, (C7-C20) arylalkyl, benzyl, 7-20 membered heteroarylalkyl, —OR, chloro, fluoro, bromo, cyano, nitro, —C(O)R, —C(O)OR, —NRR, —S(O)$_2$NRR, —C(O)NRR, —N(R)S(O)$_2$R and —NC(O)OR, where each R is independently selected from hydrogen and lower alkyl; and $R^p$ is selected from —CH$_2$—O—P(O)(OH)$_2$, —CH$_2$CH$_2$—O—P(O)(OH)$_2$, —CH$_2$OH.

In one embodiment of the invention, $R^{30}$, $R^{31}$ and $R^{32}$ are each independently a lower alkoxy.

In one embodiment of the invention, the prodrug is of the formula

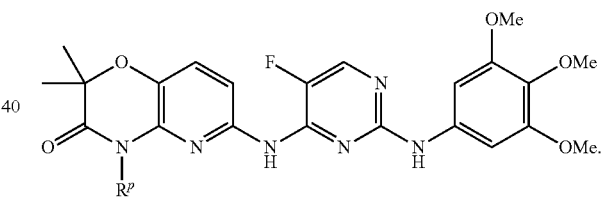

In one embodiment of the invention, the prodrug has the structure

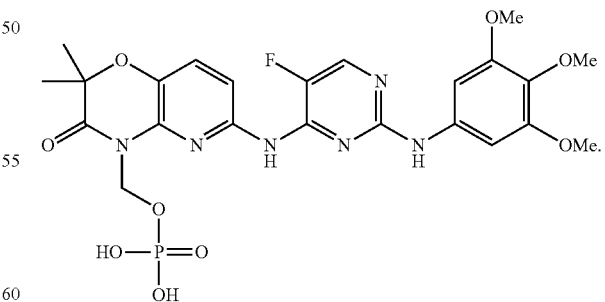

It has been discovered that a specific active 2,4-pyrimidinediamine drug (Compound III, below), exhibits vastly superior water solubility when formulated as a phosphate prodrug (Compound 4, below):

| Compound | Structure | Solubility |
|---|---|---|
| Compound III | 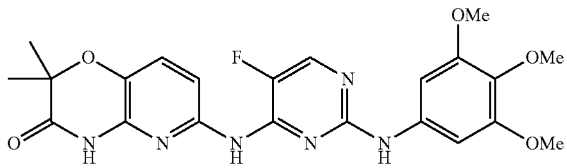 | 1-2 μg/ml |
| Compound 4 | 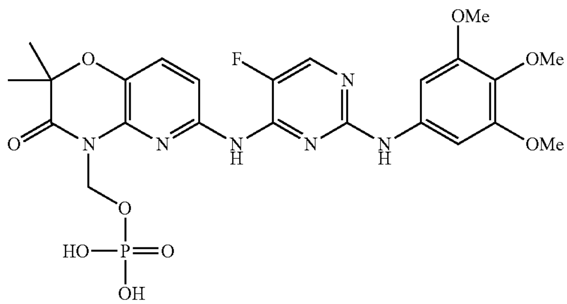 | >5 mg/ml |

(Structures of Compound III and Compound 4 shown above.)

This prodrug Compound 4 also exhibits superior bioavailability compared to the corresponding active drug Compound III when administered orally to test animals. In fact, unlike the drug Compound III, absorption of the prodrug Compound 4 is not dependent upon formulation. In pharmacokinetics studies carried out in rats, the prodrug Compound 4 was absorbed equally well from solutions (e.g., PEG-400 solutions and carboxymethylcellulose solutions) and powders (packed in hard gelatin capsules). While not intending to be bound by any particular theory of operation, it is believed that the improved oral bioavailability of the prodrug Compound 4, as well as its formulation-independent absorption, is due, at least in part, to its higher water-solubility. It is expected that other active 2,4-pyrimidinediamine compounds that have similarly low water solubilities, and hence oral bioavailabilities, will exhibit similar increases in water solubility and oral bioavailability when formulated as phosphate prodrugs.

Conversely, the corresponding phosphate ester prodrug of active drug Compound III would be expected to have lower water-solubility than the active Compound III compound. Thus, it is expected that phosphate ester prodrugs of active 2,4-pyrimidinediamine compounds that have lower water-solubility than the corresponding active 2,4-pyrimidinediamine compounds will be especially useful in applications and formulations where low water-solubility is desirable, such as formulations adapted for delivery via inhalation.

One class of active 2,4-pyrimidinediamine compounds that is expected to benefit from formulation as prodrugs, and in particular as phosphate prodrugs, includes 2,4-pyrimidinediamines in which the N4-substituent of the 2,4-pyrimidinediamine moiety is a substituted or unsubstituted nitrogen-containing heteroaryl ring of the formula

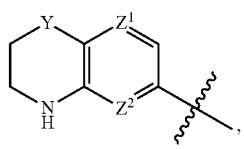

where $Z^1$ and $Z^2$ are each, independently of one another, selected from CH and N and Y is selected from $CH_2$, NH, O, S, S(O) and $S(O)_2$. Such prodrugs can include progroups $R^P$ at: one or both of the non-aromatic ring nitrogens of the heteroaryl ring, the N2-nitrogen of the 2,4-pyrimidinediamine moiety, the N4-nitrogen atom of the 2,4-pyrimidinediamine moiety and/or any available nitrogen atoms in the substituent attached to the N2 nitrogen atom of the 2,4-pyrimidinediamine moiety.

In one illustrative embodiment, the prodrugs are compounds according to structural formula (VI):

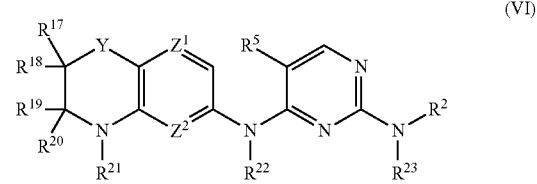

(VI)

including salts, solvates, hydrates and N-oxides thereof, wherein:

Y is selected from $CH_2$, $NR^{24}$, O, S, S(O) and $S(O)_2$;

$Z^1$ and $Z^2$ are each, independently of one another, selected from CH and N;

$R^2$ is selected from lower alkyl optionally substituted with one or more of the same or different $R^8$ groups, lower cycloalkyl optionally substituted with one or more of the same or different $R^8$ groups, cyclohexyl optionally substituted with one or more of the same or different $R^8$ groups, 3-8 membered cycloheteroalkyl optionally substituted with one or more of the same or different $R^8$ groups, (C6-C14) aryl optionally substituted with one or more of the same or different $R^8$ groups, phenyl optionally substituted with one or more of the same or different $R^8$ groups and 5-15 membered heteroaryl optionally substituted with one or more of the same or different $R^8$ groups;

$R^5$ is selected from halo, fluoro, cyano, nitro, trihalomethyl and trifluoromethyl;

$R^8$ is selected from $R^a$, $R^b$, $R^a$ substituted with one or more, for example, from one to four, of the same or different $R^a$ or $R^b$, —$OR^a$ substituted with one or more of the same or different $R^a$ or $R^b$, —$B(OR^a)_2$, —$B(NR^cR^c)_2$, —$(CH_2)_m$—$R^b$, —$(CHR^a)_m$—$R^b$, —O—$(CH_2)_m$—$R^b$, —S—$(CH_2)_m$—$R^b$, —O—$CHR^aR^b$, —O—$CR^a(R^b)_2$, —O—$(CHR^a)_m$—$R^b$, —O—$(CH_2)_m$—$CH[(CH_2)_mR^b]$ $R^b$, —S—(CHR$^a$)$_m$—R$^b$, —C(O)NH—(CH$_2$)$_m$—R$^b$, —C(O)NH—(CHR$^a$)$_m$—R$^b$, —O—(CH$_2$)$_m$—C(O)NH—(CH$_2$)$_m$—R$^b$, —S—(CH$_2$)$_m$—C(O)NH—(CH$_2$)$_m$—R$^b$, —O—(CHR$^a$)$_m$—C(O)NH—(CHR$^a$)$_m$—R$^b$, —S—(CHR$^a$)$_m$—C(O)NH—(CHR$^a$)$_m$—R$^b$, —NH—(CH$_2$)$_m$—R$^b$, —NH—(CHR$^a$)$_m$—R$^b$, —NH[(CH$_2$)$_m$R$^b$], —N[(CH$_2$)$_m$R$^b$]$_2$, —NH—C(O)—NH—(CH$_2$)$_m$—R$^b$, —NH—C(O)—(CH$_2$)$_m$—CHR$^b$R$^b$ and —NH—(CH$_2$)$_m$—C(O)—NH—(CH$_2$)$_m$—R$^b$;

$R^{17}$ is selected from hydrogen, halogen, fluoro, lower alkyl and methyl or, alternatively, $R^{17}$ may be taken together with $R^{18}$ to form an oxo (=O) group or, together with the carbon atom to which they are attached, a spirocycle containing from 3 to 7 carbon atoms;

$R^{18}$ is selected from hydrogen, halogen, fluoro, lower alkyl and methyl or, alternatively, $R^{18}$ may be taken together with $R^{17}$ to form an oxo (=O) group or, together with the carbon atom to which they are attached, a spirocycle containing from 3 to 7 carbon atoms;

$R^{19}$ is selected from hydrogen, lower alkyl, and methyl or, alternatively, $R^{19}$ may be taken together with $R^{20}$ to form an oxo (=O) group or, together with the carbon atom to which they are attached, a spirocycle containing from 3 to 7 carbon atoms;

$R^{20}$ is selected from hydrogen, lower alkyl and methyl or, alternatively, $R^{20}$ may be taken together with $R^{19}$ to form an oxo (=O) group or, together with the carbon atom to which they are attached, a spirocycle containing from 3 to 7 carbon atoms;

each $R^a$ is, independently of the others, selected from hydrogen, lower alkyl, lower cycloalkyl, cyclohexyl, (C4-C11) cycloalkylalkyl, (C6-C10) aryl, phenyl, (C7-C16) arylalkyl, benzyl, 2-6 membered heteroalkyl, 3-8 membered cycloheteroalkyl, morpholinyl, piperazinyl, homopiperazinyl, piperidinyl, 4-11 membered cycloheteroalkylalkyl, 5-10 membered heteroaryl and 6-16 membered heteroarylalkyl;

each $R^b$ is a suitable group independently selected from =O, —OR$^a$, (C1-C3) haloalkyloxy, =S, —SR$^a$, =NR$^a$, =NOR$^a$, —NR$^c$R$^c$, halogen, —CF$_3$, —CN, —NC, —OCN, —SCN, —NO, —NO$_2$, =N$_2$, —N$_3$, —S(O)R$^a$, —S(O)$_2$R$^a$, —S(O)$_2$OR$^a$, —S(O)NR$^c$R$^c$, —S(O)$_2$NR$^c$R$^c$, —OS(O)R$^a$, —OS(O)$_2$R$^a$, —OS(O)$_2$OR$^a$, —OS(O)$_2$NR$^c$R$^c$, —C(O)R$^a$, —C(O)OR$^a$, —C(O)NR$^c$R$^c$, —C(NH)NR$^c$R$^c$, —C(NR$^a$)NR$^c$R$^c$, —C(NOH)R$^a$, —C(NOH)NR$^c$R$^c$, —OC(O)R$^a$, —OC(O)OR$^a$, —OC(O)NR$^c$R$^c$, —OC(NH)NR$^c$R$^c$, —OC(NR$^a$)NR$^c$R$^c$, —[NHC(O)]$_n$R$^a$, —[NR$^a$C(O)]$_n$R$^a$, —[NHC(O)]$_n$OR$^a$, —[NR$^a$C(O)]$_n$OR$^a$, —[NHC(O)]$_n$NR$^c$R$^c$, —[NR$^a$C(O)]$_n$NR$^c$R$^c$, —[NHC(NH)]$_n$NR$^c$R$^c$ and —[NR$^a$C(NR$^a$)]$_n$NR$^c$R$^c$;

each $R^c$ is, independently of the others, selected from a protecting group and R$^a$, or, alternatively, the two R$^c$ bonded to the same nitrogen atom are taken together with that nitrogen atom to form a 5 to 8-membered cycloheteroalkyl or heteroaryl which may optionally include one or more of the same or different additional heteroatoms and which may optionally be substituted with one or more, for example, from one to four, of the same or different R$^a$ groups;

$R^{21}$, $R^{22}$ and $R^{23}$ are each, independently of one another, selected from hydrogen and a progroup R$^P$;

$R^{24}$ is selected from hydrogen, lower alkyl and progroup R$^P$;

each m is, independently of the others, an integer from 1 to 3; and each n is, independently of the others, an integer from 0 to 3, with the proviso that at least one of $R^{21}$, $R^{22}$, $R^{23}$ and $R^{24}$ is a progroup.

In the prodrugs described herein, and in particular in the prodrugs of structural formula (VI), $R^{21}$, $R^{22}$ and $R^{23}$ each represent either hydrogen or a progroup R$^P$. Also, R$^{24}$ represents hydrogen, a lower alkyl or a progroup R$^P$. Thus, the prodrugs can include a single R$^P$ progroup, two R$^P$ progroups, three R$^P$ progroups, or even more R$^P$ progroups, depending, in part, on the identity of Y and whether the R$^2$ substituent includes any R$^P$ progroups. In some embodiments, it is preferred that the prodrugs described herein, and in particular the prodrugs of structural formula (VI), include only one R$^P$ group. Without intending to be bound by any theory of operation, it is possible that the different R$^P$ groups in prodrugs including more than one R$^P$ progroup may metabolize at different rates. Prodrugs including a single R$^P$ progroup would avoid such differential metabolic kinetics. A specific embodiment of prodrugs according to structural formula (VI) that include a single progroup R$^P$ are compounds according to structural formula (VIa):

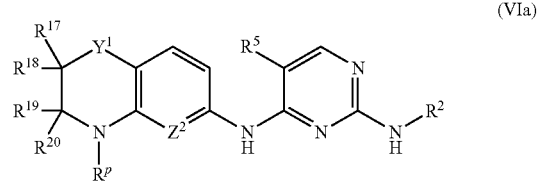

(VIa)

wherein $Y^1$ is selected from CH$_2$, NR$^{24}$, O, S, S(O) and S(O)$_2$; and $Z^2$, $R^2$, $R^5$, $R^{17}$, $R^{18}$, $R^{19}$, $R^{20}$, $R^{24}$ and R$^P$ are as previously defined, with the proviso that R$^2$ does not include any R$^P$ groups.

The identity of any R$^P$ progroups present in the prodrugs described herein is not critical for success, provided that it hydrolyzes under the conditions of use to yield the active 2,4-pyrimidinediamine compound. It has recently been discovered that a phosphate-containing prodrug according to the structure illustrated below:

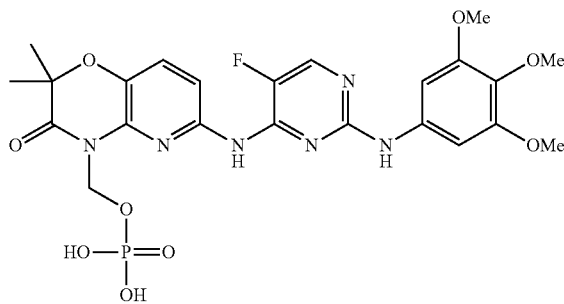

metabolizes in vivo to the corresponding active 2,4-pyrimidinediamine compound (Compound III), illustrated below:

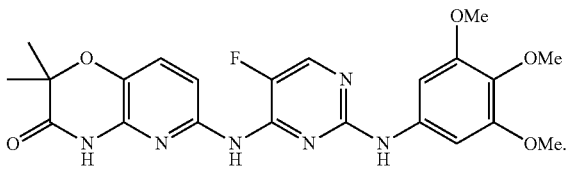

While not intending to be bound by any particular theory operation, it is believed that this prodrug metabolizes to active Compound III via the corresponding hydroxymethylamine intermediate illustrated below:

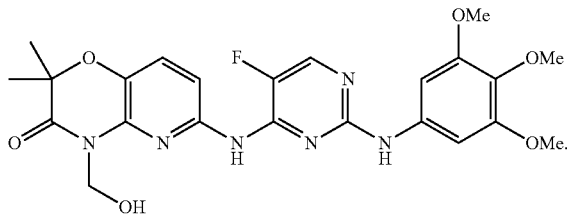

Such hydroxymethylamine compounds are known to be unstable under physiological conditions and various pH ranges where they hydrolyze in vivo to yield formaldehyde and the active drug substance. Based on this observation, it is believed that prodrugs that include hydroxyl "protecting" groups that can be metabolized in vivo, for example by the acidic conditions of the stomach and/or by enzymes present in the digestive tract or other organs and/or tissues or fluids with the body, to yield the hydroxymethylamine intermediate illustrated above will likewise metabolize to the active 2,4 pyrimidinediamine drug.

Moreover, it is expected that the amino and thio analogs of this hydroxymethylamine intermediate, will be similarly unstable at physiological conditions and also hydrolyze in vivo to the active 2,4-pyrimdiendiamine drug. Accordingly, it is also expected that the corresponding amino and thio compounds, as well as compounds in which the α-amino and a-thio groups are masked with "protecting" groups that are removed under physiological conditions of use to yield the α-amino and a-thio groups, will likewise make suitable prodrugs.

Thus, in some embodiments, the progroup(s) $R^P$ in the prodrugs of structural formulae (VI) and (VIa) are of the formula —$CR^dR^d$-A-$R^3$, where each $R^d$ is, independently of the other, selected from hydrogen, cyano, —C(O)$R^e$, —C(O)O$R^e$, —C(O)N$R^eR^e$, —C(O$R^e$)(O$R^e$), optionally substituted (C1-C20) alkyl, (C1-C20) perfluoroalkyl, optionally substituted (C7-C30) arylalkyl and optionally substituted 6-30membered heteroarylalkyl, where each $R^e$ is, independently of the others, selected from hydrogen, alkyl (for example lower alkyl), aryl (for example phenyl or naphthyl, arylalkyl (for example benzyl), heteroaryl and heteroarylalkyl; A is selected from O, S and N$R^{50}$, where $R^{50}$ is selected from $R^d$ and cycloalkyl, or, alternatively, is taken together with $R^3$ such that $R^{50}$ and $R^3$, together with nitrogen atom to which they are attached, form a three-to seven-membered ring; and $R^3$ is a group that, together with A, metabolizes under the conditions of use to yield an intermediate group of the formula —$CR^dR^d$AH, where $R^d$ and A are as previously defined. As mentioned above, compounds of structural formula (VI) and (VIa) in which the $R^P$ groups are of the formula —$CR^dR^d$-AH spontaneously hydrolyze in vivo to yield the active 2,4-pyrimidinediamine drug.

The mechanism by which the $R^3$ group metabolizes to yield intermediate group —$CR^dR^d$-A-H is not critical, and can be caused by, for example, hydrolysis under the acidic conditions of the stomach, and/or by enzymes present in the digestive tract and/or tissues or organs of the body. Indeed, the $R^3$ group(s) can be selected to metabolize at a particular site within the body. For example, many esters are cleaved under the acidic conditions found in the stomach. Prodrugs designed to cleave chemically in the stomach to the active 2,4-pyrimidinediamine can employ progroups including such esters. Alternatively, the progroups may be designed to metabolize in the presence of enzymes such as esterases, amidases, lipolases, phosphatases including ATPases and kinase etc., to yield the intermediate group of formula —$CR^dR^d$-A-H. Progroups including linkages capable of metabolizing in vivo to yield such an intermediate group are well-known, and include, by way of example and not limitation, ethers, thioethers, silylethers, silylthioethers, esters, thioesters, carbonates, thiocarbonates, carbamates, thiocarbamates, ureas, thioureas, carboxamides, etc. In some instances, a "precursor" group that is oxidized by oxidative enzymes such as, for example, cytochrome P450 of the liver, to a metabolizable group, can be selected.

The identity of the $R^3$ group can also be selected so as to impart the prodrug with desirable characteristics. For example, lipophilic groups can be used to decrease water solubility and hydrophilic groups can be used to increase water solubility. In this way, prodrugs specifically tailored for selected modes of administration can be obtained. The $R^3$ group can also be designed to impart the prodrug with other properties, such as, for example, improved passive intestinal absorption, improved transport-mediated intestinal absorption, protection against fast metabolism (slow-release prodrugs), tissue-selective delivery, passive enrichment in target tissues, targeting-specific transporters, etc. Groups capable of imparting prodrugs with these characteristics are well-known, and are described, for example, in Ettmayer et al., 2004, J. Med. Chem. 47(10:2393-2404), the disclosure of which is incorporated by reference. All of the various groups described in these references can be utilized in the prodrugs described herein.

In some embodiments, $R^3$ is selected from —$R^f$, —C(O)$R^f$, —C(O)N$R^fR^f$ and —Si$R^fR^fR^f$, where the $R^f$ groups are selected so as to impart the prodrugs with desired bioavailability, cleavage and/or targeting properties. In a specific embodiment, the $R^f$ groups are selected to impart the prodrug with higher water-solubility than the underlying active 2,4-pyrimidinediamine drug. Thus, in some embodiments, the $R^f$ groups are selected such that they, taken together with the heteroatom or group to which they are bonded, are hydrophilic in character. Such hydrophilic groups can be charged or uncharged, as is well-known in the art. As specific examples, the $R^f$ groups may be selected from hydrogen, optionally substituted lower alkyl, optionally substituted lower heteroalkyl, optionally substituted lower cycloalkyl, optionally substituted lower heterocycloalkyl, optionally substituted (C6-C10) aryl, optionally substituted 5-10 membered heteroaryl, optionally substituted (C7-C18) arylalkyl and optionally substituted 6-18 membered heteroarylalkyl. The nature of any present substituents can vary widely, as is known in the art. In some embodiments any present substituents are, independently of one another, selected from $R^b$, defined above.

In a specific embodiment, the progroups on the prodrugs of formula (I) and/or (Ia) are of the formula —$CR^dR^d$-A-$R^3$, where $R^3$ is selected from —$(CH_2)_i$—$R^b$, —C(O)$R^a$, —C(O)—$(CH_2)_i$—$R^b$, —C(O)O—$R^a$ and —C(O)O—$(CH_2)_i$—$R^b$, where X, $R^a$, $R^b$ and $R^d$ are as previously defined, and i is an integer ranging from 0 to 6. Specific, non-limiting, examples of exemplary water-solubility increasing progroups include by the way of example and not limitation, hydrophilic groups such as alkyl, arylk, arylalkyl, or cycloheteroalkyl groups substituted with one or more of an amine, alcohol, a carboxylic acid, a phosphorous acid, a sulfoxide, a sugar, an amino acid, a thiol, a polyol, a ether, a thioether and a quaternary amine salt.

One important class of progroups includes progroups that contain a phosphate group, for example, phosphate-containing progroups of the formula —$(R^dR^d)_y$—O—P(O)(OH)$_2$, where $R^d$ is as defined above and y is an integer ranging from 1 to 3, typically 1 or 2. In a specific embodiment, each $R^d$ is, independently of the others, selected from hydrogen, substituted or unsubstituted lower alkyl, substituted or unsubstituted (C6-C14) aryl and substituted or unsubstituted (C7-C20) arylalkyl.

While not intending to be bound by any theory of operation, it is believed that such phosphate-containing progroups $R^P$ act as substrates for both alkaline and acid phosphatase enzymes, leading to their removal from the prodrugs under physiological conditions of use. As alkaline phosphatases are abundant in the digestive tract of humans, phosphate-containing progroups $R^P$ that can be cleaved in the presence of alkaline phosphatases are particularly suitable for formulating phosphate-containing prodrugs intended for oral administration. Specific examples of phosphate-containing progroups $R^P$ suitable for use in prodrugs intended for oral administration include, but are not limited to, groups of the formula —$(CR^dR^d)_y$—O—P(O)(OH)$_2$ in which each $R^d$ is, independently of the others, selected from hydrogen and unsubstituted lower alkanyl. Exemplary embodiments of such phosphate-containing progroups include, but are not limited to, —CH$_2$—O—P(O)(OH)$_2$ and —CH$_2$CH$_2$—O—P(O)(OH)$_2$.

Although phosphate-containing prodrugs suitable for oral administration are of interest, skilled artisans will appreciate that prodrugs including phosphate-containing progroups $R^P$ can be administered via other routes of administration, as phosphatases are distributed throughout the body. For example, exemplary prodrug Compound 4 has been found to metabolize to the active drug Compound III in in vitro experiments carried out with rat plasma, as well as with rat hepatic and intestinal microsomal preparations, indicating that phosphatases are also present in plasma. Thus, the only requirement is that the particular phosphate-containing progroup $R^P$ selected should be removable under the conditions of intended use.

While not intending to be bound by any theory of operation, it is believed that when y is 1, phosphate-containing prodrugs, such as those according to structural formula (VIa), are metabolized to the active 2,4-pyrimidinediamine compound via the corresponding hydroxymethylamine. This metabolism is illustrated in FIG. 13A. Referring to FIG. 13A, removal of phosphoric acid from phosphate prodrug 16 via enzymatic hydrolysis yields the corresponding hydroxymethylamine 18, which undergoes hydrolysis in vivo to yield formaldehyde and active 2,4-pyrimidinediamine compound 10.

Referring to FIG. 13B, when y is 2, it is believed that in vivo hydrolysis of phosphate prodrug 26 yields active 2,4-pyrimidinediamine 10 and enol phosphate, which then hydrolyses in vivo to acetaldehyde and phosphoric acid.

Referring again to FIG. 13A, skilled artisan will appreciate that while hydroxymethylamine 18 metabolizes under physiological conditions to yield active 2,4-pyrimidinediamine compound 10, it is stable at pH 7 and can therefore be prepared and administered as a hydroxyalkyl-containing prodrug of active compound 10. Thus, in some embodiments of the prodrugs of structural formula (VI), $R^P$ is a hydroxyalkyl-containing progroup of the formula —$CR^dR^d$—OH, where $R^d$ is as previously defined. In a specific exemplary embodiment, $R^P$ is —CH$_2$OH.

Still referring again to FIG. 13A, skilled artisans will also appreciate that phosphate prodrugs can be generated by in vivo hydrolysis of phosphate ester prodrugs, such as phosphate ester prodrugs 20 and/or by in vivo oxidation of phosphite prodrugs, such as phosphite prodrugs 24. Such phosphate ester and phosphite prodrugs can in turn be generated by either in vivo oxidation or hydrolysis of phosphite ester prodrugs such as phosphite ester prodrugs 22. The corresponding phosphate ester, phosphite and phosphite ester prodrugs of phosphate prodrug 26 are illustrated in FIG. 13B as compounds 30, 34 and 32, respectively. Thus, as will be appreciated by skilled artisans, prodrugs that include precursors of phosphates that can metabolize into phosphate groups in vivo are also included in the present invention.

In some embodiments of such prodrugs, the phosphorous-containing progroup $R^P$ comprises a phosphite group. A specific exemplary embodiment of such phosphite-containing prodrugs includes prodrug compounds in which the progroup $R^P$ is of the formula —$(CR^dR^d)_y$—O—P(OH)(OH), where $R^d$ and y are as previously defined.

In other embodiments of such prodrugs, the phosphorous-containing progroup $R^P$ comprises an acyclic phosphate ester or phosphite ester group. Specific exemplary embodiments of such acyclic phosphate ester and phosphite ester prodrugs include progroups $R^P$ of the formula —$(CR^dR^d)_y$—O—P(O)(OH)(OR$^e$), —$(CR^dR^d)_y$—O—P(O)(OR$^e$)$_2$, —$(CR^dR^d)_y$—O—P(OH)(OR$^e$) and —$(CR^dR^d)_y$—O—P(OR$^e$)$_2$, where $R^e$ is selected from substituted or unsubstituted lower alkyl, substituted or unsubstituted (C6-C14) aryl (e.g., phenyl, naphthyl, 4-lower alkoxyphenyl, 4-methoxyphenyl), substituted or unsubstituted (C7-C20) arylalkyl (e.g., benzyl, 1-phenylethan-1-yl, 2-phenylethan-1-yl), —$(CR^dR^d)_y$—OR$^f$, —$(CR^dR^d)_y$—O—C(O)R$^f$, —$(CR^dR^d)_y$—O—C(O)OR$^f$, —$(CR^dR^d)_y$—S—C(O)R$^f$, —$(CR^dR^d)_y$—S—C(O)OR$^f$, —$(CR^dR^d)_y$—NH—C(O)R$^f$, —$(CR^dR^d)_y$—NH—C(O)OR$^f$ and —Si(R$^d$)$_3$, wherein each R$^f$ is, independently of the others, selected from hydrogen, unsubstituted or substituted lower alkyl, substituted or unsubstituted (C6-C14) aryl, and substituted or unsubstituted (C7-C20) arylalkyl, and $R^d$ and y are as previously defined.

In still other embodiments, phosphorous-containing prodrugs that include phosphate precursors are prodrugs in which the phosphorous-containing progroup $R^P$ comprises a cyclic phosphate ester of the formula

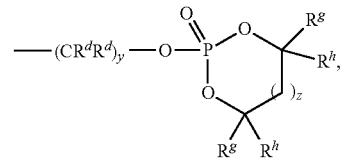

where each R$^g$ is, independently of the others, selected from hydrogen and lower alkyl; each R$^h$ is, independently of the others, selected from hydrogen, substituted or unsubstituted lower alkyl, substituted or unsubstituted lower cycloheteroalkyl, substituted or unsubstituted (C6-C14) aryl, substituted or unsubstituted (C7-C20) arylalkyl and substituted or unsubstituted 5-14 membered heteroaryl; z is an integer ranging from 0 to 2; and $R^d$ and y are as previously defined.

In still other embodiments, phosphorous-containing prodrugs that include phosphate precursors are prodrugs in which the phosphorous-containing progroup $R^P$ comprises a cyclic phosphite ester of the formula

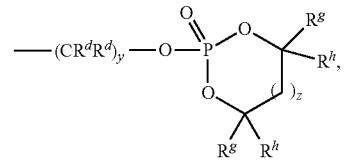

where R$^g$, R$^h$, $R^d$, y and z are as previously defined.

In some embodiments, the substituents R$^h$ on such cyclic phosphate ester and phosphite ester prodrugs are selected such that the progroup is metabolized in vitro by esterase enzymes. Specific examples of such phosphate ester and phosphite ester progroups include those in which each $R^h$ is, independently of the others, selected from hydrogen, lower alkyl, methyl, ethyl and propyl. In some embodiments, such progroups are selected from

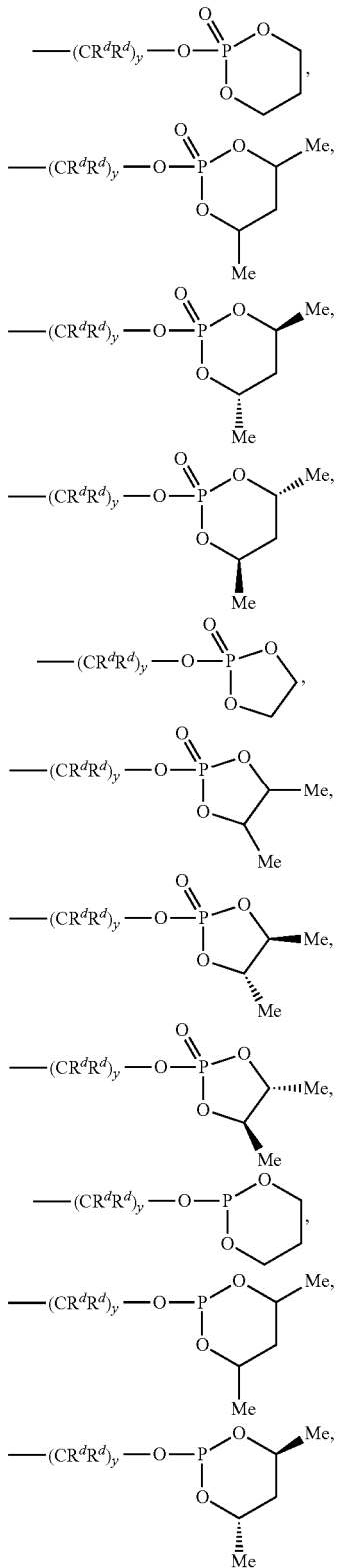

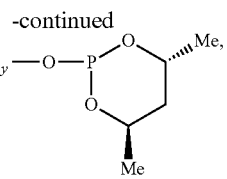

Many of these phosphate esters and phosphite esters are acid label and, when administered orally, metabolize to the corresponding phosphates and phosphites under the acidic conditions of the stomach and/or gut.

Thus, in the phosphorous-containing prodrugs described herein, the identity of the particular phosphorous-containing progroups $R^P$ employed can be selected to tailor the prodrugs for particular modes of delivery, etc.

The suitability of any particular progroup $R^P$ for a desired mode of administration can be confirmed in biochemical assays. For example, if a prodrug is to be administered by injection into a particular tissue or organ, and the identities of the various phosphatases expressed in the tissue or organ are known, the particular prodrug can be tested for metabolism in biochemical assays with the isolated phosphatase(s). Alternatively, the particular prodrug can be tested for metabolism to the active 2,4-pyrimidinediamine compound with tissue and/or organ extracts. Using tissue and/or organ extracts can be of particular convenience when the identity(ies) of the phosphatases expressed in the target tissues or organs are unknown, or in instances when the isolated phosphatases are not conveniently available. Skilled artisans will be able to readily select progroups $R^P$ having metabolic properties (such as kinetics) suitable for particular applications using such in vitro tests. Of course, specific prodrugs could also be tested for suitable metabolism in in vitro animal models.

In some embodiments, the prodrugs are prodrugs according to structural formula (VI) or (VIa) that have one or more features selected from:
(i) $R^5$ is fluoro;
(ii) $R^2$ is a phenyl optionally substituted with one or more of the same or different $R^8$ groups;
(iii) $R^2$ is 3,4,5-tri(loweralkoxy)phenyl;
(iv) $R^2$ is 3,4,5-trimethoxyphenyl;
(v) Y or $Y^1$ is O; $Z^1$ is CH, $Z^2$ is N; $R^{17}$ and $R^{18}$ are each methyl; and $R^{19}$ and $R^{20}$ are taken together to form an oxogroup; and
(vi) $R^P$ is a hydroxyalkyl-containing progroup of the formula —$CH_2OH$, or a phosphate-containing progroup of the formula —$(CR^dR^d)_y$—O—$P(O)(OH)_2$, or a phosphate ester, phosphite or phosphite ester analog thereof, wherein y is 1 or 2 and each $R^d$ is, independently of the others, selected from hydrogen and unsubstituted lower alkyl, or (vii) $R^P$ is selected from —CH$_2$OH, CH$_2$—SH, —CH$_2$—NH$_2$, —CH$_2$—NHR$^{50}$, —CH$_2$—N(R$^{50}$)$_2$, —CH$_2$-A-R$^f$, —CH$_2$-A-C(O)R$^f$, —CH$_2$-A-C(O)OR$^f$ and —CH$_2$-A-C(O)NR$^f$R$^f$, where A, R$^{50}$ and R$^f$ are as previously defined.

In some embodiments, the prodrugs of structural formulae (I) and (Ia) have two or three of the above-delineated features. In one specific embodiment, the prodrugs have features (i), (iii) and (v). In another specific embodiment, the prodrugs have features (i), (iv) and (v). In still another specific embodiment, the prodrugs have features (i), (iii), (v) and (vi) or (vii). In still another specific embodiment, the prodrugs have features (i), (iv), (v) and (vi) or (vii). In still another specific embodiment, $R^P$ is a phosphate-containing progroup of the formula —(CR$^d$R$^d$)$_y$—O—P(O)(OH)$_2$.

In all of the compounds described herein that include substituent alternatives that may be substituted, such as, for example, some of the substituent alternatives delineated for R$^d$, R$^e$, R$^f$, R$^g$, R$^h$, R$^i$ and R$^j$, the substitutions are typically, independently of one another, selected from amongst the R$^b$ groups described in connection with structural formula (VI). In a specific embodiment, any present substitutions are, independently of one another, selected from hydroxyl, lower alkoxy, (C6-C14) aryloxy, lower alkoxyalkyl, methoxymethyl, methoxyethyl, ethoxymethyl, ethoxyethyl and halogen.

Those of skill in the art will appreciate that many of the prodrugs described herein, as well as the various prodrug species specifically described and/or illustrated herein, may exhibit the phenomena of tautomerism, conformational isomerism, geometric isomerism and/or optical isomerism. For example, the prodrugs may include one or more chiral centers and/or double bonds and as a consequence may exist as stereoisomers, such as double-bond isomers (i.e., geometric isomers), enantiomers and diasteromers and mixtures thereof, such as racemic mixtures. As another example, the prodrugs may exist in several tautomeric forms, including the enol form, the keto form and mixtures thereof As the various compound names, formulae and drawings within the specification and claims can represent only one of the possible tautomeric, conformational isomeric, optical isomeric or geometric isomeric forms, it should be understood that the invention encompasses any tautomeric, conformational isomeric, optical isomeric and/or geometric isomeric forms of the prodrugs having one or more of the utilities described herein, as well as mixtures of these various different isomeric forms. In cases of limited rotation around the 2,4-pryimidinediamine moiety, atrop isomers are also possible and are also specifically included in the compounds of the invention.

Moreover, skilled artisans will appreciate that when lists of alternative substituents include members which, owing to valency requirements or other reasons, cannot be used to substitute a particular group, the list is intended to be read in context to include those members of the list that are suitable for substituting the particular group. For example, skilled artisans will appreciate that while all of the listed alternatives for R$^b$ can be used to substitute an alkyl group, certain of the alternatives, such as =O, cannot be used to substitute a phenyl group. It is to be understood that only possible combinations of substituent-group pairs are intended.

The prodrugs described herein may be identified by either their chemical structure or their chemical name. When the chemical structure and the chemical name conflict, the chemical structure is determinative of the identity of the specific prodrug.

Depending upon the nature of the various substituents, the prodrugs described herein may be in the form of salts. Such salts include salts suitable for pharmaceutical uses ("pharmaceutically-acceptable salts"), salts suitable for veterinary uses, etc. Such salts may be derived from acids or bases, as is well-known in the art.

In one embodiment, the salt is a pharmaceutically acceptable salt. Generally, pharmaceutically acceptable salts are those salts that retain substantially one or more of the desired pharmacological activities of the parent compound and which are suitable for administration to humans. Pharmaceutically acceptable salts include acid addition salts formed with inorganic acids or organic acids. Inorganic acids suitable for forming pharmaceutically acceptable acid addition salts include, by way of example and not limitation, hydrohalide acids (e.g., hydrochloric acid, hydrobromic acid, hydriodic, etc.), sulfuric acid, nitric acid, phosphoric acid, and the like. Organic acids suitable for forming pharmaceutically acceptable acid addition salts include, by way of example and not limitation, acetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl)benzoic acid, cinnamic acid, mandelic acid, alkylsulfonic acids (e.g., methanesulfonic acid, ethanesulfonic acid, 1,2-ethanedisulfonic acid, 2-hydroxyethanesulfonic acid, etc.), arylsulfonic acids (e.g., benzenesulfonic acid, 4-chlorobenzenesulfonic acid, 2-naphthalenesulfonic acid, 4-toluenesulfonic acid, camphorsulfonic acid, etc.), 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

Pharmaceutically acceptable salts also include salts formed when an acidic proton present in the parent compound is either replaced by a metal ion (e.g., an alkali metal ion, an alkaline earth metal ion or an aluminum ion) or coordinates with an organic base (e.g., ethanolamine, diethanolamine, triethanolamine, N-methylglucamine, morpholine, piperidine, dimethylamine, diethylamine, etc.).

The prodrugs described herein, as well as the salts thereof, may also be in the form of hydrates, solvates and N-oxides, as are well-known in the art. Unless specifically indicated otherwise, the expression "prodrug" is intended to encompass such salts, hydrates, solvates and/or N-oxides. Specific exemplary salts include, but are not limited to, mono- and disodium salts, mono- and di-potassium salts, mono- and dilithium salts, mono- and di-alkylamino salts, monomagnesium salts, mono-calcium salts and ammonium salts.

The prodrugs described herein, as well as intermediates therefor, may be synthesized via a variety of different synthetic routes using commercially available starting materials and/or starting materials prepared by conventional synthetic methods. Suitable exemplary methods that may be routinely used and/or adapted to synthesize active 2,4-pyrimidinediamine compounds can be found in U.S. Pat. No. 5,958,935, U.S. application Ser. No. 10/355,543 filed Jan. 31, 2003 (US2004/0029902A1), international application Serial No. PCT/US03/03022 filed Jan. 31, 2003 (WO 03/063794), U.S. application Ser. No. 10/631,029 filed Jul. 29, 2003 (US2007/0060603), international application Serial No. PCT/US03/24087 (WO2004/014382), U.S. application Ser. No. 10/903, 263 filed Jul. 30, 2004 (US2005/0234049), and international application Serial No. PCT/US2004/24716 (WO2005/016893), the disclosures of which are incorporated herein by reference. These active 2,4-pyrimidinediamine compounds can be used as starting materials to synthesize the prodrugs. Specific examples describing the synthesis of phosphate prodrug Compound 4, as well as a synthetic intermediate therefor, are provided in the Examples section. All of the prodrugs described herein may be synthesized by routine adaptation of this method.

For example, some embodiments of prodrugs according to structural formula (VI) and/or (VIa) can be prepared by reacting the corresponding active 2,4-pyrimidinediamine (i.e., compounds according to structural formulae (I) and/or (Ia) in which each $R^P$ is hydrogen) with an aldehyde or a ketone to give an α-hydroxymethyl amine, which can then be reacted with an electrophile to yield a prodrug. An exemplary synthesis of this type is illustrated in Scheme (VI), below:

a strong acid catalyst, or a carbon-bearing halide (e.g., $CH_3Br$), to yield the corresponding ether derivatives (e.g., compounds in which $R^3$ is $R^f$, where $R^f$ is as previously defined).

Reacting α-hydroxymethylamines 14a, 14b and 14c with a carboxylic acid in the presence of a strong acid catalyst or a carboxylic acid anhydride or a carboxylic acid halide (e.g. with an appropriate acid scavenger) yields the corresponding ester derivatives (e.g., compounds in which $R^3$ is —$C(O)R^f$, where $R^f$ is as defined above).

Reaction of α-hydroxymethylamines 14a, 14b and 14c with a haloformate ester (e.g., Cl—$C(O)OCH_3$) yields the corresponding carbonate derivatives (e.g., compounds in which $R^3$ is —$C(O)OR^f$, where $R^f$ is as previously defined).

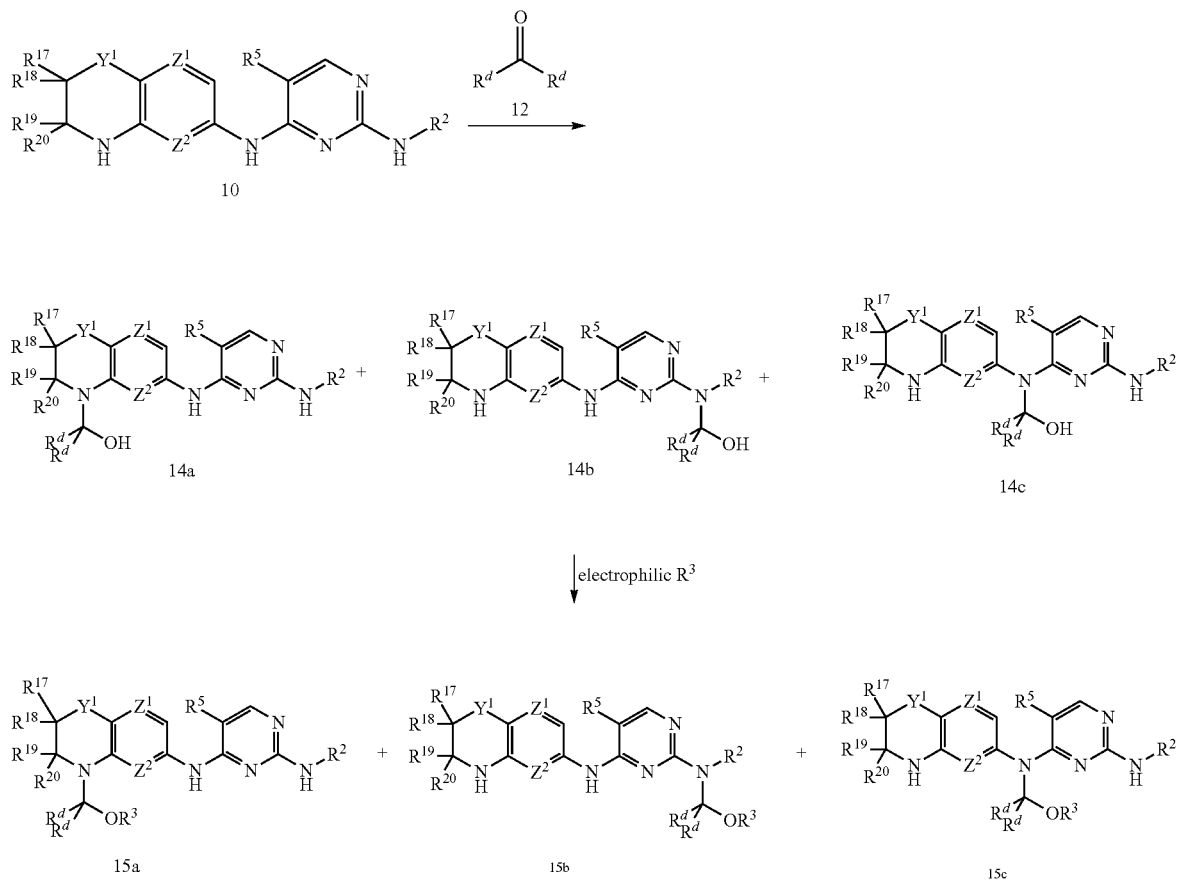

In Scheme (I), $Y^1$, $Z^1$, $Z^2$, $R^2$, $R^5$, $R^{17}$, $R^{18}$, $R^{19}$ and $R^{20}$ are as defined for structural formula (VI) or (VIa). $R^3$ and $R^d$ are as defined in the text, supra. According to Scheme (VI), active 2,4-pyrimidinediamine 10 is reacted with ketone 12 to yield a mixture of four products: unreacted starting material 10 (not illustrated) and compounds 14a, 14b and 14c. At this stage, the products can be isolated from one another using standard chromatographic techniques. Reaction with electropholic $R^3$ yields prodrugs 15a, 15b and 15c.

As illustrated above, α-hydroxymethylamines 14a, 14b and 14c can be converted into a variety of different types of prodrugs 15a, 15b and 15c. For example, the α-hydroxymethylamines can be reacted with an alcohol in the presence of Reaction of α-hydroxymethylamines 14a, 14b and 14c with a haloformamide (e.g., Cl—$C(O)N(CH_3)_2$) yields the corresponding carbamate or urethane derivatives (e.g., compounds in which $R^3$ is —$C(O)NR^fR^f$, where $R^f$ is as previously defined).

As will be recognized by skilled artisans, other hydroxyl protecting groups could also be used, including, for example, the various different hydroxyl protecting groups described in Green & Wuts, "*Protective Groups in Organic Chemistry*," 2d Edition, John Wiley & Sons, New York, pp. 10-142, the disclosure of which is incorporated herein by reference.

Alternatively, prodrugs according to structural formulae (VI) and (VIa) can be synthesized by nucleophilic substitution of the corresponding phosphate esters. An example of this synthetic route is illustrated in Scheme (II), below:

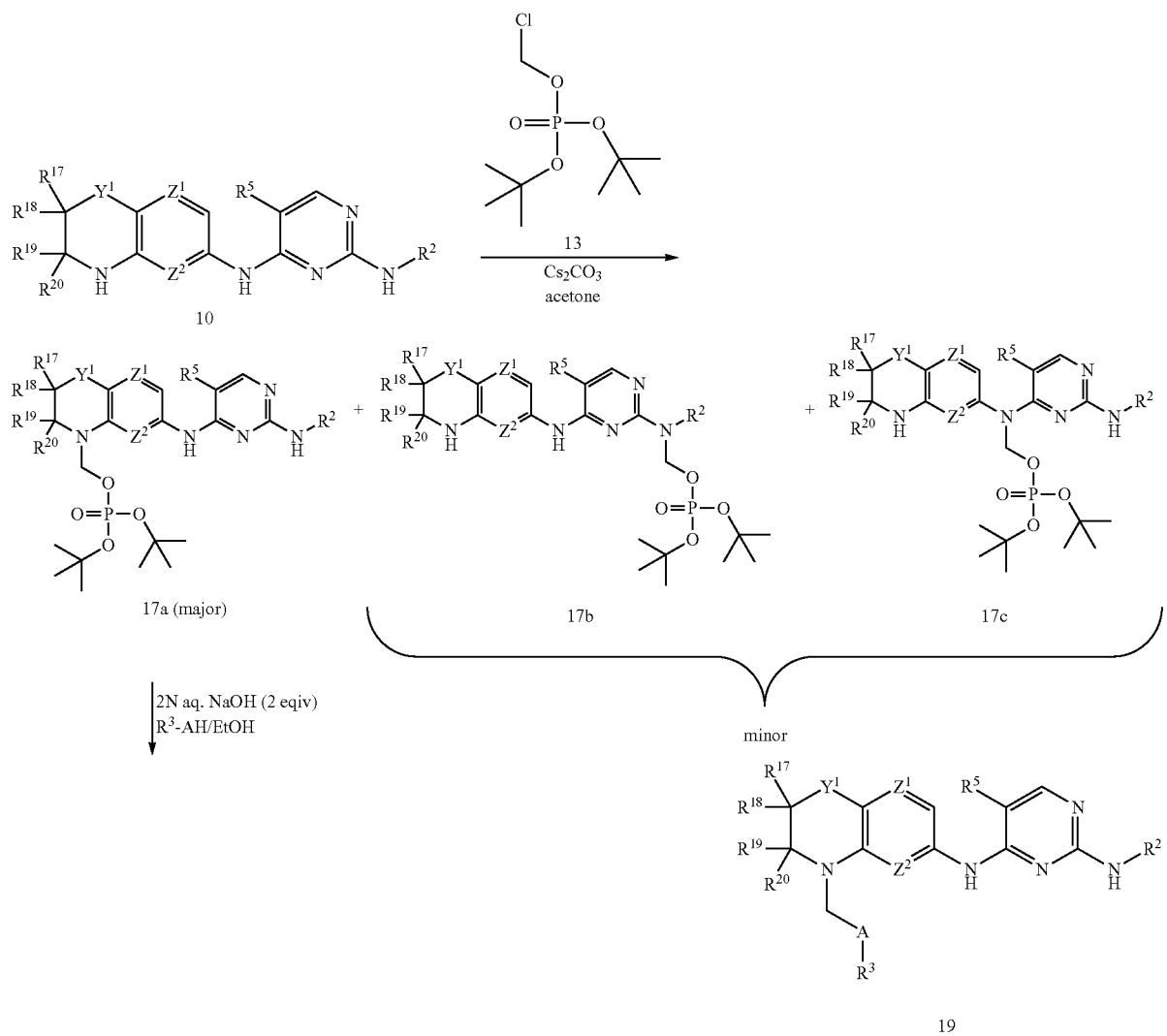

According to Scheme (II), active 2,4-pyrimidinediamine 10 is reacted with di-tert-butyl chloromethylphosphate 13 in the presence of cesium carbonate to yield a mixture of four products: unreacted starting material 10 (not illustrated) and phosphate esters 17a, 17b and 17c, which are themselves prodrugs as described herein. When $R^2$ is 3,4,5-trimethoxyphenyl phosphate ester 17a is the major product. Reaction of this phosphate ester 17a with $R^3$-AH (where A is O, S, or $NR^{56}$), yields prodrug 19. The minor phosphate esters 17b and 17c can be similarly reacted to yield the corresponding prodrugs.

Di-tert-butyl chloromethyl phosphate 13 can be prepared from di-tert-butyl phosphate as illustrated in Scheme (III), below:

-continued

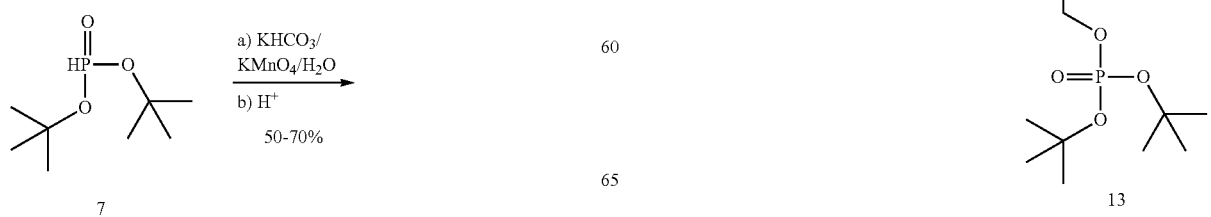

According to Scheme (III), di-tert-butyl phosphate 9 is obtained from the corresponding di-tert-butyl phosphite 7 as described in Krise et al., 1990, J. Med. Chem. 42:3793-3794. Reaction of phosphate 9 with chloromethyl chlorosulfate 11 (available from Synergetica, Inc., Sicklerville, N.J. 08081) as described in Mantyla et al., 2002, Tet. Lett. 43:3793-3794 yields di-tert-butyl chloromethyl phosphate 13, which can be used in Scheme (II), above, crude without purification.

Although the Schemes illustrated above depict the synthesis of prodrugs that include a single progroup, prodrugs having a plurality of progroups could be obtained by adjusting the number of equivalents of reagent 12 or 13 used.

As another alternative to Scheme (I), hydroxymethylamine 14a can be prepared in a two-step process by first reacting active 2,4-pyrimidinediamine 10 with a bis functional electrophile, such as, for example, chloro-iodomethane (I—$CH_2$Cl), to yield a chloro-methyl intermediate, which can then be hydroxylated by reaction with basic hydroxide or reacted with various nucleophilic reagents such as alkoxides, amines or sulfide to make $R^P$. Specific conditions for carrying out reactions of this type that can be used to synthesize the prodrugs described herein, for example, in Bansal et al., 1981, J. Pharm. Sci. 70(8):850-854 and Bansal et al., 1981, J. Pharm. Sci. 70(8):855-857 , the disclosures of which are incorporated herein by reference.

An exemplary synthetic route that can be used to synthesize an exemplary phosphate prodrug 16 according to structural formula (VIa) is illustrated in Scheme (IV), below. This method may be routinely adapted to synthesize the full range of phosphate prodrugs described herein.

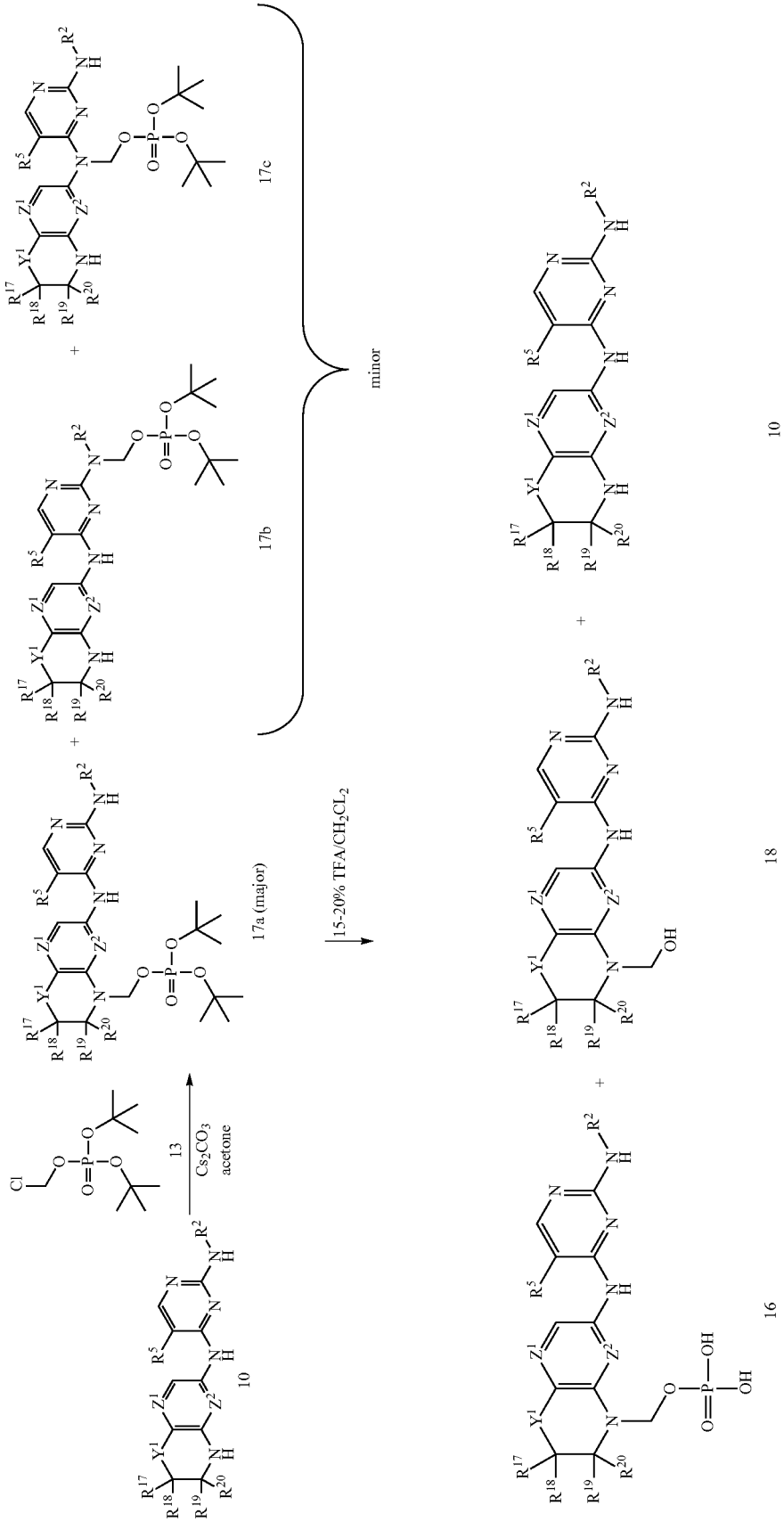
Scheme (IV)

In Scheme (IV), $Y^1$, $Z^1$, $Z^2$, $R^2$, $R^5$, $R^{17}$, $R^{18}$, $R^{19}$ and $R^{20}$ are as defined for structural formula (VI) or (VIa). According to Scheme (IV), active 2,4-pyrimidinediamine 10 is reacted with di-tert-butyl chloromethylphosphate 13 in the presence of cesium carbonate to yield a mixture of four products: unreacted starting material 10 (not illustrated) and compounds 17a, 17b and 17c. When $R^2$ is 3,4,5-trimethyoxyphenyl, compound 17a is the major product. At this stage, the major product can be isolated from the minor products using standard chromatographic techniques. Removal of the tert-butyl groups yields a mixture of desired product 16 and impurities 18 and 10. The desired product 16 can be isolated using standard techniques.

An alternative method of obtaining phosphate prodrug 16 is illustrated in Scheme (V); below.

uct 17a and minor products 17b and 17c. Major product 17a can be isolated via crystallization (see the Examples section for suitable conditions, dissolved in a mixture of acetic acid and water (4:1 AcOH:H$_2$O) and heated to 65° C. for approximately 3 hr to yield phosphate prodrug 16 as the major product.

Although Schemes (IV) and (V) illustrate the synthesis of a phosphate prodrug in which the phosphate progroup is —CH$_2$—O—P(O)(OH)$_2$, skilled artisans will appreciate that phosphate prodrugs including other phosphate progroups could be readily obtained according to the same methods by using the appropriate reagent 13. Phosphate ester prodrugs, phosphite prodrugs and phosphite ester prodrugs can also be synthesized via routine adaptation of the methods using the appropriate phosphate ester, phosphite and phosphite ester halides 13. Exemplary methods for synthesizing cyclic phos-

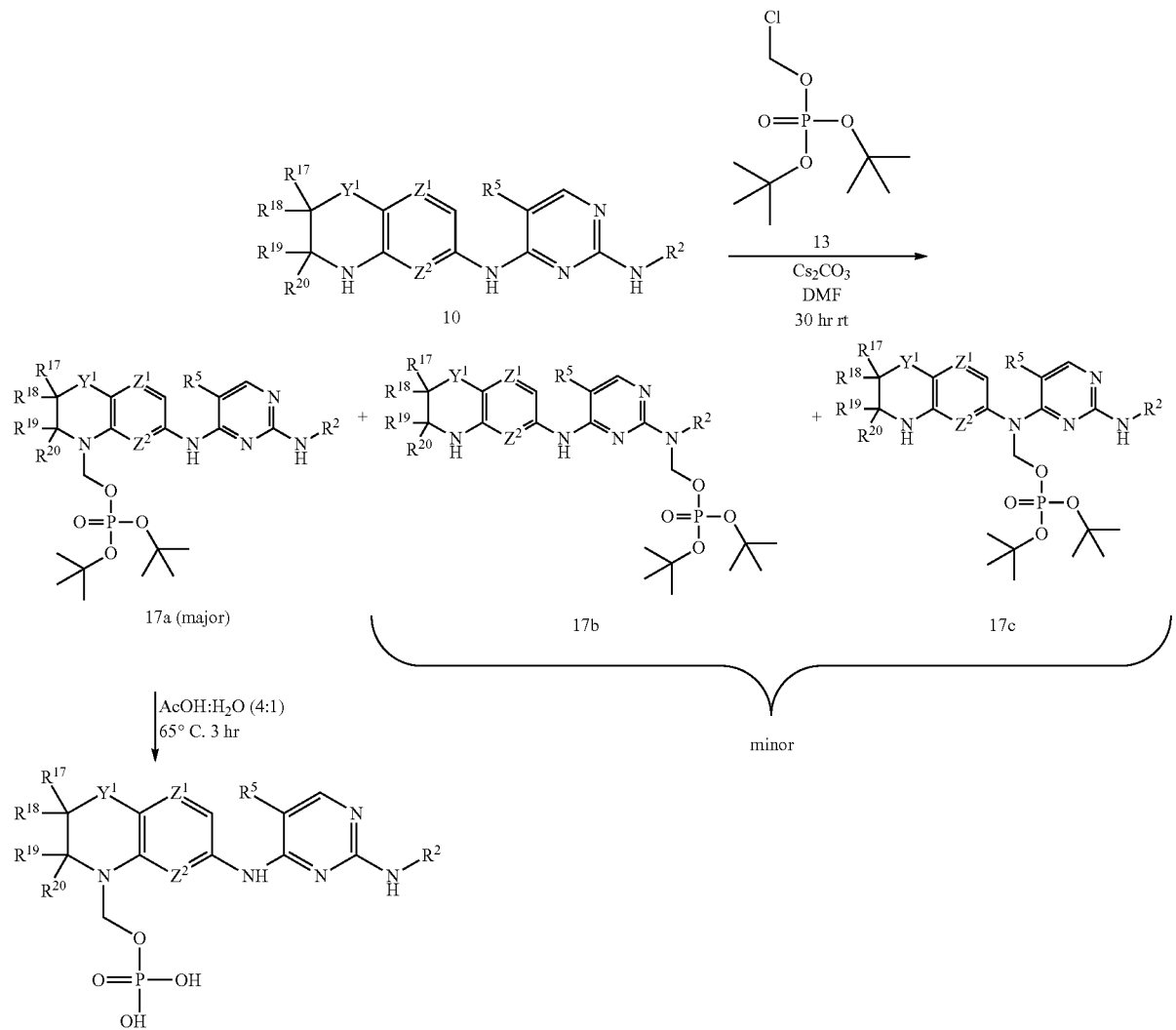

According to Scheme (V), the reaction of active 2,4-pyrimidinediamine 10 again yields a mixture of four products: unreacted pyrimidinediamine 10 (not illustrated) major product phate ester prodrugs, which can be used as prodrugs in the various methods described herein, or converted into phosphate prodrugs, are illustrated in FIG. 15. Moreover, while Schemes (I) and (III) depict compound 16 as being the desired product, prodrugs having progroups at other positions within the prodrug molecule could be readily obtained by isolating, for example minor product 17a or 17b and/or by adjusting the number of equivalents of reagent 13 used.

Referring to FIG. 15, diols 21 are converted to the corresponding cyclic phosphates 23 using literature procedures as depicted. Cyclic phosphates 23 are converted to the corresponding chloromethyl phosphate esters 25 in any of the three ways depicted. Compound III is converted to cyclic phosphate ester derivatives 27, 29, and 31, via addition of 25 under conditions as previously described for the synthesis of compounds 17a-c. Cyclic phosphate ester derivatives 27, 29, and 31, are converted to the corresponding phosphate derivatives via treatment under acidic conditions as described for the synthesis of compound 16, or via hydrogenation using, for example, palladium catalyst.

Skilled artisans will recognize that in some instances, the active 2,4-pyrimidinediamine compounds used as starting materials may include functional groups that require protection during synthesis. The exact identity of any protecting group(s) used will depend upon the identity of the functional group being protected, and will be apparent to these of skill in the art. Guidance for selecting appropriate protecting groups, as well as synthetic strategies for their attachment and removal, may be found, for example, in Greene & Wuts, *Protective Groups in Organic Synthesis*, 3d Edition, John Wiley & Sons, Inc., New York (1999) and the references cited therein (hereinafter "Greene & Wuts").

Preferably, the prodrugs will metabolize into active compound(s) that will provide therapeutic or prophylactic benefit without causing substantial toxicity. Toxicity of the active and other metabolites, as well as the unmetabolized prodrug may be determined using standard pharmaceutical procedures. The dose ratio between toxic and therapeutic (or prophylactic) effect is the therapeutic index. Prodrug(s) that exhibit high therapeutic indices are preferred.

In some embodiments, the Syk inhibitor compounds do not include specific embodiments described in U.S. Application No. 60/494,008, filed Aug. 7, 2003, U.S. Application 60/572,534, filed May 18, 2004; and U.S. application Publication No. 2005/0113398 (Ser. No. 10/913,270). All patent applications and publications are incorporated herein by reference in their entirety. These compounds are also disclosed in Appendixes 1, 2, and 3 of U.S. Provisional Application No. 60/672,648, filed Apr. 18, 2005, the entire contents of which is incorporated herein by reference.

Exemplary embodiments of Syk or Syk/Flt-3 kinase inhibitors based on 2,4-pyrimidinediamines pyrimidinediamines for the treatment of the conditions and disorders described herein include, among others, compounds having the following structures:

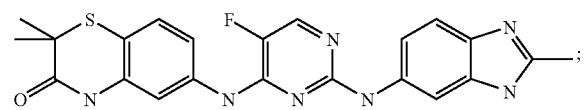

II

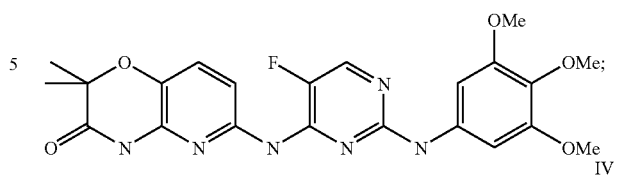

III

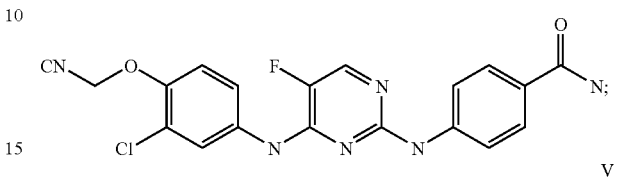

IV

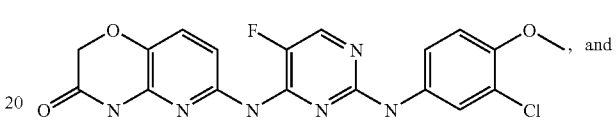

V and various salts, hydrates, solvates, and N-oxides thereof.
—Other exemplary embodiments of Syk or Syk/Flt-3 kinase inhibitors based on 2,4-pyrimidinediamines include, among others, N4-(2,2-Dimethyl-3-oxo-4H-5-pyrid[1,4]oxazin-6-yl)-5-fluoro-N2-(3,4,5,-trimethoxyphenyl)-2,4-pyrimidinediamine (Compound VI); N4-(2,2-dimethyl-4-[(dihydrogen phosphonoxy)methyl]-3-oxo-5-pyrido[1,4]oxazin-6-yl)-5-fluoro-N2-(3,4,5-trimethoxyphenyl)-2,4-pyrimidinediamine (Compound VII); and various the salts (e.g., calcium salts, etc.), hydrates, solvates, and N-oxides thereof.

In some embodiments, the Syk kinase inhibitors can comprise compounds based on pyridine, pyrimidine, or triazine rings, as described in published U.S. application No. 2004/0106615 and PCT publication WO 2004/016597, which are incorporated herein by reference. Generally, the pyridine, pyrimidine, or triazine ring is directly attached to a 6-membered aryl or heteroaryl ring having 0-3 nitrogen atoms. —In some embodiments, the Syk kinase inhibitor comprises compounds based on amino- or diaminotriazoles, as described in PCT publications WO 2005/013982 and WO 2004/046120, and published U.S. Application No. 20040214817, incorporated herein by reference. The aminotriazole compounds typically have substituents on the nitrogen atoms at the 3 or 4 position of the triazole ring, or the amino substituent on the ring. Exemplary aminotriazoles include, among others, aminotriazole pyridines and aminotriazole pyrimidines (see, e.g., WO 2005/013982). Similarly, diaminotrazole compounds that inhibit kinases have substituents on one of the amino groups, and a substituent on the nitrogen atom at the 3 or 4 position of the triazole ring. Exemplary kinase inhibitors based on diaminotriazoles are described in WO2004/046120 and US 20040214817.

In some embodiments, the Syk kinase inhibitor comprises compounds based on azaindoles, as described in U.S. Pat. No. 6,849,641, published U.S. Patent Application No. 2004/0053931, and PCT publication WO 03/000688, all of which are incorporated herein by reference. U.S. Pat. No. 6,849,641 describes 3-heteroarylideneazaindolin-2-one compounds. Similarly, U.S. Patent Application No. 2004/0053931 and PCT Publication No. WO 03/000688 describes azaindole compounds, among others, in which the pyrrolopyridine has aromatic or heterocyclic substituents (e.g., benzyl or indolyl) at the 2 or 3 position.

In other embodiments, the Syk kinase inhibitor comprises compounds based on benzimidazoles, as described in published U.S. Patent Application No. 2004/0048868 and PCT publication WO 03/020698, both of which are incorporated herein by reference in their entirety. These compounds typically have substituents at the 1 and 2 positions of the imidazolyl along with additional subsitutions on the benzyl ring. Exemplary substituent at the 2 position is an aryl or heteroaryl, such as a pyrazolyl, triazolyl, imidazolyl, indolyl, indazolyl, thienopyrazolyl, tetrahydroindazolyl, tetrahydrocyclopentapyrazolyl, dihydrofuropyrazolyl, oxodihydropyridazinyl, tetrahydropyrrolopyrazolyl, oxotetrahydropyrrolopyrazolyl, tetrahydropyranopyrazolyl, tetrahydropyridinopyrazolyl, or oxodihydropyridinopyrazoly group.

In some embodiments, the Syk kinase inhibitor comprises compounds based on thiazoles, as described in U.S. Pat. No. 6,762,179, published U.S. Patent Application Nos. 2003/0119856 and 2005/0004152, and PCT Publication No. WO 02/096905, which are incorporated herein by reference. Exemplary thiazole based inhibitors are 4-thiazolylpyrimidines in which the pyrmidine has substituents at the 2 and 4 positions. Typically, the group at the 2 position is a unsubstituted or substituted amine. Substituents on the amine are generally monocylic and heterocyclic rings, such as subsituted phenyl, indanyl, naphthyl, pyrimidinyl, or pyridyl rings.

In some embodiments, the Syk kinase inhibitor comprises compounds based on pyrrolopyrimidines, as described in published U.S. Patent Application No. 2004/0142947 and PCT Publication Nos. WO 03/000695 and WO 2004/016597, which are incorporated herein by reference. In some embodiments, the pyrrolopyrimidine is attached to the 3 position of an indole ring. Generally, the indole has substituents on the 1 and/or 5 positions. An additional subsituent can be present at the 4 position of the pyrrolopyrimidine, including, among others, cyano, halo, hydroxy, nitro, aryl, heteroaryl, alkenyl, or alkynyl.

In some embodiments, the Syk kinase inhibitor comprises compounds based on indazoles, as described in published U.S. Patent Application No. 2005/0009876 and U.S. Pat. No. 6,534,524, which are incorporated herein by reference in their entirety. U.S. Pat. No. 6,534,524 discloses inhibitor compounds in which the indazole has substituents at the 3 and/or 5 positions. Substituents at the 3 position are, among others, an unsubstituted aryl or substituted or unsubstituted heteroaryl, or CH=CH—R or CH=N—R, where R is a substituted or unsubstituted alkyl, alkelnyl, cycloalkyl, heterocycloalkyl, aryl or heteroaryl. Substituents at the 5 position are, among others, substituted or unsubstituted aryl, heteroaryl, or a Y—X, where Y is O, S, C=CH$_2$, C=O, S=O, SO$_2$, alkylidene, NH, N-alkyl, where R$^1$ is a substituted or an unsubstituted aryl, heteroaryl, or N—R, where R is alkyl, cycloalkyl, heterocycloalkyl, aryl, heteroaryl, alkoxyl, or dialkylamide. Similarly, U.S. Patent Application No. 2005/0009876 discloses compounds in which the indazole has substituents at the 3 and/or 5 positions of the indazole. At the 3 position, a substituted or unsubstituted aryl, or a heteroaryl or heterocycle fused to a phenyl is attached via an allkyl, such as an alkanyl, alkenyl, or alkynyl. Substituents at the 5 position are, among others, halogen, hydroxy, carboxy, alkyl, alkoxy, haloalkyl, acyloxy, thioalkyl, sulfinylalkyl, sulfonylalkyl, hydroxyalkyl, aryl, substituted aryl, arylalkyl, substituted arylalkyl, heterocycle, substituted heterocycle, substituted or unsubstituted heterocycloalkyl, ester, amide, cyano, or substituted or unsubstituted amine.

In some embodiments, the Syk kinase inhibitor comprises bicyclic compounds, as described in U.S. Pat. No. 6,573,295, published U.S. Patent Application No. 2002/0062031, and PCT publication WO 00/27802, all which are incorporated herein by reference. In some of these embodiments, an unsubstituted or substituted benzyl is fused to a cycloalkyl, which is also substituted or unsubstituted. An exemplary cycloalkyl is a heptenyl. Exemplary bicyclic inhibitor compounds are {4-[2-(7-carbamoyl-8-cylohexylmethoxy-2,3,4,5-tetrahydrobenzo[b]oxepin-(S)-5-ylcarbamoyl)-2-phenylacetylaminoethyl]-2-phosphono-phenyl}-phosphonic acid; {4-[(S)-2-Acetylamino-2-(3-carbamoyl-2-cycycloxylmethoxy-6,7,8,9-tetrahydro-5H-benzocyclohepten-(S)-5-ylcarbamoyl)-ethyl]-phenoxy}-acetic acid; and (4-[(s)-2-Acetylamino-2-(3-carbamoyl-2-cycycloxylmethoxy-6,7,8,9-tetrahydro-5H-benzocyclohepten-(S)-5-ylcarbamoyl)-ethyl]-2-carboxymethyl-phenoxy-acetic acid.

In other embodiments, the kinase inhibitors comprises chromenone oxime compounds as described in published U.S. Patent Application No. 2004/0198750 and PCT publication WO 2004/092154, which are incorporated herein by reference. Generally, substituents are on the 2 and 7 positions of the chromenone oxime nucleus.

Other kinase inhibitors compounds include, substituted heterocycles (e.g., thiazole, oxazole, isoxazole, diazole, oxadiazole, dioxazole, furan, and pyridine) described in PCT publication WO99/47529, and substituted aryl or 5- or 6-membered heteraryl rings as described in PCT publication No. WO 2004/085388; and sulfonamides as described in Lai et al., 2003, *Bioorg Med Chem Lett.,* 13(18):3111-4. Other kinase inhibitor compounds will be apparent to the skilled artisan, and can be tested for Syk kinase inhibitory activity using the guidance provided herein.

Compounds can be tested in various biochemical and cellular assays for their inhibitory effect on Syk and/or Flt-3 kinase. Syk kinase phosphorylates LAT and PLC-γ1, which leads to, among other things, degranulation in mast and/or basophil cells. Syk kinase activity is also observed in response to T-cell receptor stimulation. It is to be understood that any of these activities can be used to confirm the activity of the Syk inhibitor compounds. In some embodiments, the Syk kinase assay is a degranulation assay based on measurement of granule content release following stimulation with anti-IgE. These assays include, for example, measurement of tryptase, histamine, leukotriene LTC4, or hexosaminidase release. In other embodiments, the activity is determined by contacting an isolated Syk kinase, or an active fragment thereof with an inhibitor compound in the presence of a Syk kinase substrate (e.g., a synthetic peptide or a protein that is known to be phophorylated by Syk in a signaling cascade) and assessing whether the Syk kinase phosphorylates the substrate. Alternatively, the assay can be carried out with cells that express a Syk kinase. The cells can express the Syk kinase endogenously or they can be engineered to express a recombinant Syk kinase. The cells can optionally also express the Syk kinase substrate. Cells suitable for performing such confirmation assays, as well as methods of engineering suitable cells will be apparent to those of skill in the art. Suitable Syk kinase substrate include, by way of example and not limitation, human band 3 protein (Wang et al., 1999, *J Biol Chem.* 274(45), 32159-32166); protein kinase C (Kawakami et al., 2003, *Proc Natl Acad Sci USA,* 100(16):9470-5), tubulin (Peters et al., 1996, *J. Biol. Chem.* 271:4755), cortactin (Maruyama et al., 1996, *J. Biol. Chem.* 271:6631), and p50/HS1 (Ruzzene et al., 1996, *Biochemistry* 35:1527). Specific examples of biochemical and cellular assays suitable for confirming the activity of the Syk inhibitor compounds are described in Fox et al., 1998, *Protein Science,* 7:2249, U.S. application Ser. No. 10/631,029, WO 2004/014382, and references cited therein, all of which are incorporated herein by reference.

Activation of Flt-3 kinase leads to autophosphorylation as well as phosphorylation of a number of cellular substrates, including, among others, of Src homology 2 (SH2)-containing inositol-5-phosphatase (SHIP) and a 100-kD protein in monocytic THP-1 cells; phosphorylation of Shc and Cbl in myeloid cells; β-arrestin; SH2-containing tyrosine phosphatase, and Cbl-b in pro-B cells (see, e.g., Rottapel et al., 1994, *Oncogene* 9:1755-1765; Zhang et al., 1999, *J. Leukoc. Biol.* 65:372-380). In some embodiments, the activity of Flt-3 kinase can be determined by used of antibodies to the phosphorylated form of Flt-3 kinase (i.e., autophosphorylation assay; Kiyoi et al. 1998, *Leukemia* 12:1333-1337). In some embodiments, the activity can be determined by contacting an isolated Flt-3 kinase, or an active fragment thereof, with an inhibitor compound in the presence of an Flt-3 kinase substrate (e.g., a synthetic peptide or a protein that is known to be phophorylated by Flt-3 in a signaling cascade). Alternatively, the assay can be carried out with cells that express an Flt-3 kinase, either endogenously or they being engineered to express a recombinant Flt-3 kinase (e.g., Yamamoto et al., 2001, *Blood* 97(8):2434-2439). The cells can optionally also express the Flt-3 kinase substrate. In some embodiments, the Flt-3 expressing cells can be examined for activation of various downstream targets described above, such as, for example, phospholipase C-(PLC), the p85 subunit of phosphatidylinositol 3'-kinase (PI3K), SHC, SHP-2, SHIP, GRB2, VAV, Fyn kinase, Src kinase, StatS signal transducing protein, and ERK.

Determining the effect of the inhibitor compounds on cell proliferation can use any number of in vitro and in vivo assays. For example, proliferating cells can be suitably cultured in vitro and treated with the compounds of interest. Proliferative capacity in the cell populations can be determined use dye staining (e.g., trypan blue dye-exclusion; 3-4, 5-dimethylthiazol-2,5-diphenyltetrazolium (MTT); and annexin V), or cell sorting techniques (e.g., fluorescence activated cell sorting with propidium iodide). In vivo assays for cell proliferation can be based on transplantation of tumor cells into experimental animals followed by administration of the inhibitor compounds. These and other methods of assessing cell proliferation will be apparent to the skilled artisan.

6.3 Dosages

The active compound(s), or compositions thereof, can be used in an amount effective to treat or prevent the particular disease being treated. The compound(s) can be administered therapeutically to achieve therapeutic benefit or prophylactically to achieve prophylactic benefit. By therapeutic benefit is meant eradication or amelioration of the underlying cell proliferative disorder being treated, e.g., lymphoid neoplasm, myeloid neoplasm, viral associated tumors, and/or eradication or amelioration of one or more of the symptoms associated with the underlying disorder such that the patient reports an improvement in condition, notwithstanding that the patient can still be afflicted with the underlying disorder. Therapeutic benefit also includes halting or slowing the progression of the disease, regardless of whether improvement is realized.

For prophylactic administration, the active compound can be administered to a patient at risk of developing a disorder characterized by, caused by or associated with aberrant cell proliferation, such as the various disorders previously described above. For instance, if a patient is diagnosed with a tumor but there is no indication of metastasis, the inhibitor compounds can be administered prophylactically to inhibit tumor metastasis.

The amount of inhibitor compound(s) administered will depend upon a variety of factors, including, for example, the particular indication being treated, the mode of administration, whether the desired benefit is prophylactic or therapeutic, the severity of the indication being treated and the age and weight of the patient, the bioavailability of the particular active compound, etc. Determination of an effective dosage is well within the capabilities of those skilled in the art.

Initial dosages can be estimated initially from in vitro assays. For example, an initial dosage for use in animals can be formulated to achieve a circulating blood or serum concentration of compound that inhibits Syk or Flt-3 sufficient to reduce the cell proliferation or invasiveness of the tumor cells. Alternatively, an initial dosage for use in animals can be formulated to achieve a circulating blood or serum concentration of active compound that is equal to or greater than the $IC_{50}$ as measured in Syk kinase or Flt-3 inhibition assay. Calculating dosages to achieve such circulating blood or serum concentrations taking into account the bioavailability of the particular inhibitor compound is well within the capabilities of skilled artisans. For guidance, the reader is referred to Fingl and Woodbury, "General Principles," In: *The Pharmaceutical Basis of Therapeutics,* Chapter 1, pp. 1-46, 1975, and the references cited therein. Initial dosages can also be estimated from in vivo data, such as animal models. Animal models useful for testing the efficacy of compounds to treat or prevent diseases characterized by, caused by or associated with Syk kinase or Flt-3 kinase activity are described herein.

Dosage amounts will typically be in the range of from about 1 mg/kg/day to about 100 mg/kg/day, 200 mg/kg/day, 300 mg/kg/day, 400 mg/kg/day or 500 mg/kg/day, but can be higher or lower, depending upon, among other factors, the activity of the inhibitory compound, its bioavailability, the mode of administration and various factors discussed above. Dosage amount and interval can be adjusted individually to provide plasma levels of the active compound(s) which are sufficient to maintain therapeutic or prophylactic effect. In cases of local administration or selective uptake, such as local topical administration, the effective local concentration of active compound(s) may not be related to plasma concentration. Skilled artisans will be able to optimize effective dosages without undue experimentation.

The compound(s) can be administered once per day, a few or several times per day, or even multiple times per day, depending upon, among other things, the indication being treated and the judgment of the prescribing physician.

Preferably, the active compound(s) will provide therapeutic or prophylactic benefit without causing substantial toxicity. Toxicity of the active compound(s) can be determined using standard pharmaceutical procedures. The dose ratio between toxic and therapeutic (or prophylactic) effect is the therapeutic index. Active compound(s) that exhibit high therapeutic indices are preferred.

6.4 Administration

When used to treat or prevent cell proliferative disorders, the Syk or Syl/Flt-3 inhibitor compounds can be administered singly, as mixtures of one or more active compounds or in mixture or combination with other agents useful for treating such diseases and/or symptoms associated with such diseases. The active compounds can be administered per se or as pharmaceutical compositions.

Pharmaceutical compositions comprising the active compounds of the invention can be manufactured by means of conventional mixing, dissolving, granulating, dragee-making levigating, emulsifying, encapsulating, entrapping or lyophilization processes. The compositions can be formulated in a conventional manner using one or more physiologically acceptable carriers, diluents, excipients or auxiliaries which facilitate processing of the active compounds into preparations which can be used pharmaceutically. The actual pharmaceutical composition administered will depend upon the mode of administration. Virtually any mode of administration can be used, including, for example topical, oral, systemic, inhalation, injection, transdermal, etc.

The active compound can be formulated in the pharmaceutical compositions per se, or in the form of a pharmaceutically acceptable salt. As used herein, the expression "pharmaceutically acceptable salt" means those salts which retain substantially the biological effectiveness and properties of the active compound and which is not biologically or otherwise undesirable. Such salts can be prepared from inorganic and organic acids and bases, as is well-known in the art. Typically, such salts are more soluble in aqueous solutions than the corresponding free acids and bases.

For topical administration, the active compound(s) can be formulated as solutions, gels, ointments, creams, suspensions, etc. as are well-known in the art.

Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the active compound(s) in aqueous or oily vehicles. The compositions can also contain formulating agents, such as suspending, stabilizing and/or dispersing agent. The formulations for injection can be presented in unit dosage form, e.g., in ampules or in multidose containers, and can contain added preservatives.

Alternatively, the injectable formulation can be provided in powder form for reconstitution with a suitable vehicle, including but not limited to sterile pyrogen free water, buffer, dextrose solution, etc., before use. To this end, the active compound(s) can be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well known in the art with, for example, sugars or enteric coatings.

Liquid preparations for oral administration can take the form of, for example, elixirs, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound.

For buccal administration, the compositions can take the form of tablets or lozenges formulated in conventional manner.

For rectal and vaginal routes of administration, the active compound(s) can be formulated as solutions (for retention enemas) suppositories or ointments containing conventional suppository bases such as cocoa butter or other glycerides.

For administration by inhalation, the active compound(s) can be conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g. gelatin for use in an inhaler or insufflator can be formulated containing a powder mix of the compound and a suitable powder base such as lactose or starch.

For prolonged delivery, the active compound(s) can be formulated as a depot preparation, for administration by implantation; e.g., subcutaneous, intradermal, or intramuscular injection. Thus, for example, the active ingredient can be formulated with suitable polymeric or hydrophobic materials (e.g., as an emulsion in an acceptable oil) or ion exchange resins, or as sparingly soluble derivatives; e.g., as a sparingly soluble salt.

Alternatively, transdermal delivery systems manufactured as an adhesive disc or patch which slowly releases the active compound(s) for percutaneous absorption can be used. To this end, permeation enhancers can be used to facilitate transdermal penetration of the active compound(s). Suitable transdermal patches are described in for example, U.S. Pat. Nos. 5,407,713.; 5,352,456; 5,332,213; 5,336,168; 5,290,561; 5,254,346; 5,164,189; 5,163,899; 5,088,977; 5,087,240; 5,008,110; and 4,921,475.

Alternatively, other pharmaceutical delivery systems can be employed. Liposomes and emulsions are well-known examples of delivery vehicles that can be used to deliver active compounds(s). Certain organic solvents such as dimethylsulfoxide (DMSO) can also be employed, although usually at the cost of greater toxicity.

The pharmaceutical compositions can, if desired, be presented in a pack or dispenser device which can contain one or more unit dosage forms containing the active compound(s). The pack can, for example, comprise metal or plastic foil, such as a blister pack. The pack or dispenser device can be accompanied by instructions for administration.

7. EXAMPLES

7.1 Example 1

Effect of Syk Inhibitory Compound on Syk Induced Pre-B Cell Transformation

Experiments showing the inhibiton of proliferation of Syk-transformed cells by a Syk inhibitory compound are described in Wossning, T., Herzog, S., Köhler, F., Meixlsperger, S., Kulathu, Y., Mittler, G., Abe, A., and Jumaa, H., "The protein tyrosine kinase Syk is involved in malignant transformation and leukemia development," (manuscript in preparation). The experiments described in the manuscript are briefly summarized below.

Aberrant Syk variants resulting from chromosomal translocation Tel-Syk were tested for its abilty to transform pre-B cells by retrovirally transducing freshly isolated bone marrow pre-B cells with IRES-GFP vectors expressing Tel-Syk. Withdrawal of IL-7 from these cell cultures led to an enrichment of Tel-Syk-expressing cells and the generation of stable IL-7 independent cell lines, indicating that TEL-Syk expression can promote proliferation and transformation of pre-B cells. Transformation of the pre B cells by Tel-Syk activity was confirmed by injecting the TEL-SYK transduced cells into RAG/γC−/− mice, which led to animals presenting symptoms of myelodysplastic disease. The data show that Tel-Syk-expressing cells can proliferate rapidly in vivo, thereby inducing aggressive leukemia.

To test whether inhibition of Syk activity in the cells transformed with Tel-Syk block cell proliferation, the effect of Syk kinase inhibitor 2,4-pyrimidinediamine compound IV was tested in vitro by examining the DNA content of treated cells. Compound IV effectively blocked Syk-induced pre-B cell proliferation and permitted the pre B cells to differentiate, as indicated by expression of kappa light chain in these cells. The data show that Syk expression may be required for proliferation of leukemic cells and that block of Syk kinase activity can lead to inhibition of leukemic cell proliferation.

7.2 Example 2

Effect of Syk Inhibitors on Established Leukemias

To determine the effect of Syk inhibitor on proliferation of leukemic cells, several tumorigenic pre-B cell lines that induce leukemia after injection into mice were used. Because tumorigenic cells need the pre-B cell receptor (pre-BCR) for proliferation, and Syk is a critical protein for pre-BCR signaling cascade, it is expected that Syk inhibitors will inhibit proliferation of these tumorigenic pre-B cells. In one experiment, the ability of compound VI to block proliferation was examined using pre-B cells transduced with Myc expression vectors and cultured in the absence of IL-7. Cells were injected into RAG/γC-± mice to examine their ability to proliferate in vivo. The ability of VI to block proliferation was tested in vitro using the Myc transduced cell lines (FIG. 2A and FIG. 2B).

Figure 1A:
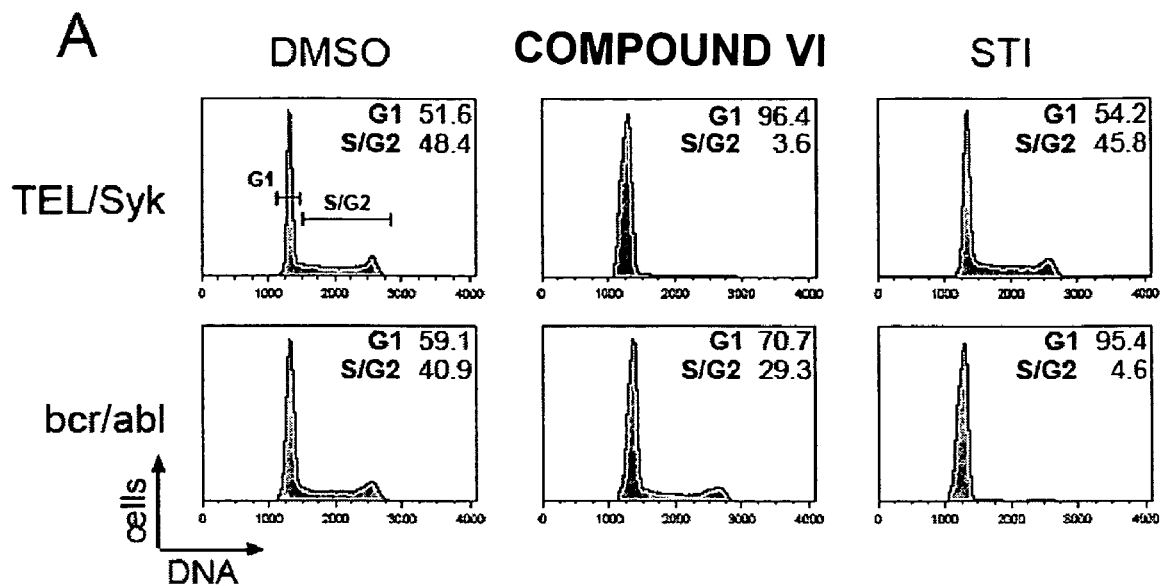
Figure 1B:
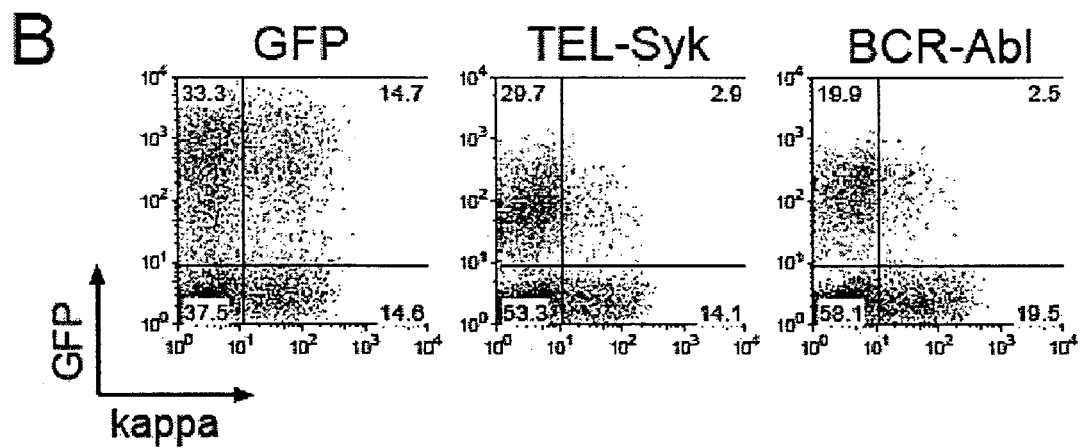
Figure 1C:
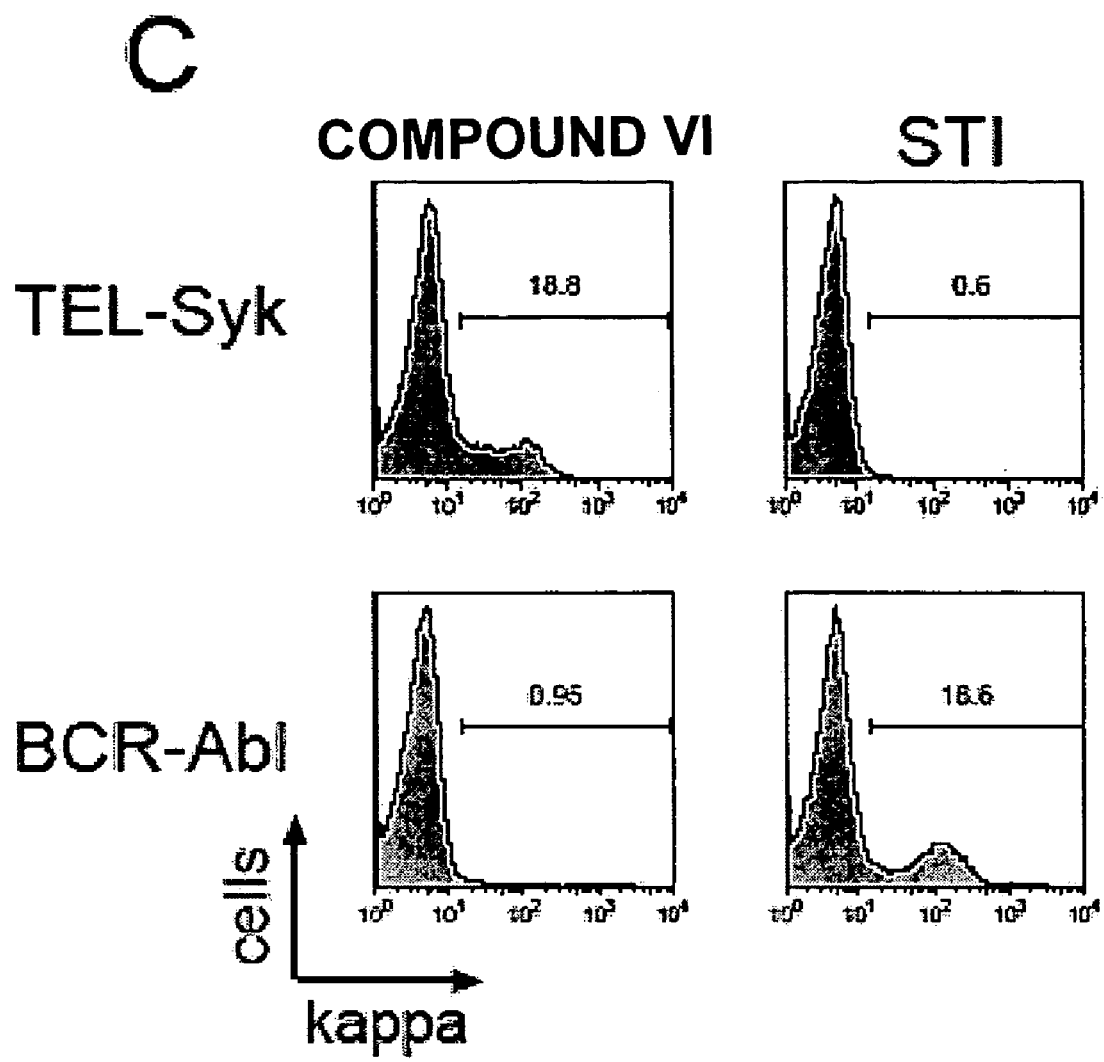
Figure 3A:
Figure 3B:
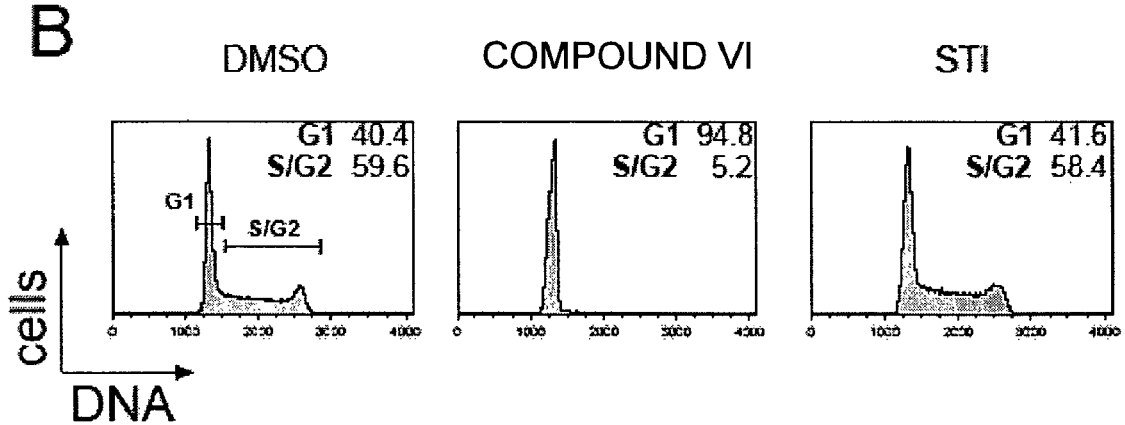

The ability of VI to block proliferation was also examined using tumorigenic SLP-65$^{-/-}$ pre-B cell line. Cells were injected into RAG/γC-± mice to examine their ability to proliferate in vivo. The ability of VI to block proliferation of the tumorigenic SLP-65$^{-/-}$ pre-B cell line was tested in vitro (FIG. 3A and FIG. 3B).

Other leukemic cell lines useful for examining the effect of Syk inhibitor compounds include, by way of example and not limitation, B-cell lymphoma cell line JM1 (ATCC No. CRL-10423), Hodgkin's lymphoma cell line RPMI-6666 (ATCC No. CCL-113), promyelocytic leukemia cell line HL-60 clone 15 (ATCC No. CRL-1964), Burkitt's lymphoma cell line GL-10 (ATCC No. CRL-2392), acute myelogenous leukemia cell line BDCM (ATCC No. CRL-2740), myelomonocytic leukemia (EBV) cell line CESS (ATCC No. TIB-190), EBV transformed plasmacytom/myeloma cell line MC-CAR (ATCC No. CRL-8083), and EBV transformed plasma cell leukemia cell line ARH-77 (ATCC No. CRL-1621).

7.3 Example 3

In Vivo Evaluation of the Calcium Salt Form of Compound VII, and Cell Titration in the MV4-11 Acute Myeloid Leukemia (AML) Intravenous Tumor Engraftment Model in NOD-SCID Immunocompromised Mice Pretreated With Cyclophamide The Flt-3 ITD mutation has been associated with poor prognosis and reduced remission rates in affected AML patients, making it an attractive target for therapeutic intervention. Studies have shown that mutant Flt-3 ITD receptors dimerize in a Flt-3 ligand-independent manner and autophosphorylation of the receptor results in constitutive activation, increased proliferation, and growth factor independence of the mutant cell. Initial studies showed that the calcium salt form VII reduced subcutaneous tumor growth and prolonged survival and reduced the tumor burden of mice intravenously (i.v.) inoculated with 5 million MV4-11 human acute myeloid leukemia cells having the Flt-3 ITD mutation. This study was carried out to demonstrate the efficacy of administering VII in inhibiting tumor growth through twice daily oral treatment with 40 mg/kg VII or vehicle on disease progression, severity, and survival resulting from i.v. injection of either 5 or 10 million MV4-11 leukemia cells into NOD-SCID mice pretreated with cyclophosphamide.

7.3.1 Experimental Methods

Cell Lines.

Leukemia Cell Lines: MV4-11 human acute myelogenous leukemia (AML) (Supplier: American Type Culture Collection (ATCC) were maintained and harvested by the Oncology group at Rigel. Cells were IMPACT tested on 11-30-04 and were negative for Ectromelia, EDIM, Hantaan, K virus, LCMV, LDEV, MAD, mCMV, MHV, MMV, MPV, MTV, *Mycoplasma* sp., Polyoma, PVM, REO3, Sendai, TMEV and GDVII.

Cell Line Maintenance: MV4-11 cells will be maintained in Iscove's modified Dulbecco's medium (ATCC® Number: 30-2005) with 4 mM L-glutamine adjusted to contain 1.5 g/L sodium bicarbonate, 80%; fetal bovine serum, 20% (GIBCO BRL, Carlsbad, Calif.), 1% Penicillin/Streptomycin (10,000 IU/ml and 10,000 ug/ml) (CellGro/MediaTech, Cat# 30-002-C1). Cells were harvested in logarithmic growth phase, washed, and injected in fresh medium. MV4-11 cells were inoculated at $5 \times 10^6$ or $10 \times 10^6$ cells per animal.

Pharmaceutics.

The specifications of the test articles and test formulations used in this study are listed on the formulations sheet below. Test article and vehicle formulations were made by the Pharmaceutics department before the start of dosing (Vehicle (Lot: 1024-15-01); 8 mg/mL VII calcium salt (Lot: 1024-15-03)). Calcium salt form VII was prepared at equivalent concentration of VI. Formulations were stored at 4° C., light protected, and were vortexed prior to use.

| Group | Test Article Id. Number | Formulation Details | Conc. (mg/mL) | Calculations Based on Free Base or Salt? | Formulation Required* (mL) | Free Base Equivalent (mg) | Dose Volume (mL/kg) | Dilution Factor* | Dose (mg/kg) | Days × Doses Per Day |
|---|---|---|---|---|---|---|---|---|---|---|
| | | In Vivo Evaluation of the kinetics of engraftment of MV411 leukemia (AML) cells administered i.v. in NOD-SCID immunocompromised mice and effect of Compound VII on level of engraftment. | | | | | | | | |
| 1 | Vehicle (0.1% CMC Na - 0.1% Methylparaben-0.02% Propylparaben-H2O) | Vehicle (0.1% CMC Na - 0.1% Methylparaben-0.02% Propylparaben-H2O) | 0.00 | 406 Free Base | 198.4 | 0.00 | 5.0 | 1 | 0 | 60 |
| 2 | Ca salt of VII | Vehicle (0.1% CMC Na - 0.1% Methylparaben-0.02% Propylparaben-H2O) | 16.00 | 406 Free Base | 198.4 | 3,174.00 | 5.0 | 1 | 80 | 60 |

Animals and Housing.

Approximately 10 week old, female NOD.CB17-Prkdc scid/J (NOD/SCID) mice (n=60; DOB May 30, 2005; rec'd Jul. 19, 2005 from Jackson Laboratories, Bar Harbor, Me.) were used for the study. NOD-SCID mice (stock # 001303) are exclusively available from The Jackson Laboratory and the multiple defects in innate and adaptive immunity unique to the NOD-SCID mouse provide an excellent in vivo environment for reconstitution with human hematopoietic cells. Approximately 50 mice were given cyclophosphamide and used for the in-life portion of this study, while the additional mice were used for non-tumored controls for the assessment of background staining for flow cytometric analysis of engraftment levels. Slightly older mice (>19 grams) were used (as compared to V050144) to try to avoid early deaths due to excessive weight loss following cyclophosphamide injection.

Animals were housed five per cage in Micro isolator cages in ventilated, HEPA-filtered cage racks (Alternative Design, Siloam Springs, Ariz.). Upon arrival, they were acclimated for at least four working days before use. Temperature was maintained at 72±5° F., relative humidity at 35-70%, and a 12-h light/dark cycle was used. The mice were fed certified rodent chow (Deans Feed, San Carlos, Calif.) ad libitum. Autoclaved R.O. drinking water was available ad libitum. Cages and food were autoclaved prior to use. All in-life procedures were approved by the Rigel IACUC.

NOD-SCID mice are both insulitis- and diabetes-free throughout life despite the NOD autoimmune diabetes-prone background, but there is a high incidence of thymic lymphomas in this congenic stock limiting the mean lifespan to only 8.5 months under specific pathogen-free conditions. The Emv-30 provirus on chromosome 11 results in high frequency of thymomas beginning at 5-6 months of age in the NOD-SCID (3, 4), (5), limiting the duration of experiments performed using NOD-SCID mice as recipients. In this experiment, all surviving mice were terminated when mice reached approximately 5 months of age (day 83 of the study) in order to limit the affects of spontaneous thymomas on outcome variables in this study.

Animal Procedures.

Bone Marrow Depletion for Enhanced Engraftment. At the end of the acclimatization period for the animals (>3 weeks in this study), mice were pretreated with sterile filtered (using a 0.22 µM syringe filter) Cyclophosphamide prepared in 0.9% sterile saline (Sigma, St Louis, Mo.) by intraperitoneal injection of 150 mg/kg/day for 2 days followed by a rest period of 72 hours prior to intravenous (i.v.) injection of leukemia cells via the lateral tail vein, as described below.

Tumor Inoculations: On day 0 of the study, mice were inoculated once by intravenous tail vein injection of 5 or 10 million human MV4-11 leukemia cells resuspended in 100 microliters of fresh media as outlined in Table 1.

Dosing: After mice were inoculated with human MV4-11 cells (day 0), dosing began on day 17 of the study. Mice were dosed orally (PO) twice daily (bid) for the duration of the study with either Vehicle or 40 mg/kg VII at 5 mL/kg dose volume with a minimum separation of 8 hours between doses Experimental Procedures Tumor Model: This study was designed to assess the effects of various doses of VII on tumor engraftment, disease progression, severity, and overall survival in a murine intravenous MV4-11 leukemia model using NOD-SCID immunocompromised mice as a host with cyclophosphamide pretreatment to enhance tumor engraftment. Historical data show variable tumor cell engraftment in bone marrow (BM) and peripheral blood mononuclear cells (PBMC), despite uniform lethality of tumor cell injection as determined by >20% weight loss, moribund status, severe loss of motility due to hindlimb paralysis or unexpected death as endpoints (Studies V050123 and V050144). In addition, cyclophosphamide was shown to be required for lethality in this model. Published studies showing median survival time of 51 days in vehicle control mice also demonstrate variable BM engraftment at sacrifice with a range of 2-19% human cells detected in the BM compartment.

This study was conducted in an effort to confirm a previous efficacy data from study, but also to determine if 5 or 10 million cell inoculations would yield similar inconsistencies in tumor cell engraftment in the bone marrow and peripheral blood or alter the resultant mortality in these mice. Since a detectable level of engraftment in some animals was observed as early as 4 weeks post tumor cell injection in pilot studies and historical efficacy data had been determined with this regimen, animals were treated orally (PO) with vehicle or R945788 calcium salt at 40 mg/kg on a twice per day (bid) schedule, every day beginning approximately 2 weeks after tumor cell injection. Animals were continued on this regimen until euthanized or until the end of the study. In this experiment, all surviving mice were terminated when mice reached approximately 5 months of age (day 83 of the study) in order to limit the affects of the spontaneous thymoma development, which can be seen in NOD-SCID mice beginning at approximately 5-6 months of age.

Study Design: On day 0 (Aug. 12, 2005), mice were i.v. injected with human MV4-11 cells in fresh medium at 5 or 10 million cells per mouse via the lateral tail vein. By day 3 post MV4-11 cell injection (on Aug. 15, 2005), one mouse was excluded due to early death from excessive body weight loss prior to randomization or treatment, potentially due to cyclophosphamide treatment. Remaining animals were randomized into treatment groups using body weights and dosing began on day 17 post cell injection (Aug. 29, 2005). Mean body weights of groups 1-4 were 20.66±0.43, 20.23±0.41, 20.18±0.54, and 20.88±0.59, respectively. Treatment groups are outlined in Table 1:

TABLE 1

Treatment Groups.

| Group | Cell Line | Cells per inoculation | Treatment | N= |
|---|---|---|---|---|
| 1 | MV4-11 | $5.0 \times 10^6$ | Vehicle | 12 |
| 2 | MV4-11 | $5.0 \times 10^6$ | 40 mg/kg VII | 12 |
| 3 | MV4-11 | $10.0 \times 10^6$ | Vehicle | 13 |
| 4 | MV4-11 | $10.0 \times 10^6$ | 40 mg/kg VII | 13 |
| | | | | 60* |

*Approximately n = 10 mice were obtained for nontumored control tissues, whole blood, or bone marrow Disease Progression and Disease Severity: Overall disease severity was determined from a combination of body weight loss, clinical observations, necropsy findings, and quantitation of tumor cell engraftment in selected tissues. Mice were weighed 2-3 times weekly and percent weight change calculated. At the first indication of morbidity, hind limb paralysis with apparent wasting, severe cachexia or weight loss greater than 20%, involving lethargy, ruffled fur etc, as outlined in IACUC Protocol Rigel 6-2002 "Efficacy of Novel Chemotherapeutics in Human/Mouse Tumor Xenograft Models", animals were removed from the study and euthanized. At sacrifice, animals were anesthetized with CO2 gas and blood was be collected by cardiocentesis. Blood from animal was transferred to K2EDTA coated Microtainer (lavendar top) tubes. Whole blood was placed indirectly on ice and processed for flow cytometric staining, as described in section below. To further assess disease severity, the location and description of palpable or suspected tumors on gross examination was carefully noted upon necropsy.

Tumor Cell Engraftment: To assess tumor burden, the distribution of MV4-11 tumor cells in the bone marrow and peripheral blood was determined in some of the mice at sacrifice via flow cytometric analysis using human and mouse surface marker staining.

The extent of tumor engraftment was evaluated in some mice by isolation of femurs and/or tibias at sacrifice. The bone marrow (BM) was aspirated into clean ependorff tube with 1 ml of cold PBS and retained on ice prior to flow staining. All remaining tissues or tumors were fixed in 10% buffered formalin for histopathology and immunohistochemistry (IHC). Peripheral blood was also obtained via cardiac puncture and put into K2EDTA coated Microtainer (purple) tubes. Red blood cells were lysed and samples washed, leaving only mononuclear cells (PBMC) for flow cytometric staining and analysis to determine tumor cell engraftment level.

To identify human MV4-11 tumor cells, BM and PBMC samples were stained with antibodies specific for mouse CD45, human CD45, human HLA, and human CD33 cell surface markers. Flow cytometric staining and analysis was then performed using this multiple marker strategy to identify and quantitate the percent of human MV4-11 leukemia cells present in randomly selected samples from VII treated and vehicle treated animals (Appendices 5 and 6). The percent of human MV4-11 cells was defined as the number of CD33+ HLA+ events out of total events (defined as the sum of human CD33+HLA+ and murine CD45+ events). Every effort was made to collect and analyze all animals in the study; however, due to the abrupt nature of death in vehicle treated mice in this model fewer samples were available for analysis and the number of animals was variable among the groups. For details of the cell preparation and flow staining and analysis procedure, see Appendices 5 and 6.

Statistical Analyses. Survival of mice was evaluated by Kaplan-Meier product limit method as a determination of the relative disease severity (n=18-20 animals/group) using the GraphPad Prism 4.0® software package. When possible, additional survival curve analyses including the Log Rank (Mantel-Haenszel) test (two-tailed p value) for curve comparison, hazard ratio for kinetics of survival, and the overall median survival were also calculated using Prism 4.0®. All surviving animals at study termination (day 83) were declared censored for statistical purposes in the Prism® analysis. The hazard statistic, defined as the slope of the survival curve, is a measure of how rapidly subjects are expiring; therefore, the reported hazard ratio is a comparison of the death rate between two groups. For example, if the hazard ratio is 2.0, then the rate of deaths in one group is twice that of the other group. In general, Prism 4.0® uses the standard calculations as detailed in D. G. Altman, Practical Statistics for Medical Research, 1991, Chapman and Hall. All results are expressed as mean ±SEM, unless otherwise indicated.

Additionally, the percent increase in life-span (% ILS) was determined using the calculated median day of death for each group compared to the vehicle control group using the following equation, where DOD is defined as day of death:

% ILS=(median $DOD_{treated}$−median $DOD_{vehicle}$)/median $DOD_{vehicle}$*100

Mice treated with 40 mg/kg VII had an undefined median survival time, since inadequate numbers of mice (<50%) had expired by study termination; therefore, calculations of % ILS assumed the maximum median survival of 80 days for this group and denoted as greater than the calculated value.

Engraftment data was analyzed using a One-way ANOVA, unless unequal variances were detected by the Bartlett's test. In this case, an Unpaired Two-tailed student's t test was performed using a Welch correction to account for unequal variances. Normalization of the percent CD33+HLA+ cells per total number of cells was performed. The mean percent tumor cells were determined using the following equation for each sample and then determining mean of these values. The total number of mouse cells was determined using a single cell surface marker, murine CD45 and the total number of human events was determined using dual human surface markers CD33 and HLA.

Percent Tumor cells=[(#CD33+HLA+ dual positive events)/(total # murine CD45+ and #CD33+HLA+ events)]*100

Due to the abrupt nature of death in vehicle treated mice in this model, few samples were available for analysis limiting our ability to achieve statistical significance. Sufficient sample size and random sampling was achieved with VII treated mice; therefore, comparisons were made between 20, 40, and 80 mg/kg VII treated mice and statistics performed as described above.

For categorical variables such as the total number of tumored animals per group, p values reflect the results of a comparison of treated versus vehicle groups using a two-tailed Fisher's Exact test with a 95% confidence interval also performed with GraphPad Prism 4.0® software package.

7.3.2 Results

Effect of Compound VII Treatment on Survival: Overall, animals treated with VII demonstrated prolonged survival and decreased numbers of palpable tumor masses on examination at necropsy. Vehicle treated mice inoculated with 5 million MV4-11cells had a median survival time of 54 days compared to 79 days in 40 mg/kg VII treated mice. Vehicle treated animals inoculated with 10 million tumor cells had a median survival time of 54 days with median day of death undefined for 40 mg/kg VII treated mice (>83 days). Mice treated with 40 mg/kg VII in the 10 million MV4-11 cell group had an undefined median survival time, since inadequate numbers of mice (<50%) had expired by study termination; therefore, calculations of % ILS assumed the maximum median survival of 83 days for this group and denoted as greater than the calculated value. Significant differences were seen in overall survival between VII treated and vehicle treated animals ((LogRank p<0.0022 and % ILS=45 % for 40 mg/kg VII with 5 million cells, LogRank p<0.0001 and % ILS>54% for 40 mg/kg VII with 10 million cells (assuming median DOD=83 for this group)).

TABLE 2

Median Day Of Death (DOD) And Percent Increase In Life-Span (% ILS) Of MV4-11 Tumor Bearing NOD-SCID Mice.

| MV4-11 Cell Titer | Treatment | Median DOD | % ILS* | Hazard ratio | Log Rank P value |
|---|---|---|---|---|---|
| 5E6 | Vehicle | 54 | NA | NA | NA |
| 5E6 | 40 mg/kg VII | 79 | 45 | 3.5 | 0.0022 |
| 10E6 | Vehicle | 54 | NA | NA | NA |
| 10E6 | 40 mg/kg VII | Undefined (>83) | >54%** | 7.6 | <0.0001 |

NA = not applicable
*as compared to vehicle control (median DOD = 54 days for both)
**assumes median day of death = 83

At day 83, there were no survivors in the vehicle treated groups. In contrast, mice from the VII treated group injected with 5 and 10 million MV4-11 cells had 5 and 9 surviving mice, respectively. Over 50% of the mice survived to Day 83 in the 10 million cell group treated with VII at 40 mg/kg, as compared to 0% survival of vehicle controls.

Effect of Compound VII on Disease Severity and Tumor Frequency and Distribution. Significant phenotypic differences were apparent when comparing the disease progression of vehicle and VII treated animals. Upon necropsy, palpable tumors in vehicle treated animals were observed in various lymph nodes (LN), on the spinal cord in lower region near inferior vena cava (possible LN), in the chest wall and surrounding the ribcage and sternum, near the trachea, jaw and throat area (presumably salivary gland and LN related). Tumors were also found on the kidney, ovary and heart. Additionally, very large tumors were found surrounding the bone in many cases in the shoulder, arms and legs. Some mice were noted to have soft and smooth brains or obvious tumor and one mouse had a severely enlarged eye that appeared to be tumored on necropsy, similar to several mice from MOLM 13 leukemia model in an intial study.

Vehicle treated animals manifested hind limb paralysis as early as 42 days post MV4-11 injection in the 5 million cell group and 48 days in the 10 million cell group. Upon necropsy, palpable tumors in vehicle treated animals were observed in similar locations as in previous studies. In total, 8 of 8 mice inoculated with 5 million tumor cells had palpable tumor masses on necropsy, with many mice having multiple anatomical sites identified as having tumors. Five mice from the vehicle treated group were found dead and 4 of these mice did not have a necropsy report due to advanced decay resulting in only 8 total necropsies in this group. By the end of the study (day 83 post MV4-11 implantation), 12 out of 12 vehicle treated animals had been terminated with 5 of the animals being found dead, 3 of them were moribund upon examination, 2 were sacrificed >20% body weight loss, and 2 were sacrificed for HLP associated with severe wasting.

Similarly, 11 of 12 mice had visible tumor masses with many having multiple sites identified in the vehicle treated mice inoculated with 10 million cells. A total of 1 vehicle treated animal was found dead and 1 had no necropsy performed due to advanced decay resulting in a total of 11 necropsies in this group. At study termination (day 83 post MV4-11 implantation), 13 out of 13 vehicle treated animals had been terminated with 1 of the animals being found dead, 3 of them were moribund upon examination, 7 had >20% body weight loss, and 2 were sacrificed for HLP associated with severe wasting.

In marked contrast, mice treated with 40 mg/kg VII demonstrated very few tumors with only 3 out of 11 total animals necropsied in the 5 million cell group and 7 out of 13 animals in the 10 million cell group showing some visible or palpable tumors. Most of these animals in the treated groups demonstrated much smaller tumors than vehicle treated animals. Tumors were located in similar anatomic sites and by study termination, 7 of 12 animals had been terminated in the 5 million cell 40 mg/kg VII treated group with 2 of the animals being found dead, 1 animal was moribund upon examination, 4 had >20% body weight loss, and none were sacrificed for HLP. Similarly, 40 mg/kg VII treated animals inoculated with 10 million Mv4-11 cells demonstrated very few tumors with some mice having enlarged salivary glands or slightly enlarged LN. At study termination, only 4 out of 13 of the 40 mg/kg VII treated mice had been terminated to date, with 3 mice having >20% body weight loss, and 1 animal found moribund upon examination. Overall, VII treated mice showed a significant reduction in total number of tumors, relative size of tumors observed at necropsy, and overall severity of disease in this study, with 40 mg/kg VII treatment showing similar efficacy seen in an initial study.

Effect of Compound VII on Engraftment of MV4-11 Tumor Cells in Bone Marrow (BM) and Peripheral Blood (PB): To correlate with a previous study, the level of MV4-11 engraftment in the bone marrow or peripheral blood was also examined in some animals at termination. Despite our best efforts, due to the abrupt nature of death in vehicle treated mice in this experiment some samples were unavailable for analysis. Unlike the intial study, a statistically significant decrease in mean percent MV4-11 tumor cells in the bone marrow and peripheral blood of VII treated animals at time of sacrifice was observed when compared to vehicle treated animals, regardless of the titer of cells inoculated (Table 3).

Vehicle treated mice inoculated with 5 million cells had 25% and 61% CD33+/HLA+ human tumor cells in BM (n=6) and PB (n=4), respectively. In contrast, VII treated mice inoculated with 5 million cells had 1% and 0.6% CD33+/HLA+ human tumor cells in BM (n=8) and PB (n=8), respectively (for BM p=0.13 and p=0.02 for PB for 40 mg/kg vs. vehicle control). The 10 million cell vehicle treated group had 13% and 45% CD33+/HLA+ human tumor cells in BM (n=8) and PB (n=8), respectively. In contrast, the 10 million cell VII treated group had 5% and 3% CD33+/HLA+ human tumor cells in BM (n=13) and PB (n=11), respectively (for BM p=0.05 and p=0.007 for PB for 40 mg/kg vs. vehicle control).

TABLE 3

Mean % MV4-11 Human Tumor Cells In Bone Marrow And Peripheral Blood of NOD-SCID Mice at Sacrifice.

| A. | Bone Marrow: Mean % Tumor Cells | | | | |
|---|---|---|---|---|---|
| | Naïve* (No cells) | 5 million MV4-11 Cells | | 10 million MV4-11 Cells | |
| | | Vehicle | 40 mg/kg VII | Vehicle | 40 mg/kg VII |
| Number of values (n=) | 6 | 6 | 8 | 9 | 13 |
| Mean % Tumor Cells* | 0.85 | 24.51 | 1.03 | 12.60 | 5.21 |
| Std. Deviation | 0.65 | 31.64 | 1.52 | 8.44 | 7.70 |
| Std. Error | 0.27 | 12.92 | 0.54 | 2.81 | 2.14 |
| Statistical Significance (versus Vehicle control)*** | — | — | p = 0.13 | — | p = 0.05 |

| B. | Peripheral Blood: Mean % Tumor Cells | | | | |
|---|---|---|---|---|---|
| | Naïve** no cells injected | 5 million MV4-11 Cells | | 10 million MV4-11 Cells | |
| | | Vehicle | 40 mg/kg VII | Vehicle | 40 mg/kg VII |
| Number of values (n=) | 6 | 4 | 8 | 9 (8) | 12 (11) |
| Mean % Tumor Cells* | 0.05 | 61.12 | 0.59 | (44.68) 50.57 | (2.80) 10.32 |
| Std. Deviation | 0.08 | 26.78 | 0.76 | (30.99) 33.95 | (4.76) 26.46 |
| Std. Error | 0.03 | 13.39 | 0.27 | (10.96) 11.32 | (1.44) 7.64 |
| Statistical Significance (versus Vehicle control)*** | — | — | p = 0.02 | — | (p = 0.007) p = 0.01 |

Numbers in ( ) reflect values adjusted to exclude two suspected contaminated PB samples (n = 1 in each group). These samples were noted to have milky white exudates while attempting blood collection by cardiocenthesis and later noted to have tumors near heart or thymus on necropsy. The two suspected values showed 98 and 93% tumor cells in vehicle and 40 mg/kg VII groups (10 million cells), respectively.
*Mean % Tumor cells are defined as # of CD33+ HLA+ events/total events; where total events = # of murine CD45+ cells + # of CD33+ HLA+ events.
**Naïve samples were stained on 3 separate days among 3 separate studies. Values are reflective of the detection limit of assay, since mice were not injected with MV4-11 tumor cells.
***Statistical significance was determined using an unpaired two-tailed Student's t test with Welch's correction to account for unequal variances in the data, even in the event that the sample size was too small for the Bartlett's test for equal variance.

These data demonstrate 96% and 59% reductions (5 and 10 million cell injected groups, respectively) in tumor burden in BM with VII treatment when compared to vehicle group and 99% and 94% reductions in tumor cell engraftment with VII treatment in the PB (5 and 10 million cell, respectively) when compared to vehicle group (Table 4).

TABLE 4

Engraftment Data Summary

| | % Reduction from Vehicle Control | |
|---|---|---|
| Group ID | Bone Marrow | Peripheral blood |
| 5 million cells, VII 40 mg/kg PO, bid daily | 96 | 99 |
| 10 million cells, VII 40 mg/kg PO, bid daily | 59 | 80 (94) |

Numbers in ( ) reflect values adjusted to exclude suspected contaminated samples (n=1 in each 10 million cell PB group). These samples were noted to have milky white exudates while attempting blood collection by cardiocenthesis and subsequently noted to have tumors near heart or thymus on necropsy. The two suspected values showed 98 and 93% tumor cells in vehicle and 40 mg/kg VII groups (10 million cells), respectively.

Pharmacokinetics of Compound VII in NOD-SCID Mice: Initial PK data in NOD-SCID mice was generated in an intial study prior to dosing in this study. Results indicate that dose-proportional increases in plasma levels of VI with 20, 40 or 80 mg/kg doses and exposures were limited to 2-4 hours post dose with plasma levels of VI virtually undetectable by 6 hours post-dose in all female mice. Males showed higher exposures with equivalent doses and longer duration of VI levels in the plasma when compared to females.

Due to precipitates observed in on-study formulations prepared in the initial study and other studies, additional PK data was obtained using remaining dosing solutions after study termination. NOD-SCID female mice (n=4) were dosed with 40 mg/kg dose solution of VII and plasma obtained at 1 hour post dose. As shown in Table 5, PK data using remaining formulations was moderately variable between the four animals with percent Coefficient of Variation (% CV) value of 25%. Plasma VI concentrations obtained for 1 hour exposures were similar to the values obtained in a previous PK study, indicating that these formulations were comparable.

Table 5A and 5B: PO administration of VII Calcium Salt: Mean Concentration of Compound VI in Plasma (ng/mL).

TABLE 5A

| | Dose (mg/kg) | | | | |
|---|---|---|---|---|---|
| | 20 | 40 | 80 | 20 | 40 |
| | | | Group | | |
| Time (hrs) | 1 Female | 2 Female | 3 Female | 4 Male | 5 Male |
| 0.25 | 3717 | 5140 | 3847 | 1872 | 3587 |
| 0.5 | 2240 | 3597 | 7433 | 3377 | 2860 |
| 1 | 1737 | 5497 | 7267 | 3280 | 5250 |
| 2 | 1438 | 2823 | 8193 | 2130 | 6370 |
| 4 | 55.0 | 201 | 2529 | 1209 | 1730 |
| 6 | 13.0 | 105 | 465 | 454 | 1909 |

TABLE 5B

| | Dose (mg/kg) | | | | |
|---|---|---|---|---|---|
| | 20 | 40 | 80 | 20 | 40 |
| | | | Group | | |
| | 1 Female | 2 Female | 3 Female | 4 Male | 5 Male |
| | | | Dose, mg/kg | | |
| Parameter | 20 | 40 | 80 | 20 | 40 |
| $C_{max}$ | 3717 | 5497 | 8193 | 3377 | 6370 |
| $T_{max}$ | 0.25 | 1.00 | 2.00 | 0.50 | 2.00 |
| $AUC_{last}$, ng * hr/mL | 5351 | 11498 | 27013 | 10261 | 20831 |
| $AUC_{inf}$, ng * hr/mL | 5362 | 11625 | 27662 | 11434 | 27170 |
| $T_{1/2}$, hrs | 0.59 | 0.84 | 0.97 | 1.79 | 2.30 |

TABLE 6

PK Data in NOD-SCID Mice Using Remaining Dosing Solutions.
N = 3 animals per group

| | Dose 40 mg/kg VII |
|---|---|
| Average Conc. (ng/mL VI) | 4210 |
| Standard Deviation | 1035 |
| Coefficient of Variation (%) | 25 |

7.3.3 Conclusions

Intravenous administration of MV4-11 tumor cells at 10 million cells per mouse resulted in greater dissemination of tumors to multiple anatomical sites in comparison to 5 million cells. Moreover, mice inoculated with 10 million cells more consistently had high levels of engraftment in the bone marrow and peripheral blood. Administration of 40 mg/kg VII to mice bearing disseminated MV4-11 tumors demonstrated marked efficacy when compared to vehicle treated mice with respect to overall survival and disease-related sequelae regardless of cell titer. Additionally, VII was well tolerated by NOD-SCID mice for greater than 60 days in this study and formulations used appeared adequate to achieve similar systemic exposures as in previous PK study.

In summary, VII treated mice reproducibly demonstrated a drug-related reduction in the number of total tumors identified, the total number of tumored animals, and in disease severity as measured by body weight loss, condition at necropsy, and other in-life clinical observations. Data from this study was similar to a previous efficacy study, showing repeated prolongation of survival of MV4-11 bearing mice with VII treatment. Additionally, mice treated with VII demonstrated fewer detectable MV4-11 tumor cells in the bone marrow and peripheral blood when compared to vehicle controls. These data suggest that Syk/Flt-3 kinase inhibitors may be a valuable therapeutic for the treatment of leukemia patients bearing FLT-3-ITD or other leukemias associated with Flt-3 mutations.

7.4 Example 4

Inhibition of Constitutive Flt-3 Activity in Lysates from MV4-11 Tumor Grafts

Initial studies had shown that treatment of MV4-11 human AML cells resulted in the inhibition of constitutive phosphorylation of Flt-3. Given these data, the phosphorylation of Flt-3 versus total Flt-3 was assessed ex vivo in tumor cell lysates from randomly selected mice from this study using immunoprecipitation (IP) of human Flt-3 and subsequent. Western blot analysis of phosphorylated Flt-3 was carried out as follows.

7.4.1 Experimental Protocol

Preparing Tumor Lysates.
1. Harvest the tumor as soon as possible.
2. Pulverize frozen tumor in liquid nitrogen.
3. Weigh and normalize in 250 mg/1 ml ice-cold RIPA buffer (Santa Cruz Biotechnology, sc-24948) containing protease inhibitor and phosphotase inhibitor cocktail(Sigma, P5726, 1 ml/100 ml lysis buffer).
4. Homogenize on ice.

Microcentrifuge and collect the clear supernatant which is the tumor lysate.

BCA Assay to measure the protein concentration.
BCA assay kit was obtained from Pierce Prod#23227)
1. Preparation of BSA standard.: 2000 ug/ml→1500 ug/ml→1000 ug/ml→750 ug/ml→500 ug/ml→250ug/ml→125 ug/ml→25 ug/ml
2. Pre-dilute test sample with cold PBS (tumor lysate 1:20 dilution)
3. 200 ul BCA working solution+25 ul standard/sample, incubate at 37° C. for 30 min.
4. Cool plate and read OD 570 nm.

Immunoprecipitation.
1. Take 1 mg tumor lysate and add primary antibody 2 ug (Anti-Flt-3 S-18, Santa Cruz, #sc-480) adjust volume to 500 ul with lysis buffer. Incubate with gentle rocking for 1 h at 4° C.
2. Add protein A/G plus-agarose beads (Santa Cruz, SC-2003) 40 ul. Incubate with gentle rocking for 1 h at RT.
3. Microcentrifuge for 30 second at 4° C. Wash pellet three times with 500 ul of 1× lysis buffer. Keep on ice during washes.
4. Resuspend the pellet with 30 ul 2× Tris-Glysine SDS loading buffer +5 ul reducing agent 10× (Invitrogen).
5. Heat the sample to 95-100° C. for 5 minutes.
6. Store the sample at −80° C.

Western Blot Procedure.
1. Load 20 ul of the sample on 8% Tris-Glysine gel.
2. Run in 1× Tris-glysine SDS running buffer.
3. Transfer to PVDF membrane in 1× Tris-Glysine transfer buffer.

4. Block in 1% BSA/TBST (TBS+0.1% Tween-20) at RT for 1 h.
5. Add primary antibody 1:5000 overnight at 4° C. Anti-Phosphotyrosine clone 4G10 (mouse monoclonal, Upstate, #05-321). Anti-Phospho-Flt-3 (Tyr591) (mouse mAb, Cell Signaling, #3466S)
6. Wash 2 h in TBST.
7. 2° Ab anti-mouse IgG-HRP (Amersham, NA931V) 1:5000 in 5% milk/TBST (Blotting grade Blocker, non-fat dry milk, Bio-Rad, #170-6404) for 1 h. ECL-plus (Amersham, RPN2132) short exposure.

Stripping and Reprobing Membranes.
1. Submerge the membrane in stripping buffer (Pierce, #21062) and incubate 37° C. for 1 h.
2. Wash the membrane in TBST for 15 mins, twice.
3. Block the membrane with 1% BSA/TBST for 1 h.
4. Add anti-Flt-3 1:5000 (Santa Cruz, #sc-480) in 5% milk/TBST, incubate overnight at 4° C.
5. Wash 2 h in TBST.
6. 2° Ab anti-rabbit IgG-HRP (Amersham, NA934V) 1:5000 in 5% milk/TBST at RT for 1 h.
7. ECL-plus short exposure.

In addition, the blot was reprobed for total Flt-3 levels. Constitutive phosphorylation of Flt-3 was reduced in tumors from 40 mg/kg VII treated animals in a dose-dependent manner when compared to vehicle treated controls.

7.4.2 Phosphorylated Histone H3 Analysis of MV4-11 Tumor Xenografts

Proliferation was assessed ex vivo in formalin fixed tumor sections from three randomly selected mice from this study using immunohistochemical staining of human-specific phosphorylated histone H3 (phH3) as a marker for tumor cell proliferation. Human phH3 expression was reduced in tumor sections in a dose-dependent manner following treatment with VII. When compared to MV4-11 tumor xenografts from vehicle treated mice, treatment with 20 and 40 mg/kg VII resulted in a 53% and 71% inhibiton of phH3 staining, respectively. These data indicate that VII inhibition reduced the proliferative capacity of MV4-11 tumors in vivo, correlating with the reduced tumor volumes observed during the in-life portion of the study. The reduced proliferation is likely to be due to reduced constitutive Flt-3 phosphorylation, as this activity has been shown to be required for survival of MV4-11 cells in vitro.

7.4.3 Inhibition of Downstream Signaling Events

Figure 11:
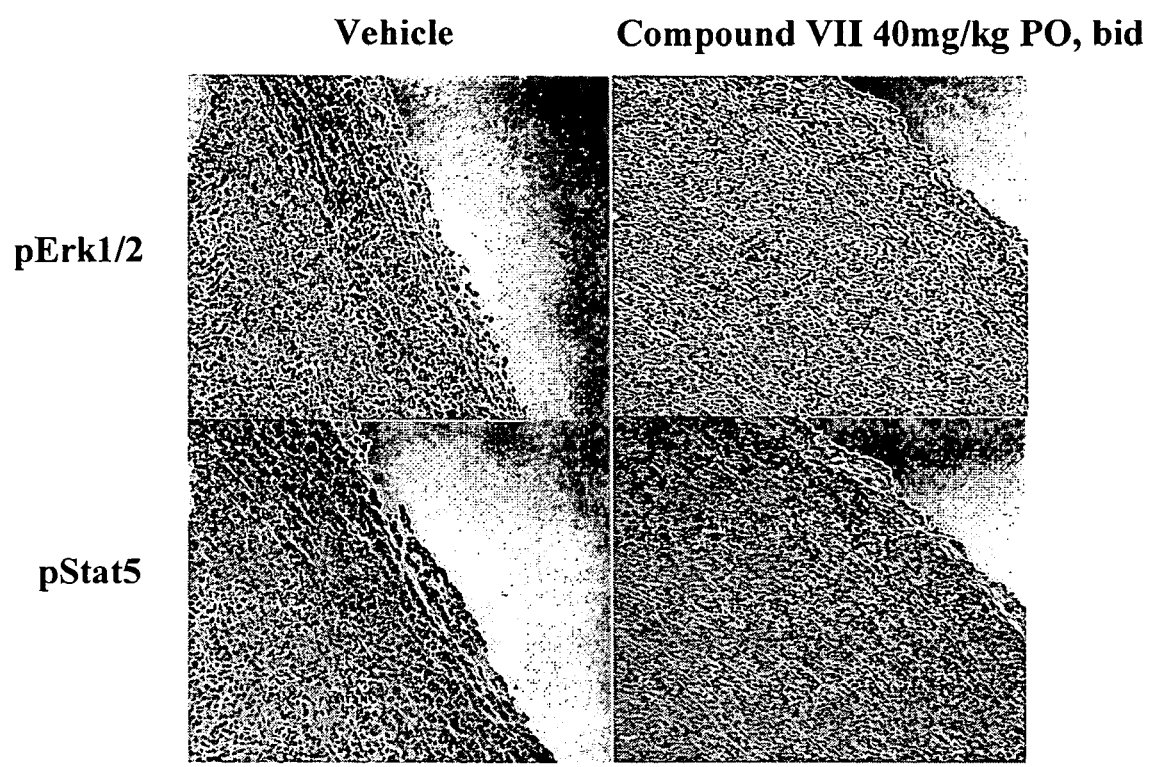
FIG. 11 shows a representative data illustrating immunohistochemical staining for pErk1/2 and pStat5 in tumor sections from MV4-11 tumor bearing mice treated orally twice per day for 26 days. Tumors were harvested from mice ~2 hours following final dose of vehicle or 40 mg/kg VII.
Figure 12:
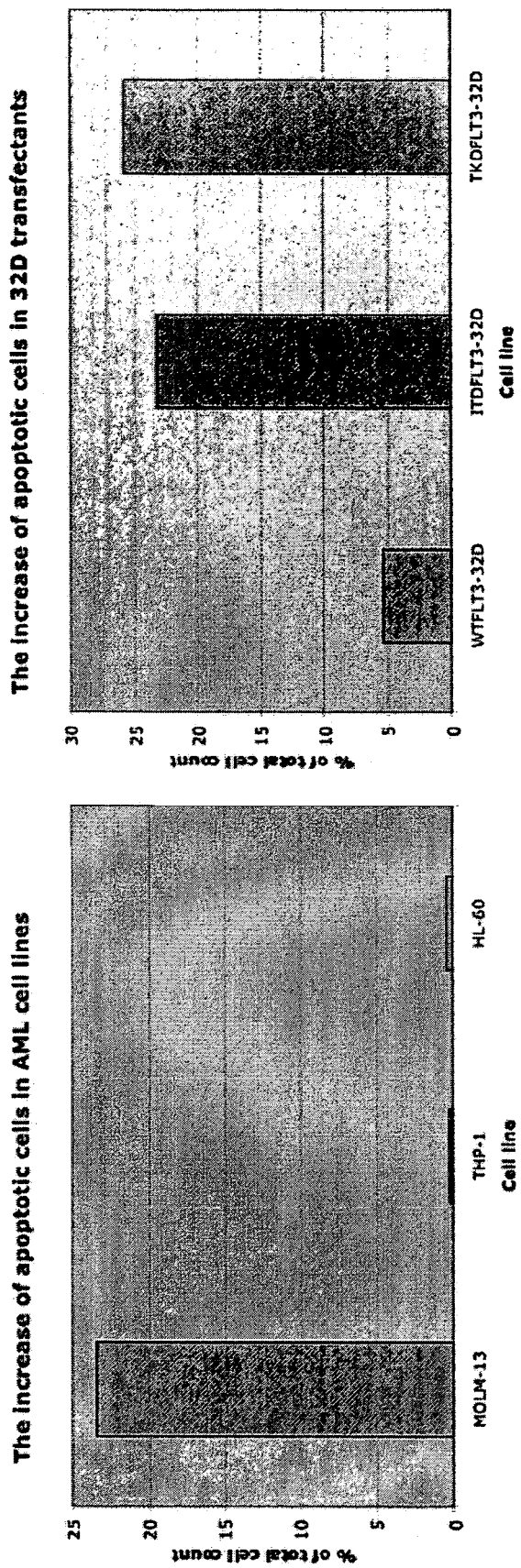
FIG. 12 shows the effect of treating AML cells or 32D transfectants with 1 uM VI in inducing apoptosis as determined by Annexin V and PI staining.

Additional immunohistochemical staining of tumor sections from mice treated for 26 days with 40 mg/kg VII demonstrated reduced STAT5 and ERK1/2 phosphorylation, which are downstream molecules in the Flt-3:ITD signaling pathway in MV4-11 cells (FIG. 11).

7.5 Example 5

Examinination of Compound VI on Acute Myelegeous Leukemic Cells and Comparision to Kinase Inhibitor AG1296

AML cells or 32D transfectants were treated for 48 h (AML) or 24 h (32D) with 1 uM VI, and the increase in % of apoptotic cells was determined using Annexin V and PI staining. The data show that AML cells harboring Flt-3 ITD are uniquely sensitive to VI-induced apoptosis. Similarly, 32D transfected with ITD or point mutated Flt-3 TDK undergo more apoptosis at 24 h than 32D cells transfected with wt Flt-3.

7.6 Example 6

Synthesis of Prodrug Compound 4

7.6.1. N4-(2,2-dimethyl-4-[(di-tert-butyl phosphonoxy)methyl]-3-oxo-5-pyrido[1,4]oxazin-6-yl)-5-fluoro-N2-(3,4,5-trimethoxyphenyl)-2,4-pyrimidinediamine (Compound 3)

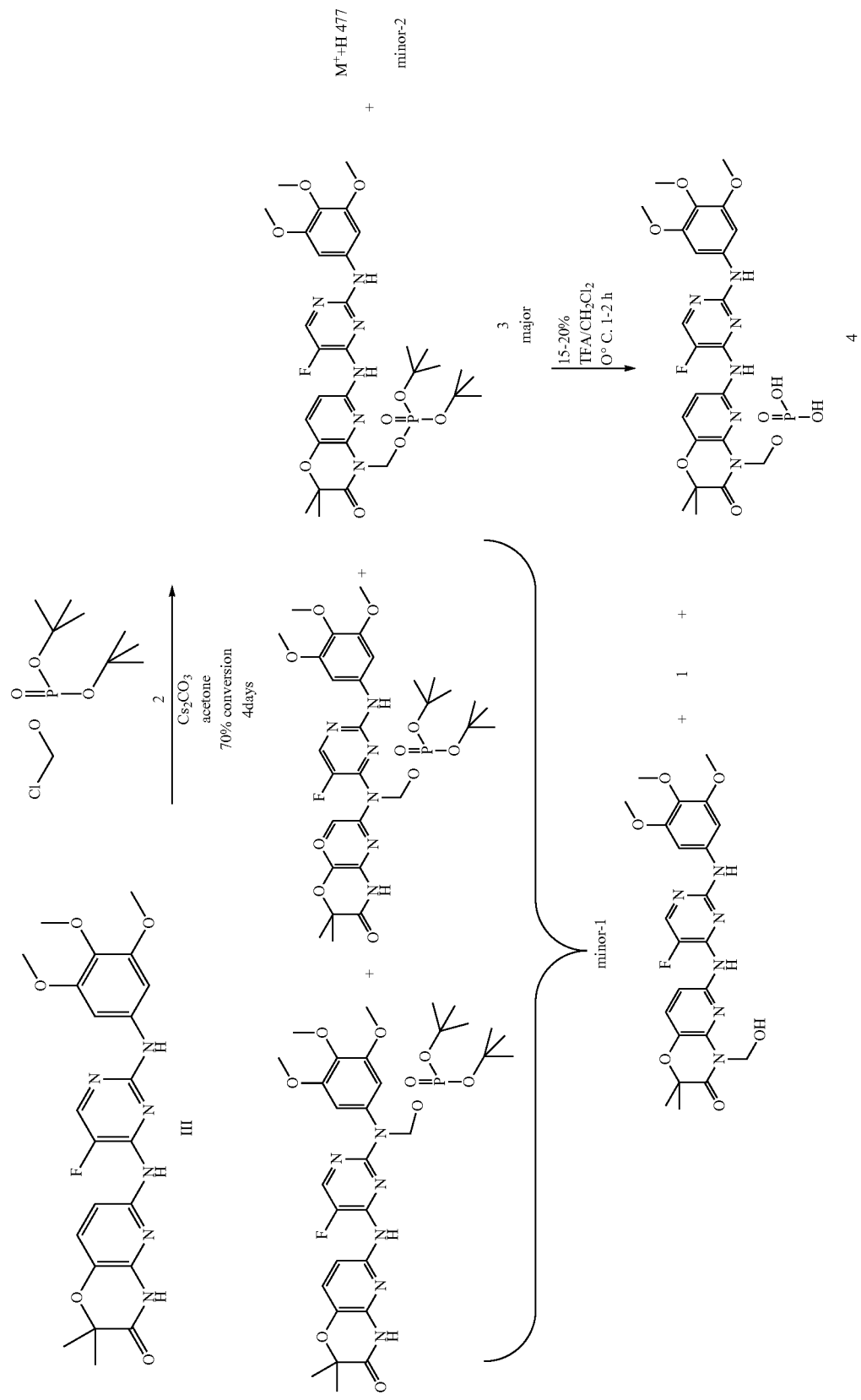

N4-(2,2-dimethyl-3-oxo-4H-5-pyrido[1,4]oxazin-6-yl)-5-fluoro-N2-(3,4,5-trimethoxyphenyl)-2,4-pyrimidinediamine (Compound III, 1.0 g, 2.12 mmol), $Cs_2CO_3$ (1.0 g, 3.07 mmol) and di-tert-butyl chloromethyl phosphate (2, 0.67 g, 2.59 mmol) in acetone (20 mL) was stirred at room temperature under nitrogen atmosphere. Progress of the reaction was monitored by LC/MS. Crude reaction mixture displayed three product peaks with close retention times with $M^++H$ 693 (minor-1), 693 (major; 3) and 477 (minor-2) besides starting material (Compound III). Upon stirring the contents for 4 days (70% consumption), the reaction mixture was concentrated and diluted with water. The resultant pale yellow precipitate formed was collected by filtration and dried. The crude solid was purified by silica gel (pretreated with 10% $NEt_3/CH_2Cl_2$ followed by eluting with hexanes) column chromatography by gradient elution with 70% EtOAc/hexanes-100% EtOAc). The fractions containing Compound III and $M^++H$ 693 were collected and concentrated. The resulting crude white solid was subjected to repurification in the similar manner as described previously but by eluting with 30%-50%-75%-100% EtOAc/hexanes. The major product peak with $M^++H$ 693 was collected as a white solid (270 mg, 18%) and was characterized as N4-(2,2-dimethyl-4-[(di-tert-butyl phosphonoxy)methyl]-3-oxo-5-pyrido[1,4]oxazin-6-yl)-5-fluoro-N2-(3,4,5-trimethoxyphenyl)-2,4-pyrimidinediamine (Compound 3). $^1H$ NMR (DMSO-d6): δ 9.21 (s, 1H), 9.17 (s, 1H), 8.16 (d, 1H, J=2.6 Hz), 7.76 (d, 1H, J=8.5 Hz), 7.44 (d, 1H, J=8.5 Hz), 7.02 (s, 2H), 5.78 (d, 1H, $J^3_{PH}$=6.1 Hz), 3.64 (s, 6H), 3.58 (s, 3H), 1.45 (s, 6H), 1.33 (s, 9H). LCMS: ret. time: 14.70 min.; purity: 95%; MS (m/e): 693 ($MH^+$). $^{31}P$ NMR (DMSO-d6): −11.36.

7.6.2 N4-(2,2-dimethyl-4-[(dihydrogen phosphonoxy)methyl]-3-oxo-5-pyrido[1,4]oxazin-6-yl)-5-fluoro-N2-(3,4,5-trimethoxyphenyl)-2,4-pyrimidinediamine (Compound 4)

Trifluoroacetic acid (1.5 mL) was added dropwise as a neat for 5 min to N4-(2,2-dimethyl-4-[(di-tert-butyl phosphonoxy)methyl]-3-oxo-5-pyrido[1,4]oxazin-6-yl)-5-fluoro-N2-(3,4,5-trimethoxyphenyl)-2,4-pyrimidinediamine (Compound 3, 120 mg, 0.173 mmol) dissolved in $CH_2Cl_2$ (10 mL) at 0° C. under nitrogen atmosphere. The contents were allowed to stir for 1.5 h. Progress of the reaction mixture was monitored by LC/MS. After complete consumption of the starting material, reaction mixture was concentrated, dried and triturated with ether. The ethereal layer was decanted and dried to provide the crude solid. LC/MS analysis of the crude displayed three peaks with $M^++H$ 581, 471 and 501. The peak corresponding to $M^++H$ 581 was collected by preparative HPLC chromatographic purification. The fractions were lyophilised and dried to provide 53 mg (52%) of off white fluffy solid and characterized as N4-(2,2-dimethyl-4-[(dihydrogen phosphonoxy)methyl]-3-oxo-5-pyrido[1,4]oxazin-6-yl)-5-fluoro-N2-(3,4,5-trimethoxyphenyl)-2,4-pyrimidinediamine (Compound 4). $^1H$ NMR (DMSO-d6): δ 9.21 (br s, 2H), 8.16 (d, 1H, J=2.6 Hz), 7.93 (d, 1H, J=8.5 Hz), 7.39 (d, 1H, J=8.5 Hz), 7.05 (s, 2H), 5.79 (d, 1H, $J^3_{PH}$=6.6 Hz), 3.67 (s, 6H), 3.59 (s, 3H), 1.44 (s, 6H). LCMS: ret. time: 8.52 min.; purity: 95%; MS (m/e): 581 ($MH^+$). $^{31}P$ NMR (DMSO-d6): −2.17.

7.7 Example 7

Alternative Synthesis of Prodrug Compound 4

An alternative method of synthesizing prodrug Compound 4 which alleviates the need for column chromatography and HPLC purification is provided below.

7.7.1 Synthesis of N4-(2,2-dimethyl-4-[(di-tert-butyl phosphonoxy)methyl]-3-oxo-5-pyrido[1,4]oxazin-6-yl)-5-fluoro-N2-(3,4,5-trimethoxyphenyl)-2,4-pyrimidinediamine (Compound 3)

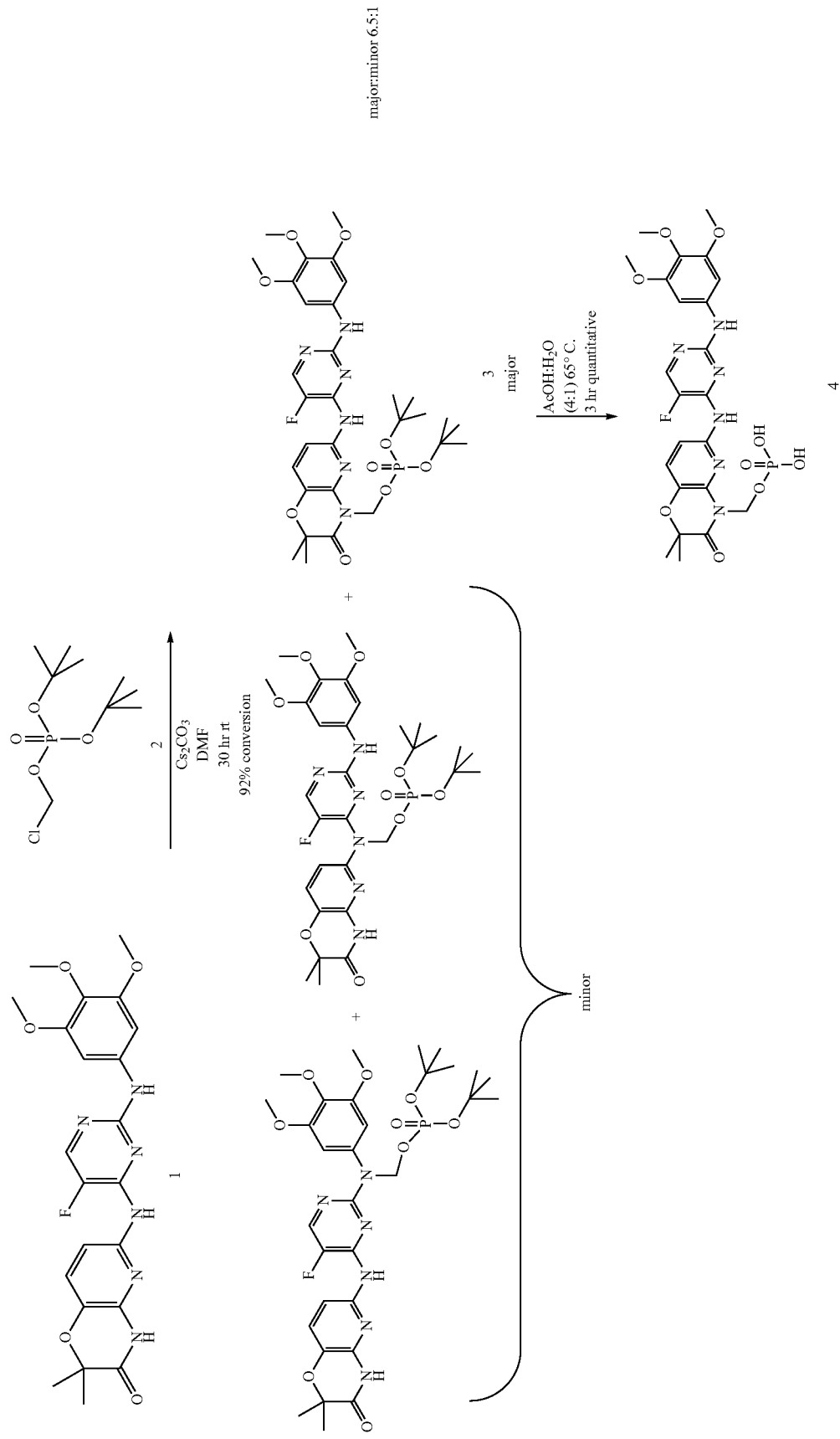

N4-(2,2-dimethyl-3-oxo-4H-5-pyrido[1,4]oxazin-6-yl)-5-fluoro-N2-(3,4,5-trimethoxyphenyl)-2,4-pyrimidinediamine (Compound III, 19.73 g, 41.97 mmol), Cs$_2$CO$_3$ (15.04 g, 46.16 mmol) and di-tert-butyl chloromethyl phosphate (13.0 g, 50.38 mmol) in DMF (100 mL) was stirred at room temperature under nitrogen atmosphere. Progress of the reaction was monitored by in process LC/MS. Crude reaction mixture displayed two product peaks (ratio 1:6.5) with close retention times displaying M$^+$+H 693 (minor) and 693 (major) besides starting material (Compound III). Initial yellow reaction mixture turned to olive green as the reaction progressed. Workup is carried out as follows:

1). Upon stirring the contents for 30 h (92% consumption), reaction mixture was poured onto ice-water (400 mL) and stirred the contents by adding brine solution (200 mL). Fine yellow tan solid formed was filtered, washed with water and dried overnight.

2). The solid (35 g) was dissolved in MTBE (500 mL) and washed with water (400 mL). Aqueous layer was extracted with MTBE (2×350 mL) till the absence of UV on TLC. Combined organic layers were dried over anhydrous Na$_2$SO$_4$ and decanted.

Note: step 2 can be done directly, however, DMF extraction back into solution leads to difficulty in the crystallization step.

3). The dark red clear solution was subjected to 10 g of activated charcoal treatment, heated to boil and filtered.

4). The dark red clear solution was concentrated by normal heating to 400 mL of its volume and left for crystallization. The solid crystallized as granules was filtered, crushed the granules to powder, washed with MTBE (400 mL) and dried under high vacuum. See step 7 for the workup of mother liquor. Weight of the solid: 17 g; purity: 90% (Compound 3), 6.26% (Compound III), 1.8% (minor M+ 693).

5). At this stage solid was taken in 500 ml of ethylether and heated to boil. Cooled and filtered to remove undissolved material. Filtrate was concentrated.

6). Above concentrate was subjected to crystallization in MTBE (300 mL). The white solid formed was filtered, washed with MTBE (100 mL) and dried under high vacuum to provide the desired N4-(2,2-dimethyl-4-[(di-tert-butyl phosphonoxy)methyl]-3-oxo-5-pyrido[1,4]oxazin-6-yl)-5-fluoro-N2-(3,4,5-trimethoxyphenyl)-2,4-pyrimidinediamine (Compound 3) in 97% purity. $^1$H NMR (DMSO-d6): δ 9.21 (s, 1H), 9.17 (s, 1H), 8.16 (d, 1H, J=2.6 Hz), 7.76 (d, 1H, J=8.5 Hz), 7.44 (d, 1H, J=8.5 Hz), 7.02 (s, 2H), 5.78 (d, 1H, J$^3_{PH}$=6.1 Hz), 3.64 (s, 6H), 3.58 (s, 3H), 1.45 (s, 6H), 1.33 (s, 9H). LCMS: ret. time: 14.70 min.; purity: 95%; MS (m/e): 693 (MH$^+$). $^{31}$P NMR (DMSO-d6): −11.36. Weight of the solid: 15.64 g (yield: 55%); purity: 97% (R935787), 3% (Compound III).

7). Mother liquor was concentrated and steps 5 and 6 were repeated to provide Compound 3.

7.7.2 Synthesis of N4-(2,2-dimethyl-4-[(dihydrogen phosphonoxy)methyl]-3-oxo-5-pyrido[1,4]oxazin-6-yl)-5-fluoro-N2-(3,4,5-trimethoxyphenyl)-2,4-pyrimidinediamine (Compound 4)

N4-(2,2-dimethyl-4-[(di-tert-butyl phosphonoxy)methyl]-3-oxo-5-pyrido[1,4]oxazin-6-yl)-5-fluoro-N2-(3,4,5-trimethoxyphenyl)-2,4-pyrimidinediamine (Compound 3); (15.0 g, 21.67 mmol) dissolved in AcOH:H$_2$O (225 mL, 4:1) was heated at 65° C. (oil bath temp). The progress of the reaction was monitored by in process LC/MS. The reaction mixture transformed to faint tan white solid after 1h of heating. At this point most of Compound 3 converted to mono des t-butyl product. After 3 h of heating, consumption of SM and complete conversion of intermediate (mono des t-butylated) to product was observed.

Reaction mixture was cooled, poured onto ice-water (200 mL), stirred for 20 min and filtered. The clear white filter cake was washed with water (600 ml) and acetone (200 mL) successively, dried for 2 h followed by drying under high vacuum over P$_2$O$_5$ in a desiccator. Weight of the solid: 12.70 g; purity: 97% (Compound 3) and 3% (Compound III) $^1$H NMR indicated acetic acid presence (1:1)

To remove acetic acid, the solid was taken in acetonitrile (300 mL) and concentrated by rotovap vacuum. This process was repeated 2 times with acetonitrile and toluene (3×300 mL). The solid obtained was dried under high vacuum at 50° C.

Finally, the solid was taken in acetone (400 mL), filtered and dried to provide N4-(2,2-dimethyl-4-[(dihydrogen phosphonoxy)methyl]-3-oxo-5-pyrido[1,4]oxazin-6-yl)-5-fluoro-N2-(3,4,5-trimethoxyphenyl)-2,4-pyrimidinediamine (Compound 4). $^1$H NMR (DMSO-d6): δ 9.21 (br s, 2H), 8.16 (d, 1H, J=2.6 Hz), 7.93 (d, 1H, J=8.5 Hz), 7.39 (d, 1H, J=8.5 Hz), 7.05 (s, 2H), 5.79 (d, 1H, J$^3_{PH}$=6.6 Hz), 3.67 (s, 6H), 3.59 (s, 3H), 1.44 (s, 6H). LCMS: ret. time: 8.52 min.; purity: 95%; MS (m/e): 581 (MH$^+$). $^{31}$P NMR (DMSO-d6): −2.17.

7.8 Example 8

Synthesis of N4-(2,2-dimethyl-4-[(dihydrogen phosphonoxy)methyl]-3-oxo-5-pyrido[1,4]oxazin-6-yl)-5-fluoro-N2-(3,4,5-trimethoxyphenyl)-2,4-pyrimidinediamine mono calcium salt (Compound 6)

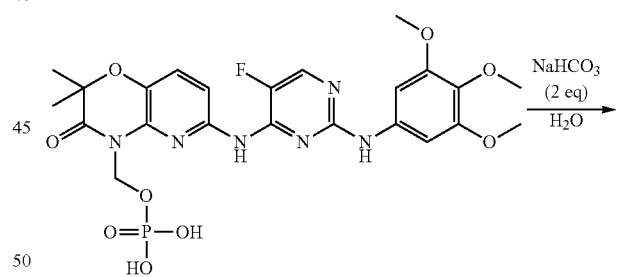

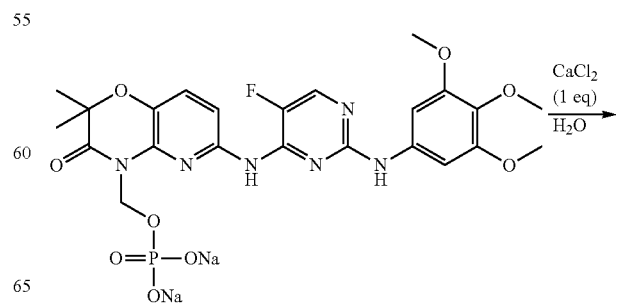

-continued

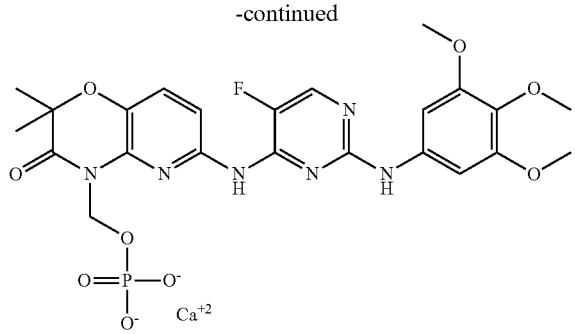

Aqueous (10 mL) NaHCO$_3$ (0.17 g, 2.02 mmol) solution was added dropwise to a suspension of N4-(2,2-dimethyl-4-[(dihydrogen phosphonoxy)methyl]-3-oxo-5-pyrido[1,4]oxazin-6-yl)-5-fluoro-N2-(3,4,5-trimethoxyphenyl)-2,4-pyrimidinediamine (0.5 g, 0.86 mmol) in water (5 mL) at room temperature while stirring the contents. The clear solution formed was treated with aqueous (10 mL) CaCl$_2$ (0.11 g in 10 mL water, 0.99 mmol) in a dropwise manner at room temperature. The addition resulted in the precipitation of a white solid from reaction mixture. Upon completion of addition, the contents were stirred for a period of 30 min, filtered, washed with water (40 mL) and dried. The clear white solid was taken in water (30 mL) and heated on a stir plate to boil. The solution was cooled, filtered and dried. The white solid collected and further dried under high vacuo at 80° C. for 32 h to provide 0.41 g (83%) of N4-(2,2-dimethyl-4-[(dihydrogen phosphonoxy)methyl]-3-oxo-5-pyrido[1,4]oxazin-6-yl)-5-fluoro-N2-(3,4,5-trimethoxyphenyl)-2,4-pyrimidinediamine mono calcium salt (Compound 6).

7.9 Example 9

Synthesis of Prodrug Compound 8

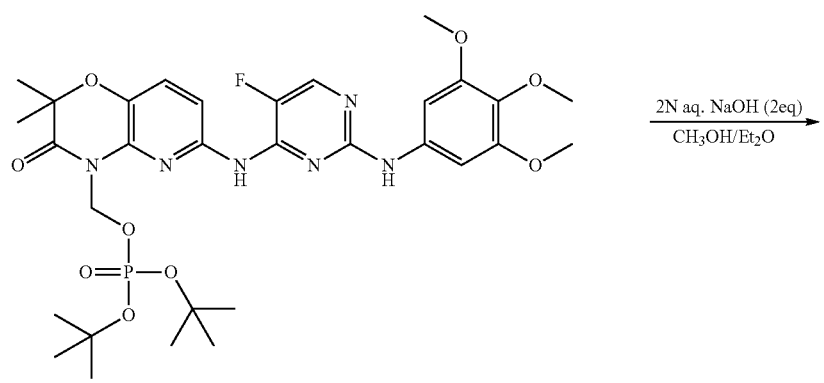

N4-(2,2-dimethyl-4-[(di-tert-butyl phosphonoxy)methyl]-3-oxo-5-pyrido[1,4]oxazin-6-yl)-5-fluoro-N2-(3,4,5-trimethoxyphenyl)-2,4-pyrimidinediamine (prepared as described above) (0.2 g, 0.29 mmol) was added to a mixture of MeOH(5 mL) and Et$_2$O (5 mL). 2N aq. NaOH (0.023 g, 0.58 mmol) was added at once while stirring the contents at room temperature. Progress of the reaction was monitored by LC/MS. After 8 h of stirring, the solid precipitated was filtered and dried to provide N4-(2,2-dimethyl-4-methoxymethyl-3-oxo-5-pyrido[1,4]oxazin-6-yl)-5-fluoro-N2-(3,4,5-trimethoxyphenyl)-2,4-pyrimidinediamine (Compound 8) as a white solid (0.11 g, 74%). $^1$H NMR (DMSO-d6): δ 9.47 (s, 1H), 9.15 (s, 1H), 8.16 (d, 1H, J=3.8 Hz), 7.87 (d, 1H, J=8.5 Hz), 7.37 (d, 1H, J=8.5 Hz), 7.03 (s, 2H), 5.40 (s, 2H), 3.66 (s, 6H), 3.59 (s, 3H), 3.27 (s, 3H), 1.44 (s, 6H). LCMS: ret. time: 12.88 min.; purity: 92%; MS (m/e): 515 (MH$^+$).

7.10 Example 10

The Active 2,4-Pyrimidinediamine Compounds are Tolerated in Animals

The ability of numerous biologically active 2,4-pyrimidinediamine compounds to exert their activity at doses below those exhibiting toxicity in animals has been demonstrated previously (see, e.g., U.S. application Ser. No. 10/355,543 filed Jan. 31, 2003 (US2004/0029902A1), international application Serial No. PCT/US03/03022 filed Jan. 31, 2003 (WO 03/063794), U.S. application Ser. No. 10/631,029 filed Jul. 29, 2003 (US2007/0060603), international application Serial No. PCT/US03/24087 (WO2004/014382), U.S. application Ser. No. 10/903,263 filed Jul. 30, 2004 (U52005/0234049), and international application Serial No. PCT/US2004/24716 (WO2005/016893).

The safety pharmacology of active Compound III has been studied in a core battery of studies (respiratory, CNS, cardiovascular, and HERG). A slight reduction in heart rate and increase in RR interval was noted at 50 mg/kg in the cardio-

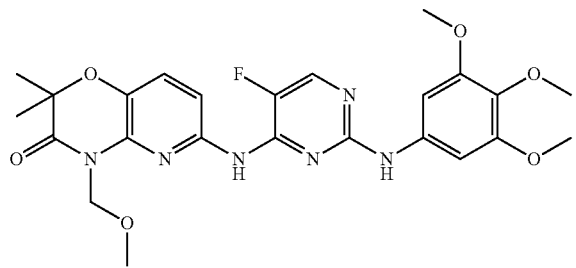

vascular study and a slight effect on a few behavioral parameters at 50 mg/kg was also noted in the CNS (Irwin) study. Otherwise the safety pharmacology studies determined that Compound III was well tolerated. GLP toxicology studies included negative mutagenicity and clastogenicity studies (Ames, chromosomal aberration, and mouse micronucleus). In 28-day toxicity studies in rats and monkeys, higher doses had evidence of a reversible effect on hematology, liver transaminase (mild effect in the rat only), spleen and thymus size (rat only) and bone marrow cellularity (rat and monkey). Immunophenotyping in the rat study revealed a significant decrease in the percentage of CD3+ cells in high dose rats while a significant increase in CD45RA+ cells was noted following recovery. Histopathology was noteworthy only for mild reductions in marrow cellularity at high doses. There was no evidence for untoward effects on humoral immunity in the anti-KLH antibody assessment. The No Observed Adverse Effect Level (NOAEL) is 10-30 mg/kg/day for rats and 100 mg/kg/day for monkeys.

Prodrug Compound 4 was tested for oral bioavailability. For the study, the prodrug was dissolved in various vehicles (e.g. PEG 400 solution and CMC suspension) for intravenous and oral dosing in the rats. Where indicated, the active metabolite Compound III compound (drug) was formulated and administered in the same vehicles. Following administration of the prodrug and/or drug, plasma samples were obtained and extracted. The plasma concentrations of the prodrug and/or drug were determined by high performance liquid chromatography/tandem mass spectrometry (LC/MS/MS) methods. Pharmacokinetic analyses were performed based on the plasma concentration data. The pharmacokinetic parameters of interest include Clearance (CL), Volume of distribution at steady-state (Vss), terminal half-life (t ½), and oral bioavailability (% F).

The results of these various pharmacokinetic experiments are illustrated in FIGS. 16-23.

Referring to FIG. 16, PK profiles are shown for IV and PO administration in Sprague-Dawley rats. For IV administration, Compound 4 was dissolved in PEG-400 and administered at a dose of 1 mg/kg. Rapid disappearance of prodrug Compound 4 was observed and drug Compound III was found in plasma samples obtained from the jugular vein. Given orally in the same vehicle, no prodrug Compound 4 was present systemically, but high levels of drug metabolite Compound III were observed.

Figure 4:
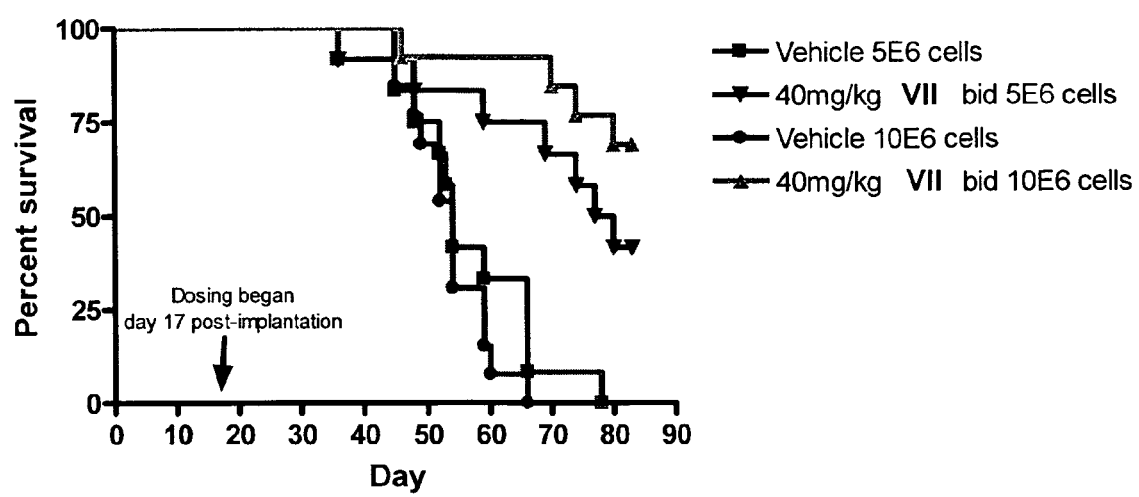
Figure 5:
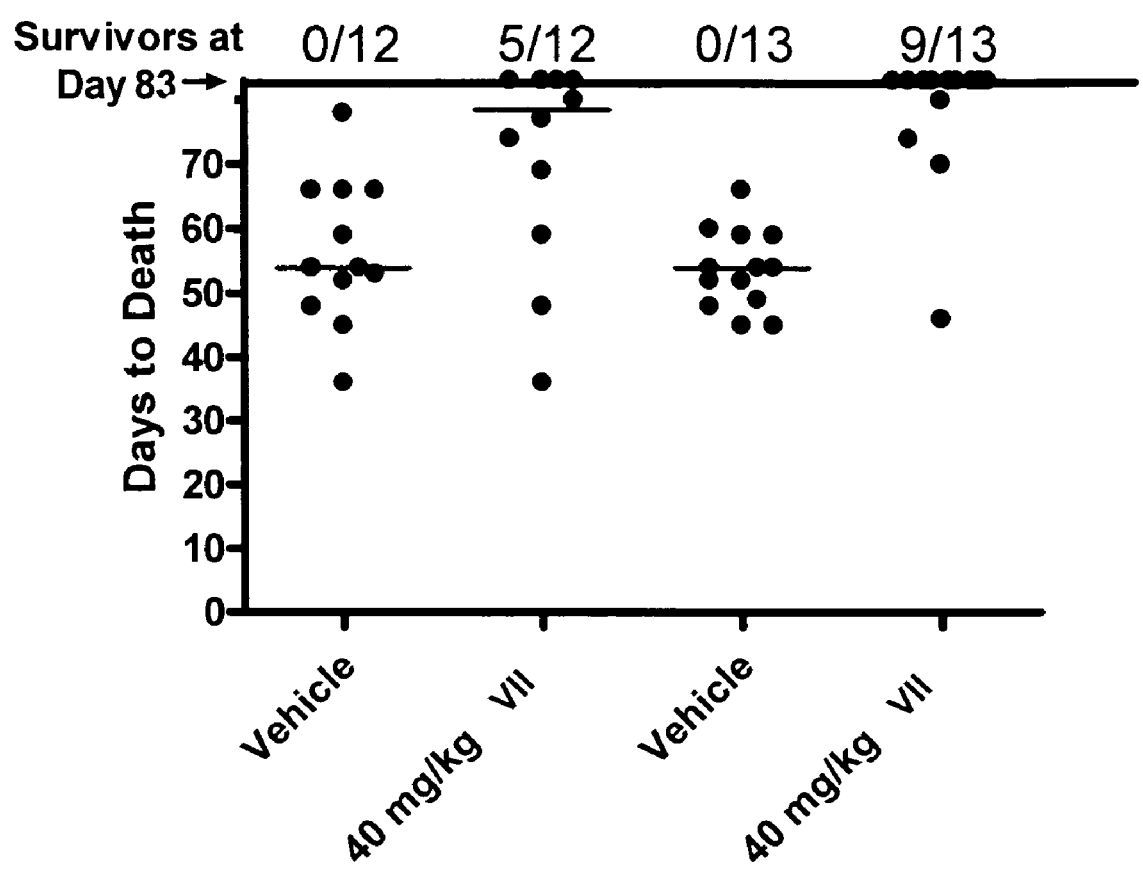
Figure 6A:
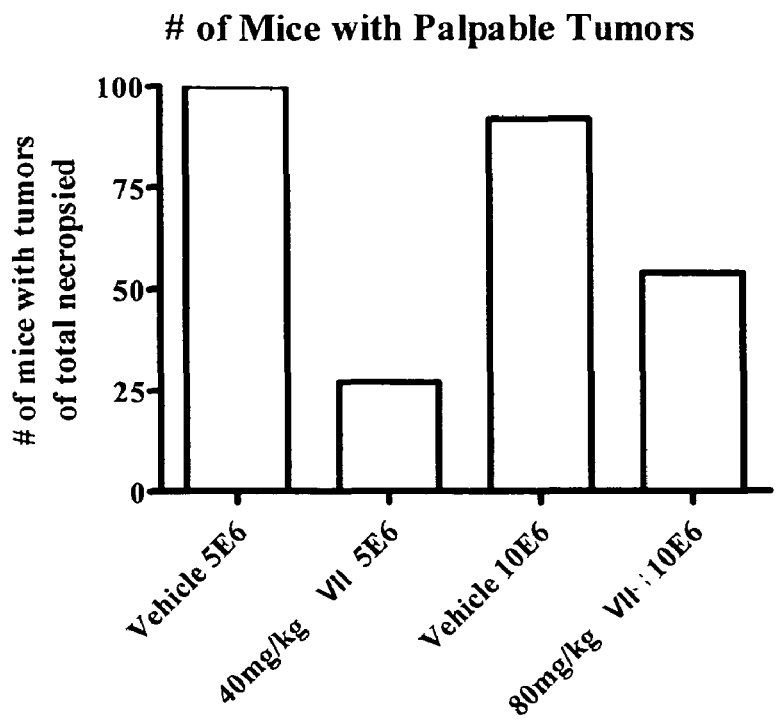
Figure 6B:
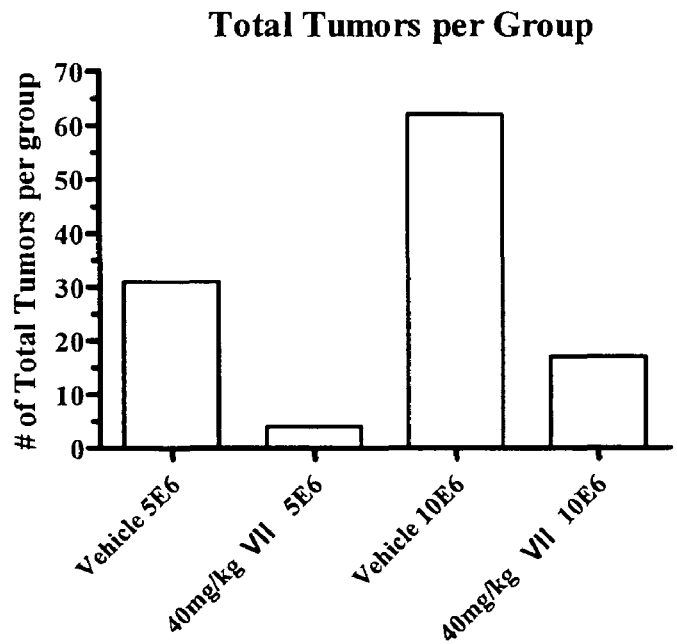
Figure 7:
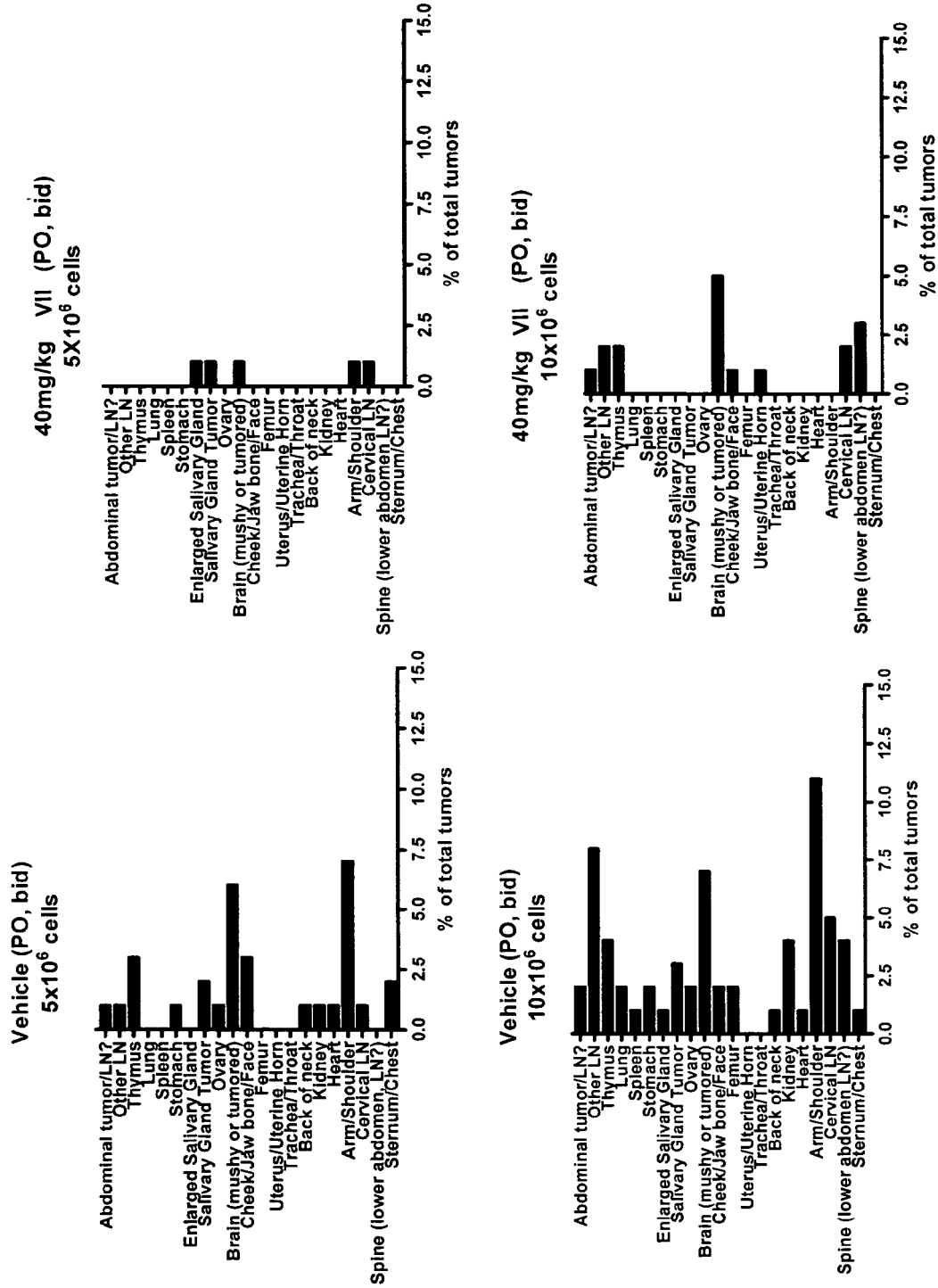
Figure 8:
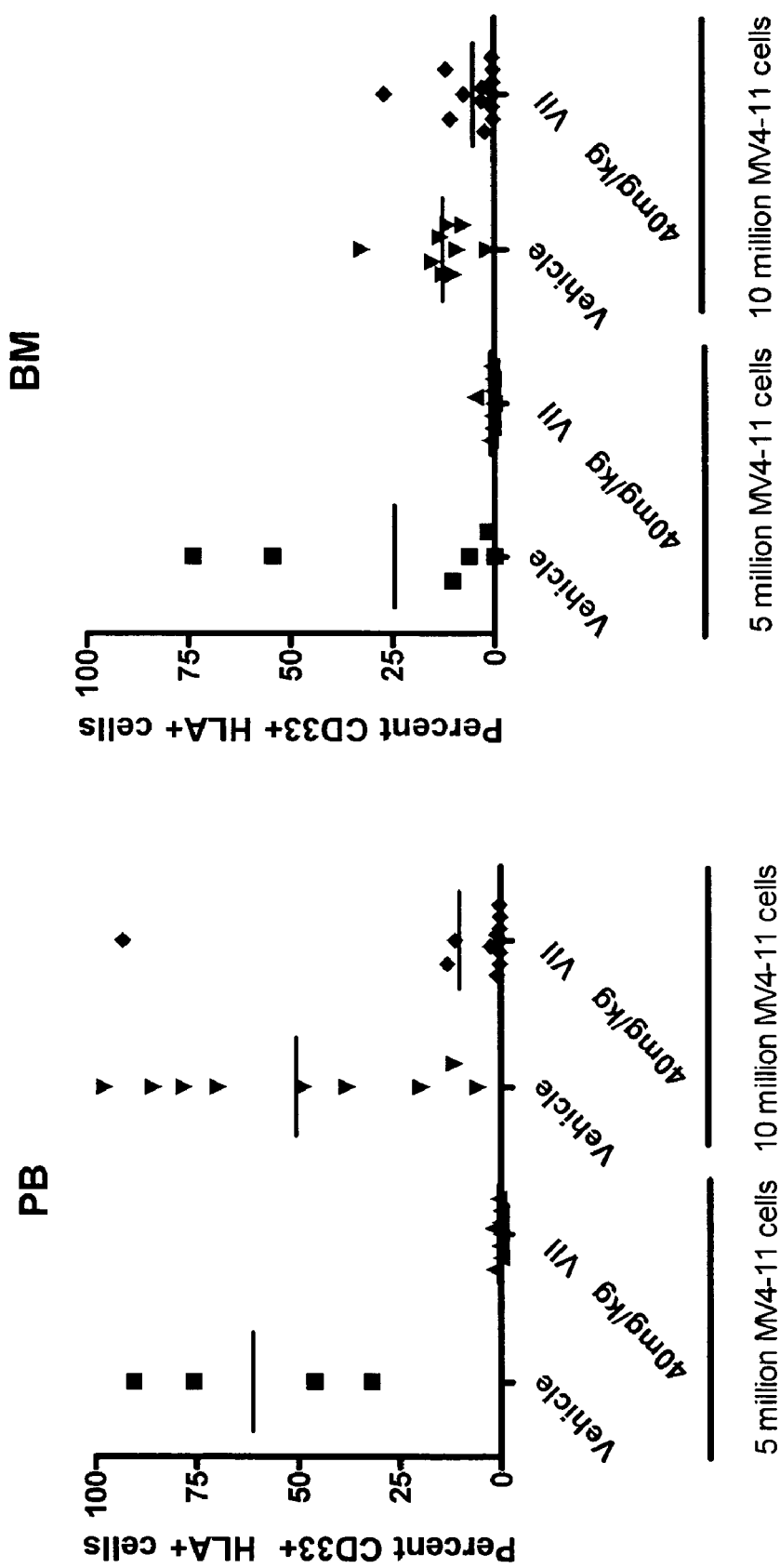
Figure 9:
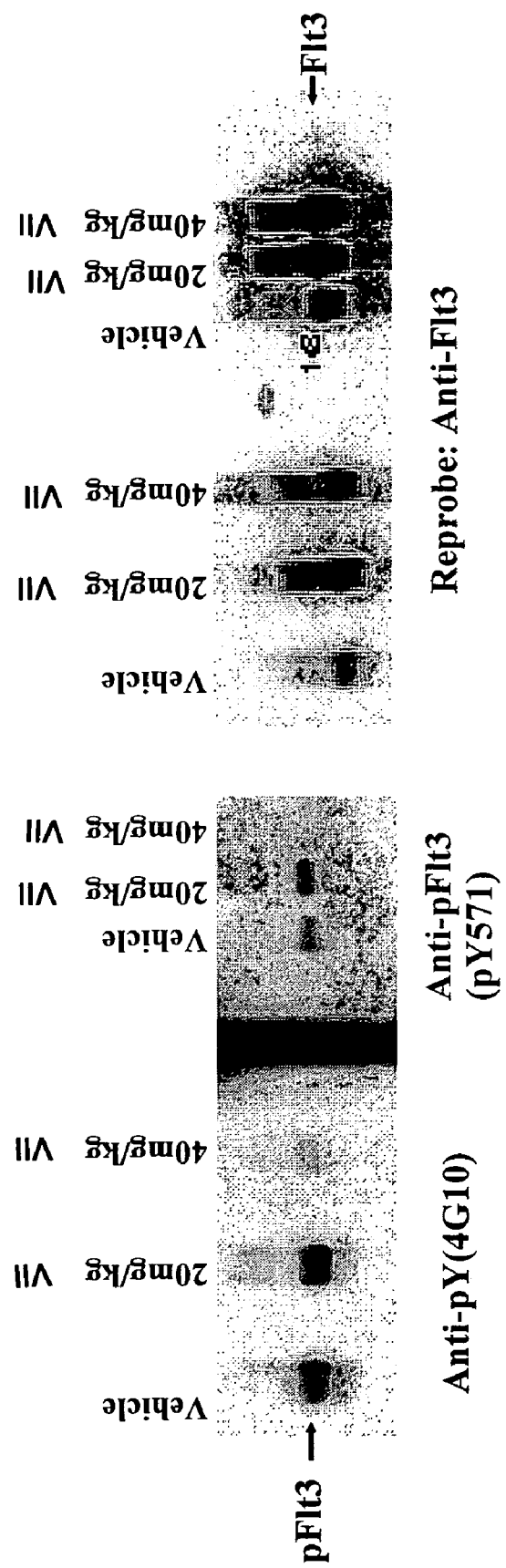
Figure 10:
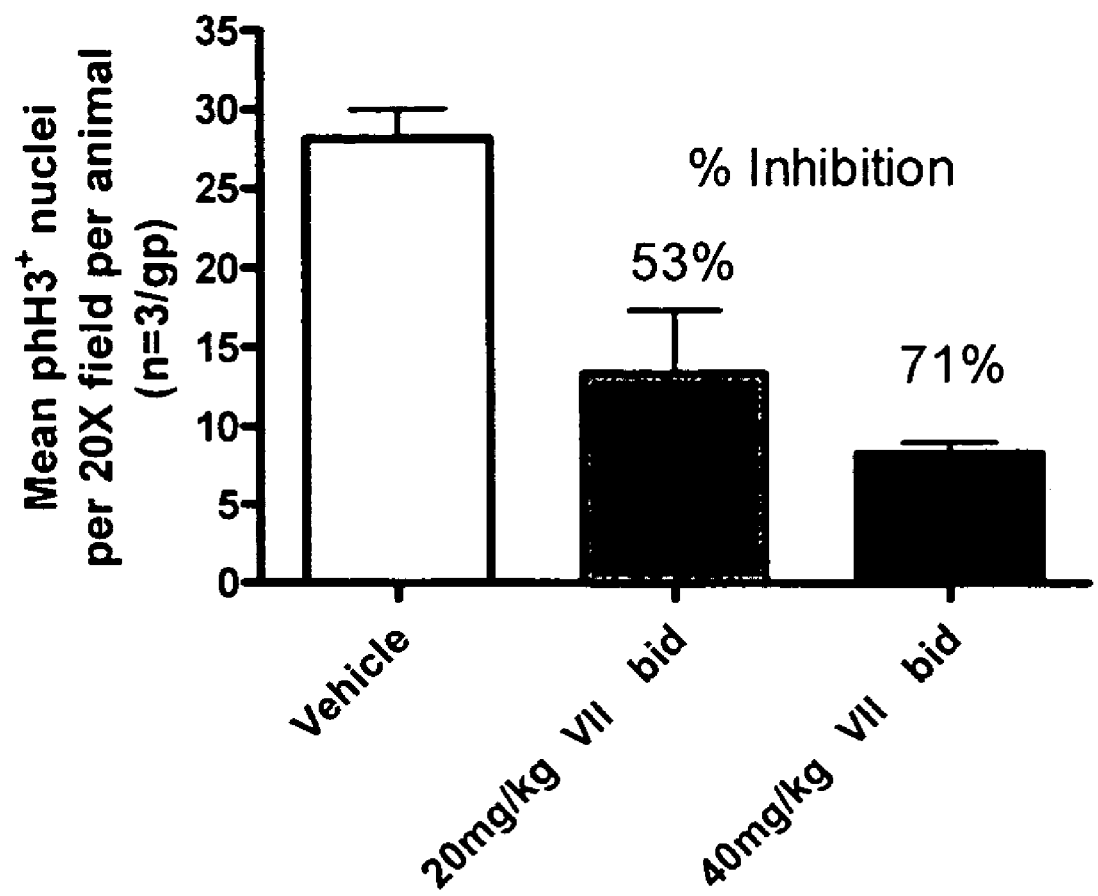

FIG. 17 summarizes the PK parameters for the study described in FIG. 4. Prodrug Compound 4 is rapidly cleared and, in part, converted to drug Compound III. Given orally at a dose of 4 mg/kg, bioavailability was determined to be 29.9%. This bioavailability number is based on data obtained from a previous study (data not shown) in which drug Compound III was administered as an IV bolus dose at 1 mg/kg.

Figure 18:
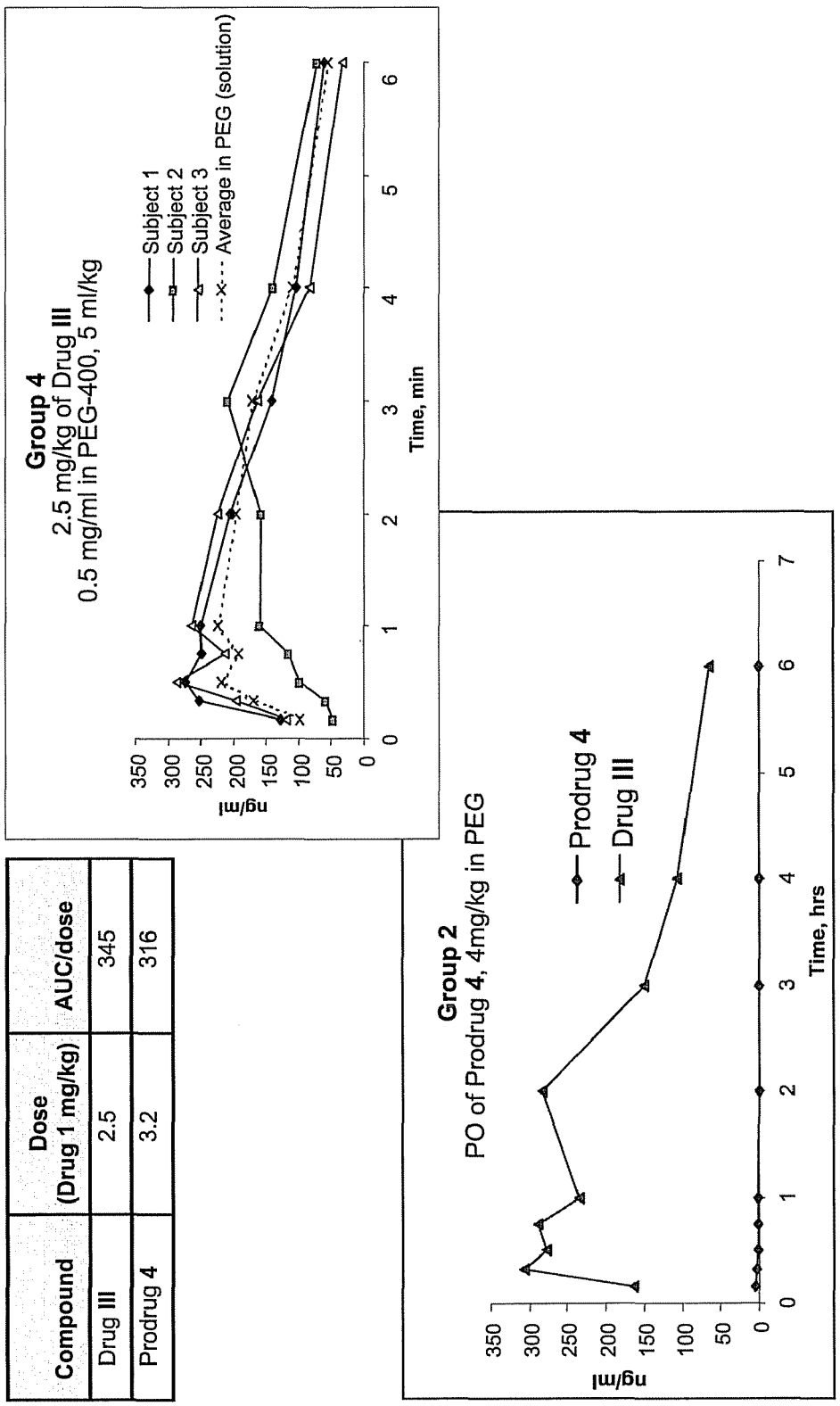

FIG. 18 compares drug Compound III exposure in Sprague-Dawley rats following oral administration of either drug Compound III (2.5 mg/kg in PEG-400) or prodrug Compound 4 (4 mg/kg in PEG-400). The values for AUC/dose are nearly identical indicating that the prodrug Compound 4 is absorbed equally as well as drug Compound III.

Figure 19:
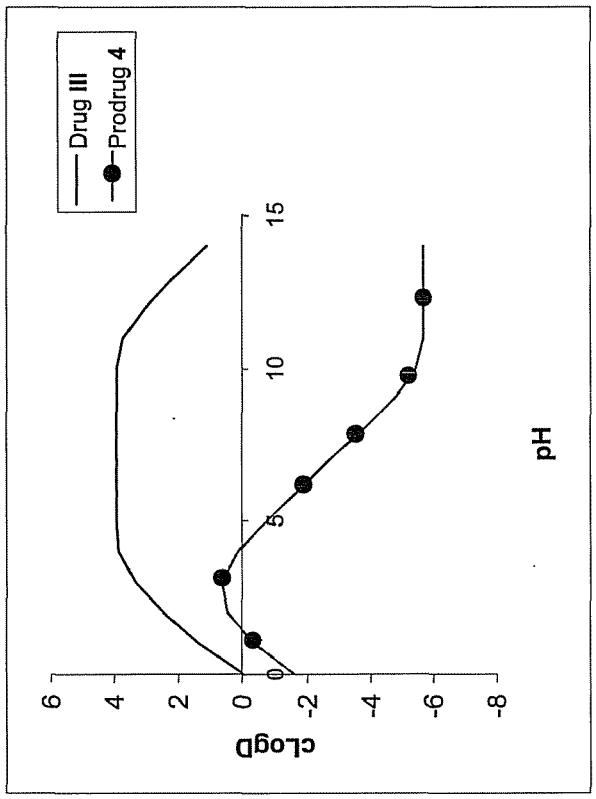

FIG. 19 shows a plot of cLogD vs pH calculated using in-situ predictions for both Compound III and Compound 4. Compound III is highly liphophilic and only weakly ionizable (measured solubility is less than 1 mcg/ml in phosphate buffer at pH=7.5, data not shown). In contrast, Compound 4 is highly polar at neutral pH. Measured solubility values are consistent with the predicted cLogD values at pH=7.5.

Figure 20:
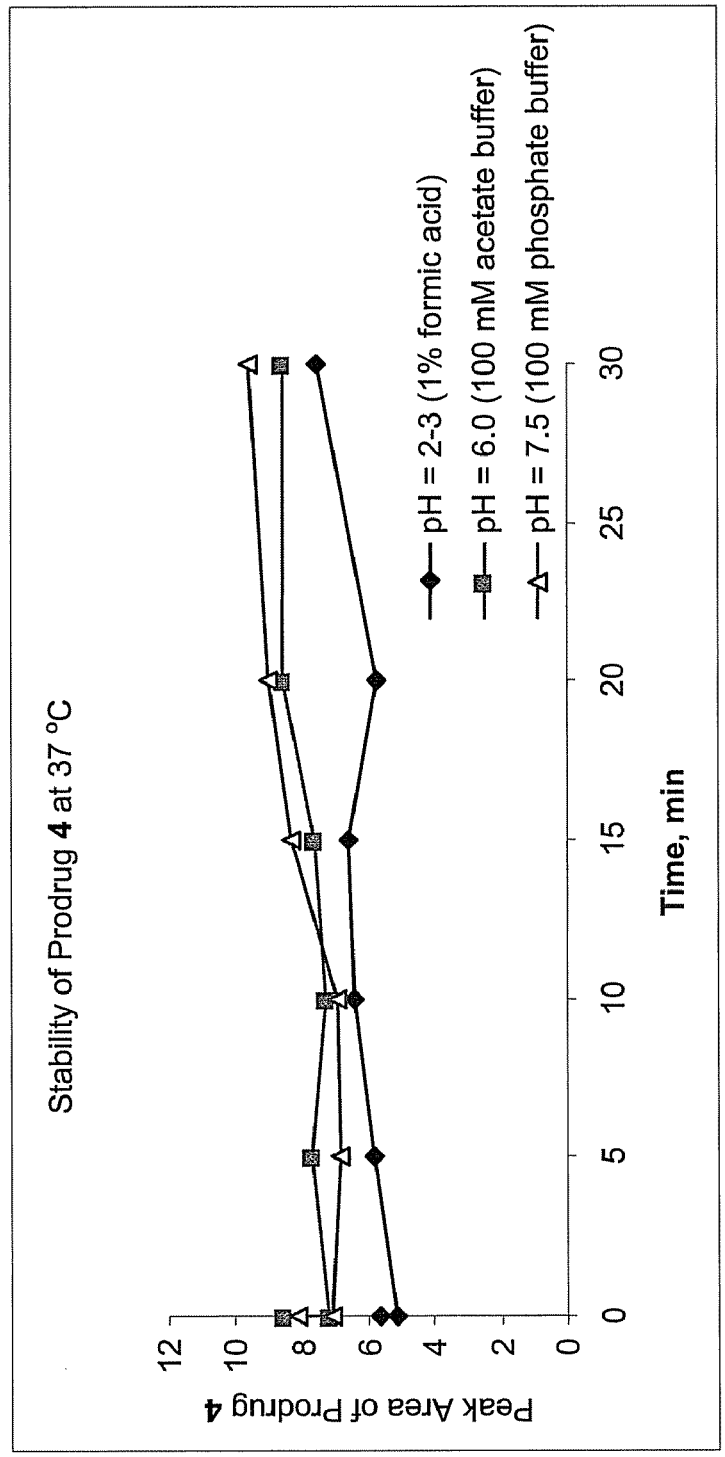

FIG. 20 demonstrates that prodrug Compound 4 is stable under acidic and neutral conditions at 37° C.

Figure 21:
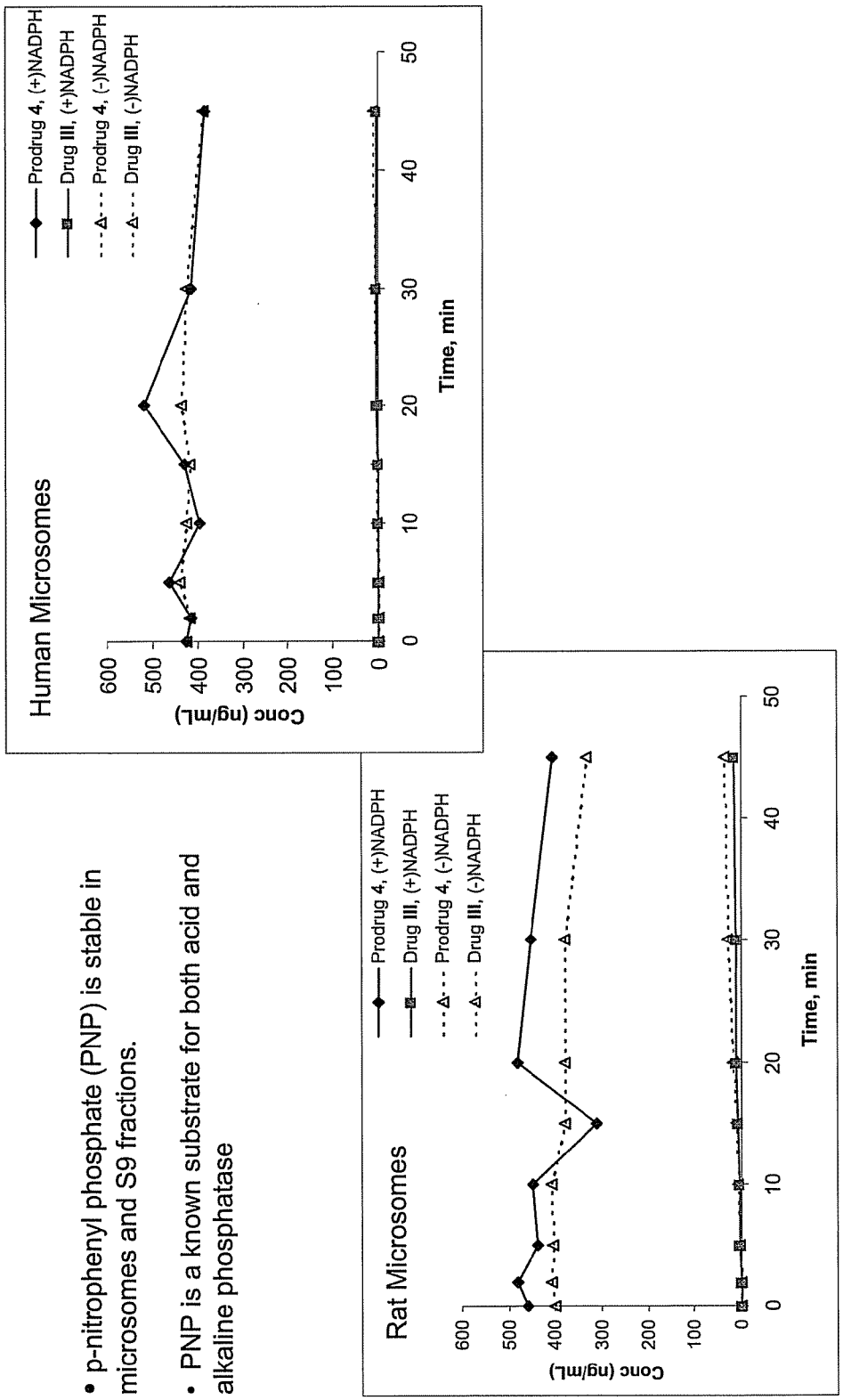

FIG. 21 illustrates the conversion of prodrug Compound 4 to drug Compound III in microsome preparations. Prodrug Compound 4 failed to convert to drug Compound III in microsomal preparations obtained from Xenotech. In follow-up studies using intestinal and hepatic microsomes obtained from a different source, conversion of Compound 4 to Compound III was observed (data not shown).

Figure 22:
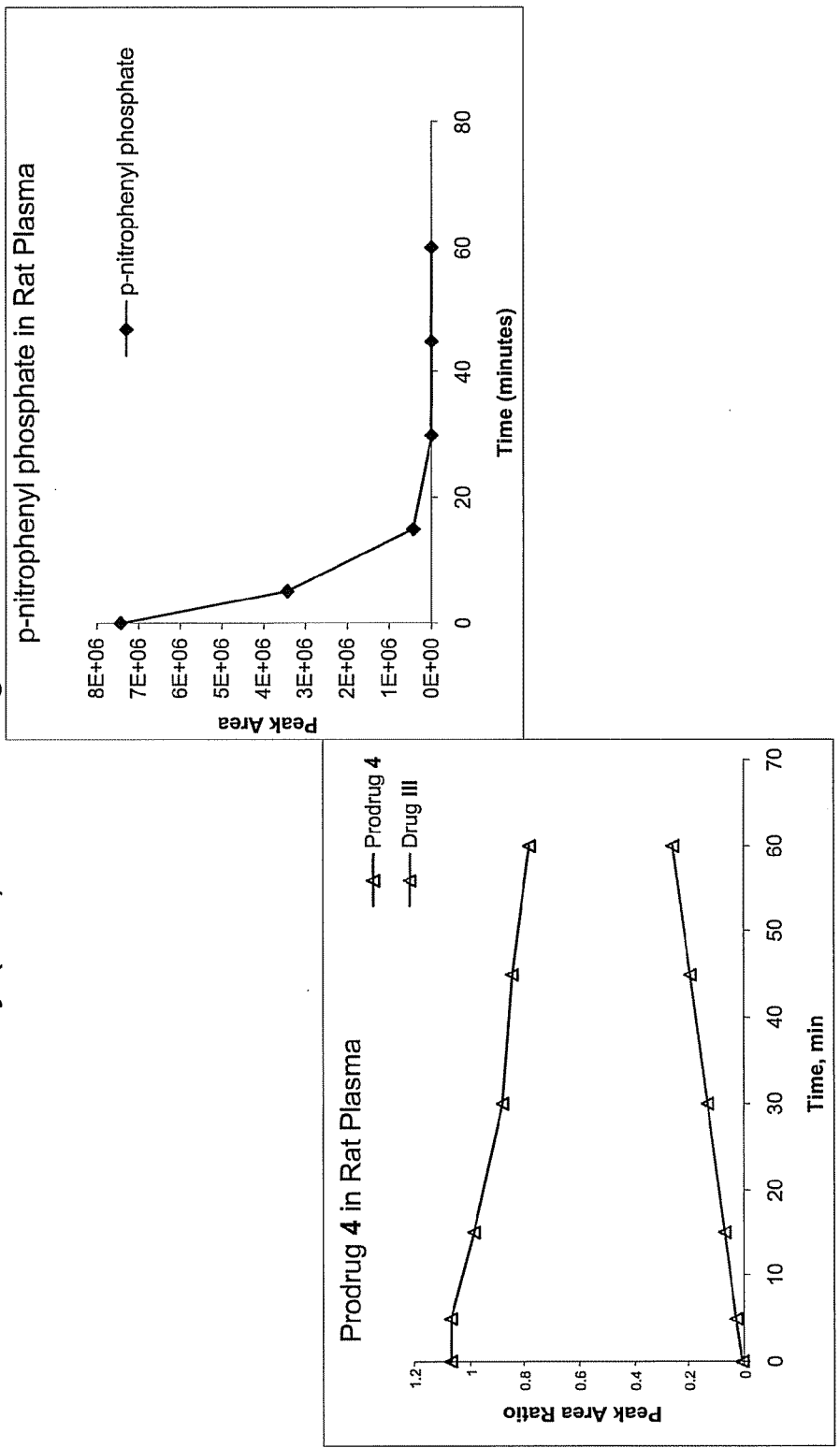

FIG. 22 illustrates that prodrug Compound 4 is unstable in rat plasma—hydrolysis to drug Compound III is observed and the conversion to Compound III is thought to be catalyzed by phosphatase enzymes. The presence of Phosphatase activity in rat plasma was confirmed using p-nitrophenyl phosphate—a known substrate for phosphatase.

Figure 23:
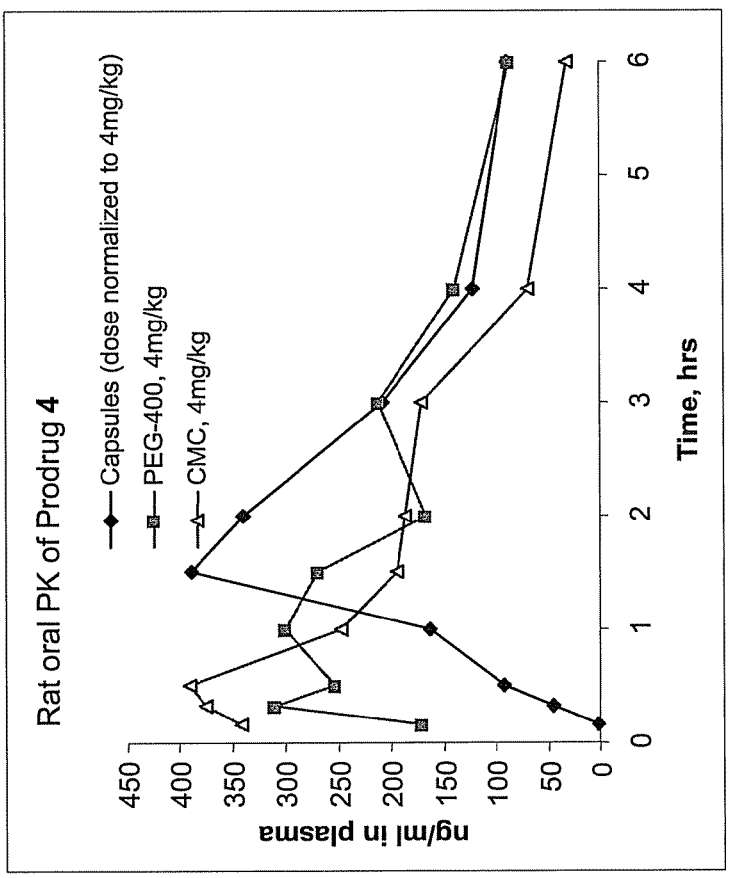

FIG. 23 illustrates the absorption of prodrug Compound 4 from different vehicles. Unlike drug Compound III, absorption of prodrug Compound 4 is not dependent on formulation. Prodrug Compound 4 is absorbed equally well in solution formulations (PEG-400 and carboxymethylcellulose (CMC)) and as a powder in hard gelatin capsules.

Based on the pharmacokinetic data, the oral bioavailability (% F) of prodrug Compound 4 from all three vehicles tested (PEG-400 solution; CMC Solution; and powder in capsules) was determined to be approx. 30%.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

All patents, patent applications, publications, and references cited herein are expressly incorporated by reference to the same extent as if each individual publication or patent application was specifically and individually indicated to be incorporated by reference.

What is claimed is:
1. A method of treating a cell proliferative disorder, comprising:
administering to a subject in need thereof an amount of a prodrug, or a salt thereof, of a Syk kinase inhibitory compound effective to treat the cell proliferative disorder, the prodrug having the structure

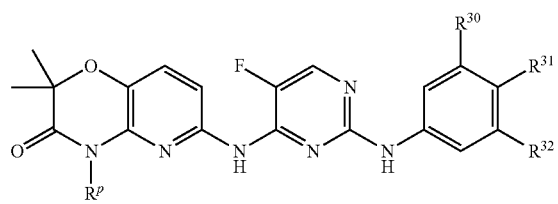

wherein
each $R^{30}$, $R^{31}$ and $R^{32}$ is independently selected from hydrogen, lower alkyl, lower alkenyl, lower alkynyl, (C6-C14) aryl, phenyl, 5-14 membered heteroaryl, (C7-C20) arylalkyl, benzyl, 7-20 membered heteroarylalkyl, —OR, chloro, fluoro, bromo, cyano, nitro, —C(O)R, —C(O)OR, —NRR, —S(O)$_2$NRR, —C(O)NRR, —N(R)S(O)₂R and —NC(O)OR, where each R is independently selected from hydrogen and lower alkyl; and $R^P$ is selected from —CH₂—O—P(O)(OH)₂, —CH₂CH₂—O—P(O)(OH)₂, —CH₂OH.

2. The method of claim 1 in which the cell proliferative disorder is a hematopoietic neoplasm.

3. The method of claim 2 in which the hematopoietic neoplasm is a lymphoid neoplasm.

4. The method of claim 3 in which the lymphoid neoplasm is a T cell neoplasm.

5. The method of claim 4 in which the T cell neoplasm is T lymphoblastic leukemia.

6. The method of claim 3 in which the lymphoid neoplasm is a B cell neoplasm.

7. The method of claim 6 in which the B cell neoplasm is B-lymphoblastic leukemia.

8. The method of claim 6 in which the B cell neoplasm is Burkitt's lymphoma.

9. The method of claim 1 in which the cell proliferative disorder is a myeloid neoplasm.

10. The method of claim 9 in which the myeloid neoplasm is a myeloproliferative disease.

11. The method of claim 10 in which the myeloproliferative disease is chronic myelogenous leukemia (CML).

12. The method of claim 9 in which the myeloid neoplasm is myelodysplastic disease.

13. The method of claim 12 in which the myelodysplastic disease is chronic myelomonocytic leukemia.

14. The method of claim 9 in which the myeloid neoplasm is myelodysplastic syndrome.

15. The method of claim 9 in which the myeloid neoplasm is acute myeloid leukemia.

16. The method of claim 15 in which the acute myeloid leukemia is associated with activity of a TEL/Syk fusion protein.

17. The method of claim 2 in which the hematopoietic neoplasm is selected from acute myelogenous leukemia, B-precursor cell acute lymphoblastic leukemia, T-cell acute lymphoblastic leukemia, myelodysplastic syndrome, and chronic myelogenous leukemia.

18. The method of claim 1 in which the proliferative disorder is a virally-mediated tumor arising from modulation of Syk kinase activity.

19. The method of claim 18 in which the virally mediated tumor arising from modulation of Syk kinase activity.

20. The method of claim 18 in which the virally mediated tumor is associated with Karposi's sarcoma associated herpes virus.

21. The method of claim 20 in which the virally mediated tumor is associated with the activity of K1 protein of Karoposi's sarcoma associated herpes virus.

22. The method of claim 18 in which the virally mediated tumor is associated with Epstein Barr Virus.

23. The method of claim 22 in which the virally mediated tumor is associated with the activity of LMP2A protein of the Epstein Barr Virus.

24. The method of claim 18 in which the virally mediated tumor is associated with HTLV-1 virus.

25. The method of claim 1 in which the prodrug is of the formula:

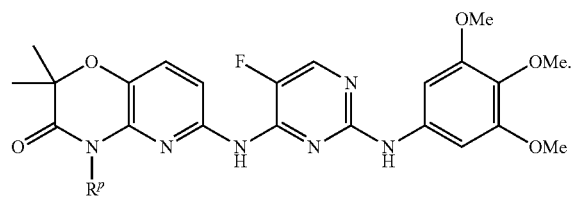

26. The method of claim 1, in which the prodrug is administered in combination with another Syk inhibitory compound.

27. The method of claim 1 in which the prodrug is administered adjunctively with an Abl kinase inhibitor.

28. The method of claim 27 in which the Abl kinase inhibitor is 2-phenylaminopyrimidine.

29. The method of claim 27 in which the prodrug and the Abl kinase inhibitor are administered sequentially.

30. The method of claim 27 in which the prodrug and the Abl kinase inhibitor are administered simultaneously.

31. The method of claim 1, wherein the prodrug has the structure

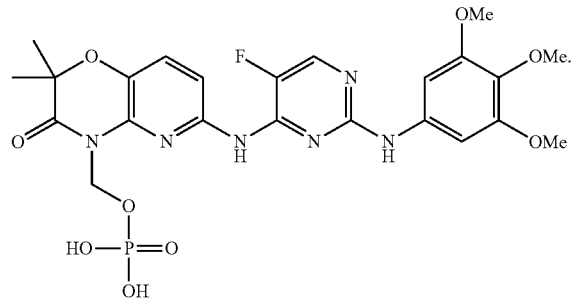

32. The method of claim 31, wherein a salt of the prodrug is administered.

33. The method of claim 32, wherein the salt is a sodium salt, a potassium salt, a lithium salt, an alkylamino salt, a magnesium salt, a calcium salt, or an ammonium salt.

34. The method of claim 1, wherein the prodrug is administered orally.

35. The method of claim 6, wherein the B cell neoplasm is B-cell chronic lymphocytic leukemia.

36. The method of claim 6, wherein the B cell neoplasm is diffuse large B-cell lymphoma.

37. The method of claim 1, wherein the prodrug is administered as a disodium salt.

38. The method of claim 31, wherein the prodrug is administered as a disodium salt.

39. The method of claim 38, wherein the cell proliferative disorder is a B cell neoplasm.

40. The method of claim 39, wherein the B cell neoplasm is diffuse large B-cell lymphoma.

* * * * *